(12) United States Patent
Song et al.

(10) Patent No.: US 11,622,664 B2
(45) Date of Patent: Apr. 11, 2023

(54) FIBROUS STRUCTURES HAVING A CONTACT SURFACE

(71) Applicant: The Procter & Gamble Company, Cincinnati, OH (US)

(72) Inventors: Cunming Song, Symmes Township, OH (US); Hailing Bao, Blue Ash, OH (US); Antonius Lambertus DeBeer, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 145 days.

(21) Appl. No.: 15/834,692

(22) Filed: Dec. 7, 2017

(65) Prior Publication Data

US 2018/0160875 A1 Jun. 14, 2018

Related U.S. Application Data

(60) Provisional application No. 62/431,466, filed on Dec. 8, 2016.

(51) Int. Cl.
| | |
|---|---|
| *A47L 13/17* | (2006.01) |
| *D01F 6/62* | (2006.01) |
| *D01F 6/04* | (2006.01) |
| *A61F 13/511* | (2006.01) |
| *A61F 13/512* | (2006.01) |
| *D04H 5/00* | (2012.01) |

(52) U.S. Cl.
CPC ........... *A47L 13/17* (2013.01); *A61F 13/5116* (2013.01); *A61F 13/5125* (2013.01); *A61F 13/51104* (2013.01); *D01F 6/04* (2013.01); *D01F 6/62* (2013.01); *D04H 5/00* (2013.01)

(58) Field of Classification Search
CPC ....... A47L 13/17; D04H 5/00; A61F 13/5125; A61F 13/5116; A61F 13/51104; D01F 6/04; D01F 6/62
See application file for complete search history.

(56) References Cited

U.S. PATENT DOCUMENTS

| | | |
|---|---|---|
| 4,823,427 A | 4/1989 | Gibbs |
| 4,846,821 A | 7/1989 | Lyons et al. |
| 5,916,678 A | 6/1999 | Jackson et al. |
| 5,948,710 A | 9/1999 | Pomplun et al. |
| 6,117,270 A * | 9/2000 | Trokhan ............... D21F 11/006 162/109 |
| 6,440,564 B1 | 8/2002 | McLain et al. |

(Continued)

FOREIGN PATENT DOCUMENTS

| | | | |
|---|---|---|---|
| EP | 0492554 A1 | 7/1992 | |
| EP | 1253242 A2 * | 10/2002 | ............... B32B 3/02 |

(Continued)

OTHER PUBLICATIONS

U.S. Appl. No. 15/834,642, filed Dec. 7, 2017, Cunming Song, et al.

(Continued)

*Primary Examiner* — Nathan L Van Sell
(74) *Attorney, Agent, or Firm* — C. Brant Cook

(57) ABSTRACT

Fibrous structures, for example pre-moistened fibrous structures, having a novel contact surface (micro protrusion surface) and methods for using the fibrous structures and making the fibrous structures are provided.

20 Claims, 22 Drawing Sheets

(56) References Cited

U.S. PATENT DOCUMENTS

| | | |
|---|---|---|
| 6,946,413 B2 | 9/2005 | Lange et al. |
| 7,994,079 B2 | 8/2011 | Chen et al. |
| 8,017,534 B2 | 9/2011 | Harvey et al. |
| 9,296,176 B2 | 3/2016 | Escaffre et al. |
| 9,719,213 B2 | 8/2017 | Miller, IV et al. |
| 2003/0135181 A1 | 7/2003 | Chen |
| 2004/0020614 A1* | 2/2004 | Lindsay ............... D21F 11/006 162/109 |
| 2004/0144406 A1 | 7/2004 | Garabedian et al. |
| 2005/0155631 A1 | 7/2005 | Kilkenny et al. |
| 2005/0217698 A1 | 10/2005 | Mitchell et al. |
| 2005/0247416 A1 | 11/2005 | Forry et al. |
| 2007/0107151 A1 | 5/2007 | Pung et al. |
| 2007/0228064 A1 | 10/2007 | Brennan et al. |
| 2009/0123504 A1 | 5/2009 | Feldkamp et al. |
| 2009/0286437 A1 | 11/2009 | Cunningham et al. |
| 2010/0203291 A1 | 8/2010 | Dyer et al. |
| 2010/0297378 A1 | 11/2010 | Mellin et al. |
| 2011/0039054 A1 | 2/2011 | Cabell et al. |
| 2011/0039469 A1 | 2/2011 | Cabell et al. |
| 2011/0104970 A1 | 5/2011 | Barnholtz et al. |
| 2011/0244199 A1 | 10/2011 | Brennan et al. |
| 2013/0061414 A1 | 3/2013 | Swist et al. |
| 2013/0071624 A1 | 3/2013 | Manifold et al. |
| 2013/0167305 A1 | 7/2013 | Weisman et al. |
| 2013/0216789 A1 | 8/2013 | Kraus et al. |
| 2013/0302566 A1 | 11/2013 | Barnholtz et al. |
| 2014/0179586 A1 | 6/2014 | Letzelter et al. |
| 2014/0259491 A1 | 9/2014 | Colangelo |
| 2014/0308486 A1 | 10/2014 | Butsch et al. |
| 2014/0308518 A1 | 10/2014 | Gordon et al. |
| 2014/0323381 A1 | 10/2014 | Hatzelt et al. |
| 2015/0086659 A1 | 3/2015 | Klofta et al. |
| 2016/0074254 A1 | 3/2016 | Orr et al. |
| 2020/0337515 A1 | 10/2020 | Song et al. |

FOREIGN PATENT DOCUMENTS

| | | | |
|---|---|---|---|
| EP | 1602310 A2 | 12/2005 | |
| EP | 3087895 A1 | 11/2016 | |
| JP | 2013249558 A | 5/2012 | |
| WO | WO-0240769 A2 * | 5/2002 | ............ D21F 11/006 |
| WO | WO 2015/150054 A1 | 10/2015 | |
| WO | WO 2016/078913 A1 | 5/2016 | |

OTHER PUBLICATIONS

U.S. Appl. No. 15/834,672, filed Dec. 7, 2017, Cunming Song, et al.
All Office Actions U.S. Appl. No. 15/834,692.
All Office Actions U.S. Appl. No. 15/834,642.
All Office Actions U.S. Appl. No. 15/834,672.
PCT International Search Report dated Mar. 9, 2018—5 pages.
All Office Actions, U.S. Appl. No. 16/926,836.

* cited by examiner

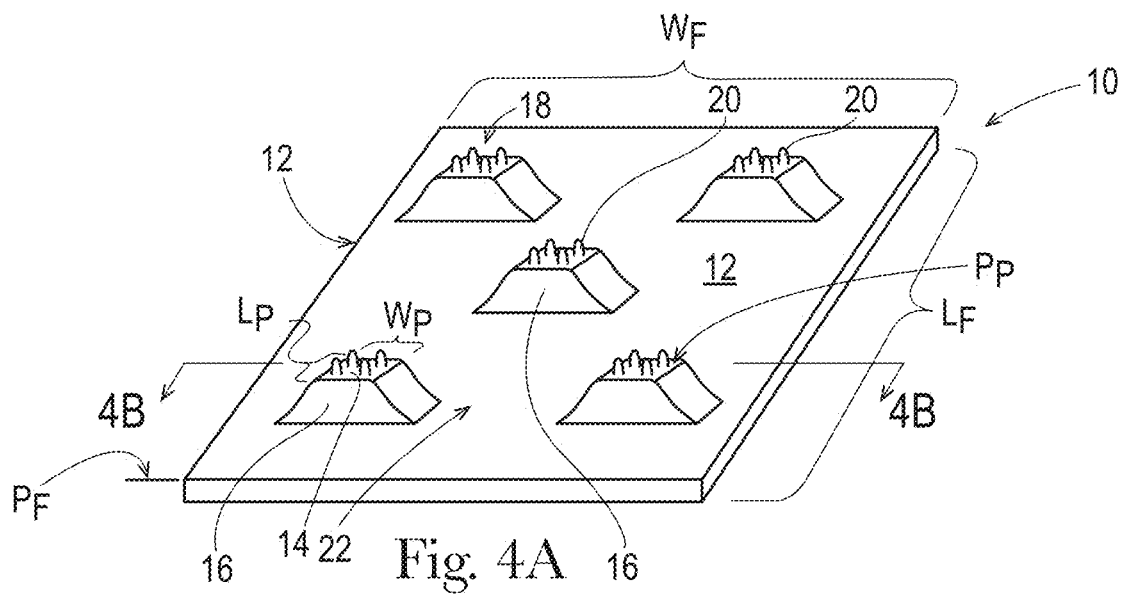
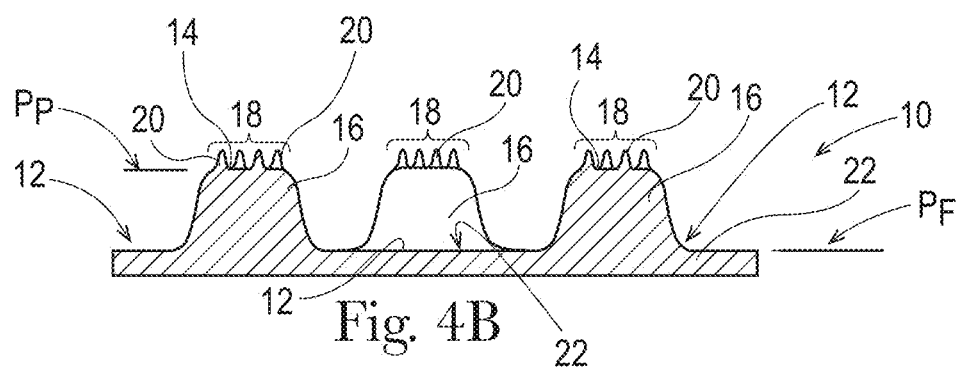
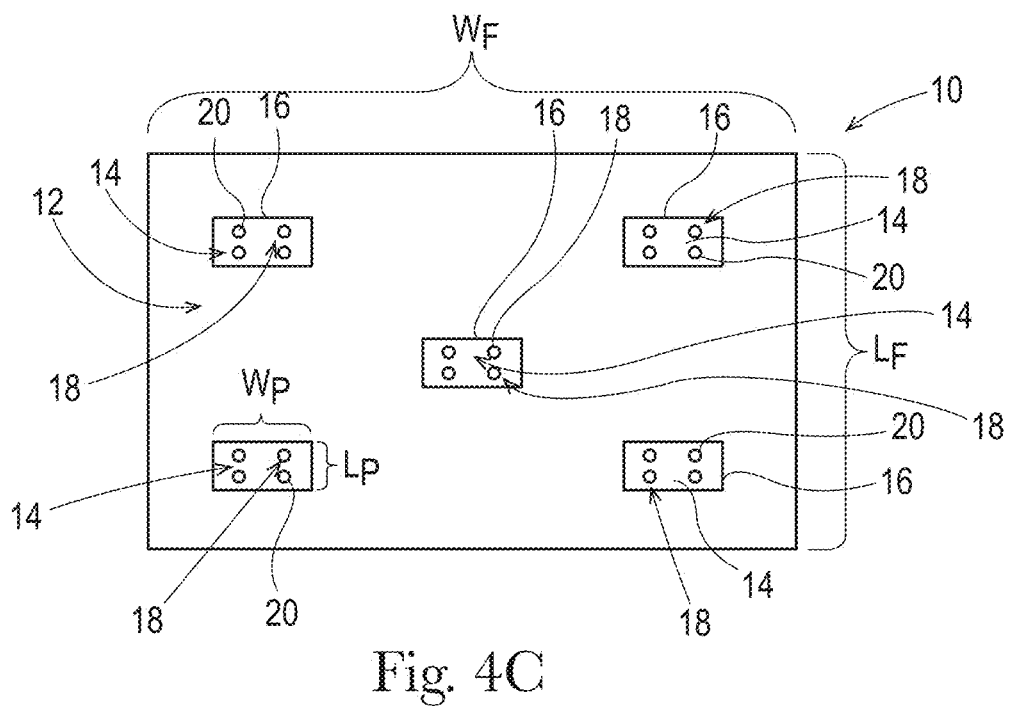

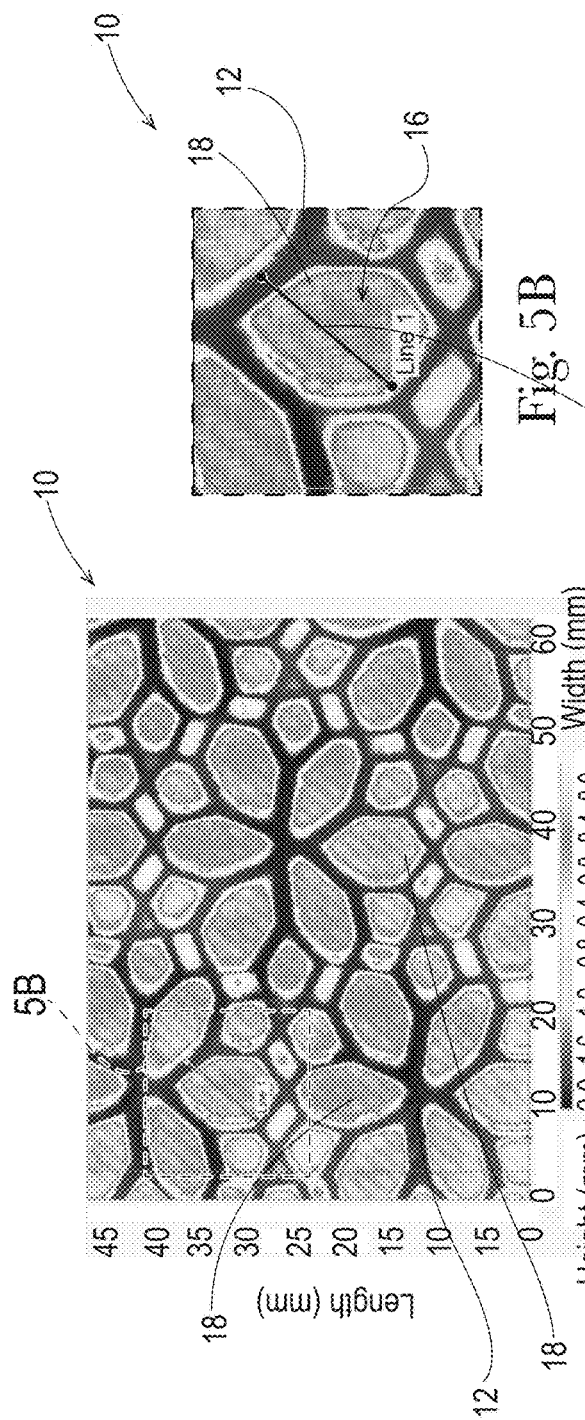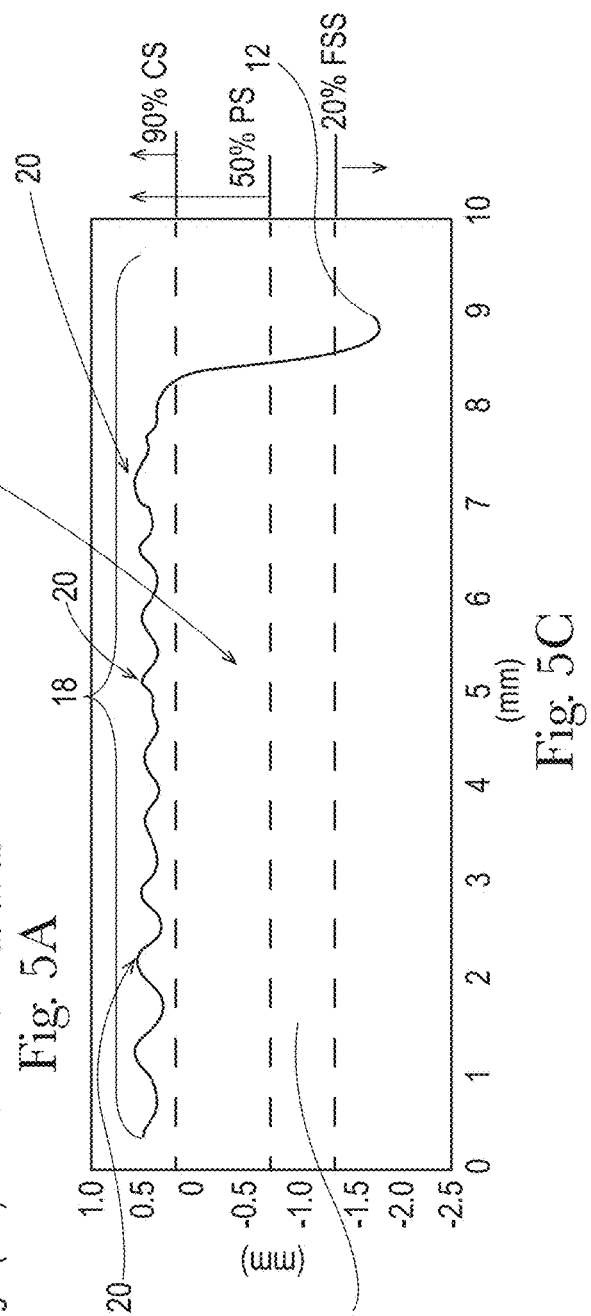
Fig. 5A  Fig. 5B  Fig. 5C

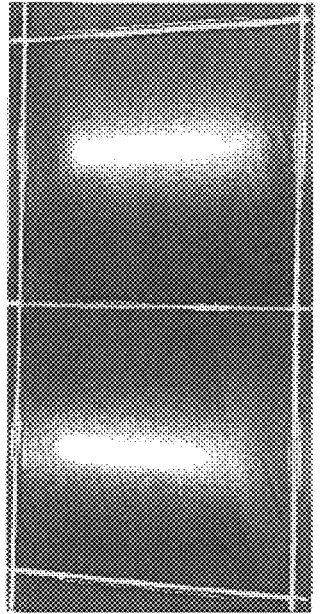
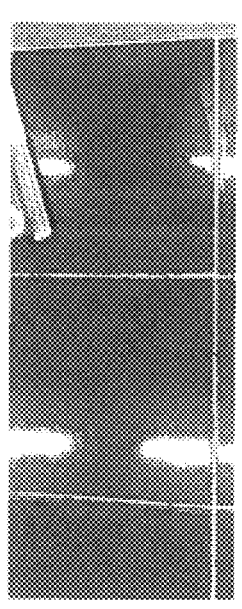
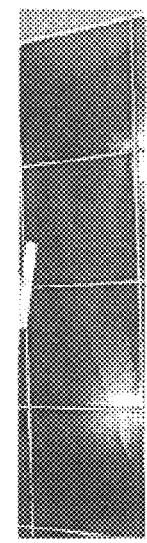
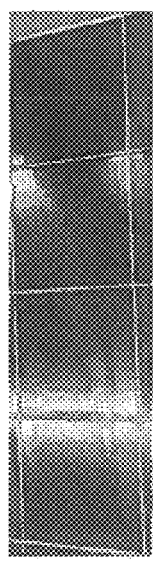
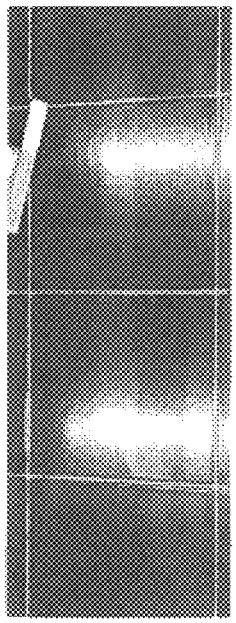
Fig. 20

FIBROUS STRUCTURES HAVING A CONTACT SURFACE

FIELD OF THE INVENTION

The present invention relates to fibrous structures, for example pre-moistened fibrous structures, comprising a novel contact surface (micro protrusion surface), and more particularly, to fibrous structures, for example pre-moistened fibrous structures, having a novel contact surface (micro protrusion surface) formed by one or more contact surface protrusions (micro protrusions) and methods for using the fibrous structures and making the fibrous structures.

BACKGROUND OF THE INVENTION

Pre-moistened fibrous structures, for example wipes and/or floor cleaning pads, in the past have exhibited flat contact surfaces. For example, a known pre-moistened fibrous structure 10 as shown in Prior Art FIGS. 1A and 1B exhibits a flat, non-patterned, for example non-macro patterned, non-embossed, non-molded, fibrous structure surface 12. The flat, non-patterned fibrous structure surface 12 results in the pre-moistened fibrous structure exhibiting a flat functional contact surface having a functional contact surface surface area of 100% of the total fibrous structure surface's 12 surface area. In other words, the total fibrous structure surface's 12 surface area is also the fibrous structure's functional contact surface. Such a flat functional contact surface results in the pre-moistened fibrous structure exhibiting unacceptable friction for a user during use due to phenomenon known as hydrogen bonding. Such high friction can result in flipping and/or chattering of the pre-moistened fibrous structure from the surface (if it is attached to a cleaning implement such as a Swiffer® sweeper) and/or over exertion by the user during cleaning of surfaces, such as floors.

Formulators have attempted to overcome these negatives associated with such known pre-moistened "flat" fibrous structures shown in Prior Art FIGS. 1A and 1B by creating pre-moistened fibrous structures comprising a textured and/or three-dimensional patterned fibrous structure surface. As shown in Prior Art FIGS. 2A and 2B, a known pre-moistened textured fibrous structure 10 comprises a fibrous structure surface 12 comprising one or more, for example a plurality of protruding surfaces, for example macro protrusion surface 14. The protruding surfaces (macro protrusion surfaces 14) are formed by one or more, for example a plurality of macro protrusions 16 (also referred to herein as pillows). The plurality of the macro protrusions 16 results in the pre-moistened fibrous structure 10 exhibiting a protruding surface (a macro protrusion surface 14) having a protruding surface surface area (a macro protrusion surface 14 surface area) of less than 100% of the total fibrous structure surface's 12 surface area. Creating the macro protrusions 16 in FIGS. 2A and 2B can reduce the fibrous structure surface's 12 surface area contacting a surface to be contacted by the fibrous structure 10 during use. Such pre-moistened textured fibrous structures 10 exhibit reduced friction, for example wet friction, of the pre-moistened textured fibrous structure 10 compared to the pre-moistened flat fibrous structures 10 shown in FIGS. 1A and 1B, but they still exhibited consumer negatives because the protruding surfaces (macro protrusion surfaces 14) produced by the macro protrusions 16 were flat, non-textured protruding surfaces (macro protrusion surfaces 14). The reduction in friction, for example wet friction, during use was found to be insufficient due in part to the fact that the protruding surfaces (macro protrusion surfaces 14) were flat or essentially flat and the continued impact of high levels of hydrogen bonding. As mentioned above, such high friction can result in flipping and/or chattering of the pre-moistened fibrous structure from the surface (if it is attached to a cleaning implement such as a Swiffer® sweeper) and/or over exertion by the user during cleaning of surfaces, such as floors. In other words, the macro protrusions 16 and/or protruding surfaces (macro protrusion surfaces 14) do not comprise micro protrusions 20 as shown in FIGS. 3C, 3D, and 4A to 4C, for example.

One problem with the known fibrous structures, for example pre-moistened fibrous structures, such as pre-moistened floor cleaning pads, is that the fibrous structure's surface (for example contact surface) of the pre-moistened fibrous structures, which is whatever surface contacts a surface to be cleaned during use, needs to be such that the pre-moistened fibrous structure exhibits sufficient friction to provide consumer visually noticeable removal of soil from the surface and/or on the fibrous structure, which is influenced at least partly by the surface areas of the functional contact surface area that contacts a surface being treated and non-contact surface area of the fibrous structures, during use to provide cleaning of a surface, such as a hard surface, for example a floor, but not exhibit too much friction to create consumer negatives, such as flipping, bunching, and/or stopping of the fibrous structure during use and/or causing the consumer to exert too much effort during use.

Accordingly, there is a need for a pre-moistened fibrous structure, such as a pre-moistened floor cleaning pad, that comprises a contact surface (a micro protrusion surface) that overcomes the negatives described above, methods of using such pre-moistened fibrous structures and methods for making such pre-moistened fibrous structures.

SUMMARY OF THE INVENTION

The present invention fulfills the needs described above by providing a fibrous structure, for example a pre-moistened fibrous structure, comprising a contact surface (micro protrusion surface) comprising a contact surface pattern (micro protrusion surface pattern).

One solution to the problem identified above is the creation of fibrous structures, for example pre-moistened fibrous structures, such as floor cleaning pads, comprising a contact surface, such as a micro protrusion surface, comprising a contact surface pattern (micro protrusion pattern), such as a pattern of contact surface protrusions (a pattern of micro protrusions).

In one example of the present invention, a fibrous structure comprising a fibrous structure surface comprising one or more protruding surfaces (macro protrusion surfaces) wherein at least one of the protruding surfaces (macro protrusion surfaces) comprises a plurality of contact surface protrusions (micro protrusions), is provided.

In another example of the present invention, a fibrous structure, for example a pre-moistened fibrous structure comprising a fibrous structure surface that exhibits a fibrous structure surface surface area, wherein the fibrous structure surface comprises a contact surface (micro protrusion surface) that exhibits a contact surface surface area (micro protrusion surface surface area), wherein the contact surface surface area (micro protrusion surface surface area) is less than the fibrous structure surface surface area, and wherein the contact surface (micro protrusion surface) comprises a contact surface pattern (micro protrusion surface pattern), is provided.

In another example of the present invention, a fibrous structure, for example a pre-moistened fibrous structure, comprising a fibrous structure surface that exhibits a fibrous structure surface surface area, wherein the fibrous structure surface comprises one or more macro protrusions, wherein at least one of the macro protrusions comprises a contact surface pattern, for example a plurality of micro protrusions, is provided.

In another example of the present invention, a method for making a fibrous structure, for example a pre-moistened fibrous structure, according to the present invention, the method comprising the step of:
 a. producing a fibrous structure, for example a pre-moistened fibrous structure, comprising one or more macro protrusions and one or more micro protrusions on one or more surfaces of the macro protrusions (for example such that the one or more micro protrusions form one or more contact surfaces (one or more micro protrusion surfaces)), wherein at least one of the macro protrusions comprises a contact surface pattern (a micro protrusion pattern or one or more micro protrusions), is provided.

In another example of the present invention, a method for making a fibrous structure, for example a pre-moistened fibrous structure according to the present invention, the method comprising the steps of:
 a. providing a fibrous structure, for example a pre-moistened fibrous structure, comprising one or more macro protrusions (for example that form one or more macro protrusion surfaces); and
 b. imparting a contact surface pattern (micro protrusion pattern or micro protrusions) to one or more of the macro protrusions (for example one or more of the macro protrusion surfaces), is provided.

In another example of the present invention, a method for making a fibrous structure, for example, pre-moistened fibrous structure according to the present invention, the method comprising the steps of:
 a. providing a fibrous structure comprising a contact surface (a micro protrusion surface) comprising a contact surface pattern (micro protrusion pattern formed by a plurality of micro protrusions); and
 b. applying a liquid composition to the fibrous structure to form a pre-moistened fibrous structure, is provided.

In another example of the present invention, a method for making a fibrous structure, for example a pre-moistened fibrous structure according to the present invention, the method comprising the steps of:
 a. providing a fibrous structure comprising one or more macro protrusions, for example two or more macro protrusions, for example a plurality of macro protrusions, wherein at least one or more and/or two or more and/or a plurality of the macro protrusions comprise a contact surface pattern (a micro protrusion pattern formed by a plurality of micro protrusions); and
 b. applying a liquid composition to the fibrous structure to form a pre-moistened fibrous structure, is provided.

In still another example of the present invention, a method for making a fibrous structure, for example a pre-moistened fibrous structure according to the present invention, the method comprising the steps of:
 a. spinning a plurality of filaments from a filament source,
 b. mixing a plurality of solid additives, such as fibers, for example pulp fibers, with the filaments to form a filament/solid additive mixture,
 c. collecting the filament/solid additive mixture on a collection device to form a fibrous structure having one or more macro protrusions, wherein at least one of the one or more macro protrusions comprises a contact surface pattern (a micro protrusion pattern formed by a plurality of micro protrusions); and
 d. applying a liquid composition to the fibrous structure to form a pre-moistened fibrous structure, is provided.

In still another example of the present invention, a method for making a fibrous structure, for example a pre-moistened fibrous structure according to the present invention, the method comprising the steps of:
 a. spinning a plurality of first filaments from a first filament source,
 b. collecting the first filaments on a collection device to form a first fibrous structure, for example a scrim,
 c. spinning a plurality of second filaments from a second filament source,
 d. mixing a plurality of solid additives, such as fibers, for example pulp fibers, with the second filaments to form a second filament/solid additive mixture,
 e. collecting the second filament/solid additive mixture on the first fibrous structure while the first fibrous structure is on the collection device to form a layered fibrous structure having one or more macro protrusions, wherein at least one of the one or more macro protrusions comprises a contact surface pattern (a micro protrusion pattern formed by a plurality of micro protrusions); and
 f. optionally, spinning a plurality of third filaments from a third filament source and collecting the third filaments on the layered fibrous structure such that the second filament/solid additive mixture is positioned between the first and third filament layers,
 g. applying a liquid composition to the fibrous structure to form a pre-moistened fibrous structure, is provided.

In yet another example of the present invention, a method of using a fibrous structure, for example a pre-moistened fibrous structure, according to the present invention to treat a surface to be cleaned, the method comprising the step of:
 a. contacting a surface to be cleaned with a fibrous structure, for example a pre-moistened fibrous structure, according to the present invention, such that the surface is cleaned, is provided.

In yet another example of the present invention, a method for using a fibrous structure, for example a pre-moistened fibrous structure, according to the present invention to treat a surface to be cleaned, the method comprising the steps of:
 a. providing a cleaning implement suitable for receiving a fibrous structure, for example a pre-moistened fibrous structure, according to the present invention,
 b. providing a fibrous structure, for example a pre-moistened fibrous structure, according to the present invention,
 c. associating the fibrous structure, for example a pre-moistened fibrous structure, with the cleaning implement to form a cleaning system; and
 d. contacting a surface to be cleaned with a fibrous structure, for example a pre-moistened fibrous structure, according to the present invention, such that the surface is cleaned, is provided.

In still another example of the present invention, a method for making a cleaning system, the method comprising the steps of:
 a. providing a cleaning implement suitable for receiving a fibrous structure, for example a pre-moistened fibrous structure, according to the present invention, b. providing a fibrous structure, for example a pre-moistened fibrous structure, according to the present invention; and c. associating the fibrous structure, for example a pre-moistened fibrous structure, with the cleaning implement to form a cleaning system, is provided.

The present invention provides a novel fibrous structure, for example a novel pre-moistened fibrous structure, a method of making such fibrous structure, for example a pre-moistened fibrous structure, a method for using such fibrous structure, for example a pre-moistened fibrous structure, a cleaning system comprising such fibrous structure, for example a pre-moistened fibrous structure, and a method for making and/or using such a cleaning system.

BRIEF DESCRIPTION OF THE DRAWINGS

FIG. 4A is a perspective view of an example of a fibrous structure according to the present invention;

FIG. 4B is a cross-sectional view of the fibrous structure of FIG. 4A taken along line 4B-4B;

FIG. 4C is a top plan view of the fibrous structure of FIG. 4A;

FIG. 5A is a MikroCAD image of a fibrous structure according to the present invention;

FIG. 5B is a magnified image of a portion of the Mikro-CAD image of FIG. 5A;

FIG. 5C is a profile representation of the magnified image of FIG. 5B;

FIG. 20 is an array of images showing streak levels for the Mileage Test Method.

DETAILED DESCRIPTION OF THE INVENTION

Definitions

Figure 1A:
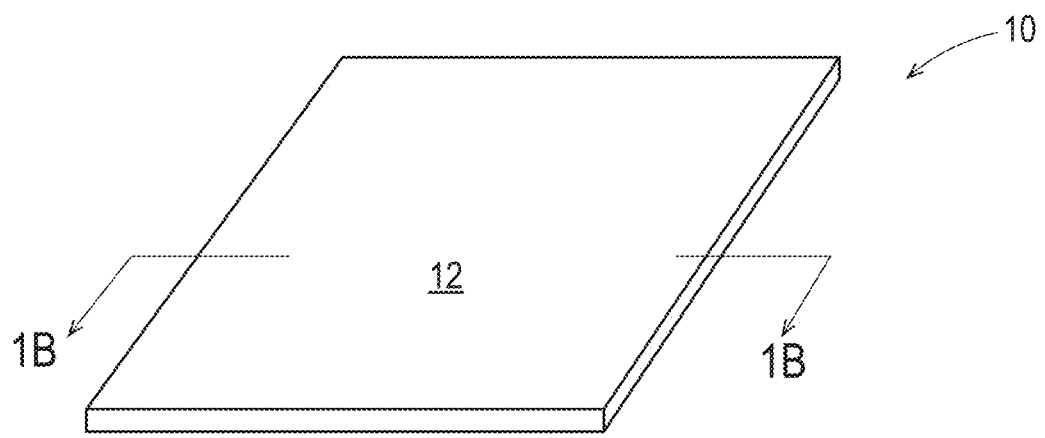
FIG. 1A is a perspective view of an example of a "flat" prior art fibrous structure.
Figure 1B:
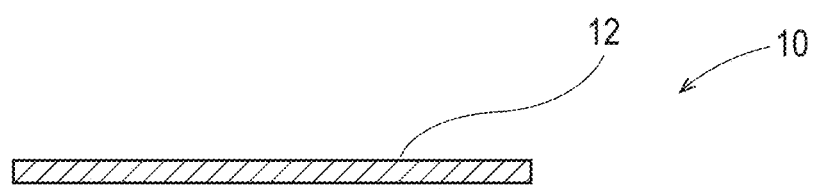
FIG. 1B is cross-sectional view of the prior art fibrous structure of FIG. 1A taken along line 1B-1B.
Figure 2A:
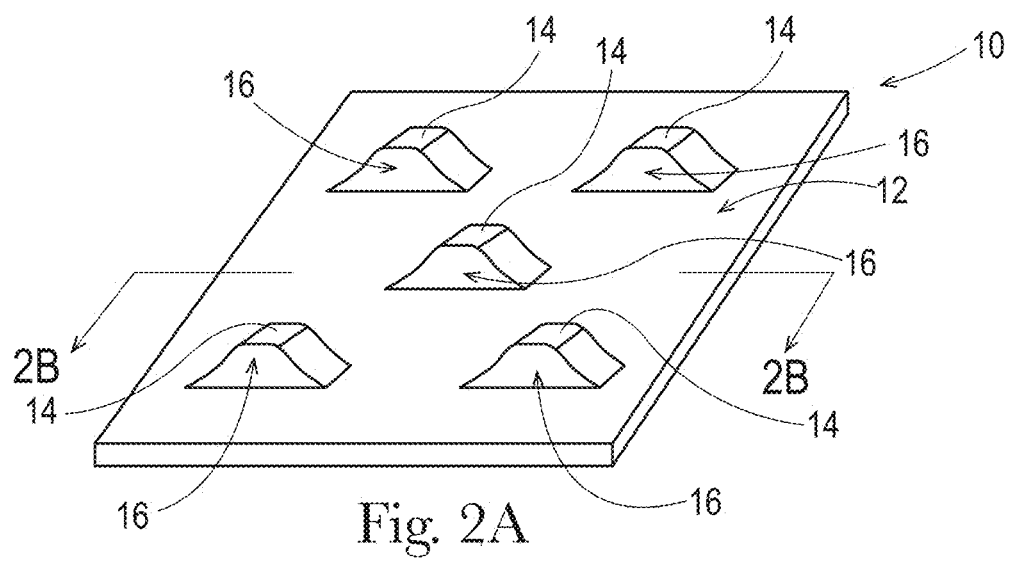
FIG. 2A is a perspective view of an example of another prior art fibrous structure.
Figure 2B:
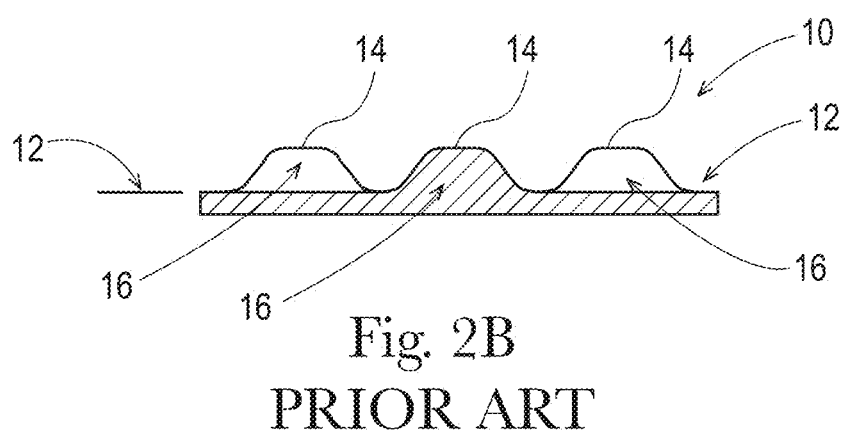
FIG. 2B is a cross-sectional view of the prior art fibrous structure of FIG. 2A taken along line 2B-2B.

"Fibrous structure" as used herein means a structure that comprises a plurality of filaments and/or a plurality of solid additives, such as fibers, for example pulp fibers, for example wood pulp fibers, and/or particles, such as superabsorbent materials. In one example, a fibrous structure according to the present invention means an orderly arrangement of filaments and fibers within a structure in order to perform a function. In another example, a fibrous structure according to the present invention is a nonwoven.

Non-limiting examples of processes for making fibrous structures include meltblowing and/or spunbonding processes. In one example, the fibrous structures of the present invention are made via a process comprising meltblowing. In another example, the fibrous structures of the present invention are made by meltblowing and coforming (mixing a plurality of filaments, such as meltblown and/or spunbond, for example meltblown filaments with a plurality of solid additives, such as fibers, for example pulp fibers such as wood pulp fibers, and collecting the mixture on a collection device to form a co-formed fibrous structure).

The fibrous structure of the present invention may comprise at least three different surfaces: 1) a fibrous structure surface, 2) a protruding surface (macro protrusion surface); and 3) a contact surface (micro protrusion surface). Each of the surfaces exhibits a surface area, for example the fibrous structure surface exhibits a fibrous structure surface surface area, the protruding surface (macro protrusion surface) exhibits a protruding surface surface area (macro protrusion surface surface area), and the contact surface (micro protrusion surface) exhibits a contact surface surface area (micro protrusion surface surface area). The at least three surfaces and/or surface areas of the surfaces may be identified visually since they will be visually discernible and/or with or without the aid of cross-sectional images of the fibrous structures and/or by MikroCAD images, profiles, and/or measurements according to the MikroCAD Test Method described herein.

The fibrous structures of the present invention may be homogeneous or may be layered. If layered, the fibrous structures may comprise at least two and/or at least three and/or at least four and/or at least five layers.

The fibrous structures of the present invention may be co-formed fibrous structures.

In one example, the fibrous structure, for example the pre-moistened fibrous structure, is a saleable unit and/or a useable unit in a form and/or shape that a consumer purchases and/or uses.

"Co-formed fibrous structure" as used herein means that the fibrous structure comprises a mixture of at least two different materials wherein at least one of the materials, for example a first material, comprises filaments, such as polypropylene filaments, and at least one other material, for example a second material, different from the first material, comprises solid additives, such as pulp fibers and/or particulates. In one example, a co-formed fibrous structure comprises solid additives, such as pulp fibers, such as wood pulp fibers, and filaments, such as polypropylene filaments that are commingled together.

Figure 3A:
FIG. 3A is a schematic representation of an example of a fibrous structure surface of a fibrous structure according to the present invention.
Figure 3B:
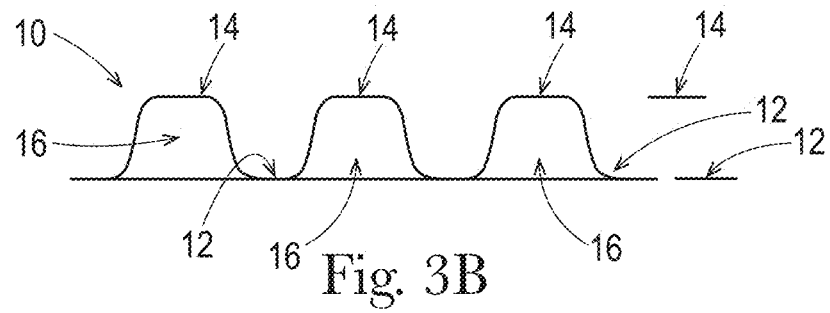
FIG. 3B is a schematic representation of an example of a fibrous structure surface and a protruding surface (macro protrusion surface(s)) of a fibrous structure according to the present invention.
Figure 3C:
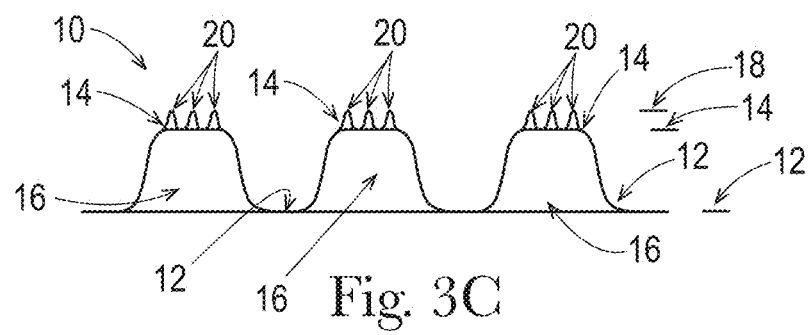
FIG. 3C is a schematic representation of an example of a fibrous structure surface, a protruding surface (macro protrusion surface(s)), and a contact surface (micro protrusion surface(s)) of a fibrous structure according to the present invention.
Figure 3D:
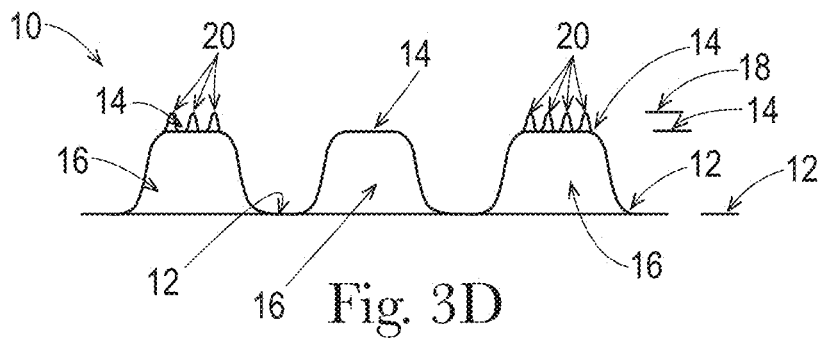
FIG. 3D is a schematic representation of an example of a fibrous structure surface, a protruding surface (macro protrusion surface(s)), and a contact surface (micro protrusion surface(s)) of a fibrous structure according to the present invention.

As mentioned previously, the fibrous structures 10 of the present invention may comprise at least three different surfaces, namely, a fibrous structure surface, a protruding surface (macro protrusion surface 14), and a contact surface (micro protrusion surface 18) formed by micro protrusions 20. FIGS. 3A-3D schematically represent the different surfaces of the fibrous structures of the present invention. For example, FIG. 3A schematically represents the fibrous structure surface 12 of the fibrous structure 10. As used herein, the fibrous structure surface 12 is considered the "flat surface" state of the fibrous structure 10. FIG. 3B schematically represents the protruding surface (macro protrusion surface 14) as a portion of the fibrous structure surface 12 of the fibrous structure 10. One or more macro protrusions 16 on the fibrous structure surface 12 may form one or more, for example all of the protruding surfaces (macro protrusion surfaces 14). FIGS. 3C and 3D schematically represent a contact surface (micro protrusion surface 18) as a portion of the protruding surface (macro protrusion surface 14), which is a portion of the fibrous structure surface 12 of the fibrous structure 10. One or more contact surface protrusions (micro protrusions 20) on one or more protruding surfaces (macro protrusion surfaces 14) may form one or more, for example all of the contact surfaces (micro protrusion surfaces 18). During use of the fibrous structure 10, at least one of the contact surfaces (micro protrusion surfaces 18) is the surface of the fibrous structure 10 that contacts a surface being cleaned and/or is most proximal to the surface being cleaned relative to the fibrous structure surface 12 and the protruding surface (macro protrusion surface 14) of the fibrous structure 10. In one example, as shown in FIG. 3D, not all of the protruding surfaces (macro protrusion surfaces 14) need to comprise contact surface protrusions (micro protrusions 20).

As schematically shown in FIGS. 3A-3D and 4A-4C, the fibrous structure surface 12 exhibits a fibrous structure surface surface area, the protruding surface (macro protrusion surface 14) exhibits a protruding surface surface area (macro protrusion surface 14 surface area), and the contact surface (micro protrusion surface 18) exhibits a contact surface surface area (micro protrusion surface 18 surface area), wherein the total contact surface surface area (total micro protrusion surface 18 surface area) is less than the total protruding surface surface area (total macro protrusion surface 14 surface area) and/or wherein the total protruding surface surface area (total macro protrusion surface 14 surface area) is less than the total fibrous structure surface 12 surface area. In one example, the protruding surface surface area (the macro protrusion surface 14 surface area) of at least one protruding surface (macro protrusion surface 14) is greater than the contact surface surface area (micro protrusion surface 18 surface area) of a contact surface (micro protrusion surface 18) on the protruding surface (macro protrusion surface 14).

Figure 5D:
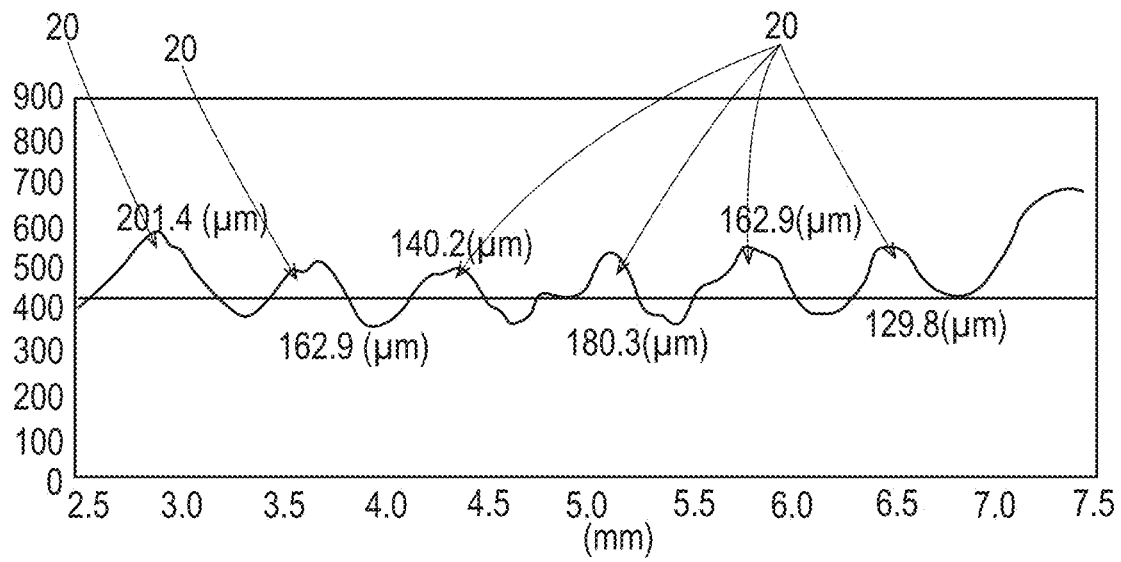
FIG. 5D is a profile representation of a portion of the profile representation of FIG. 5C.
Figure 5E:
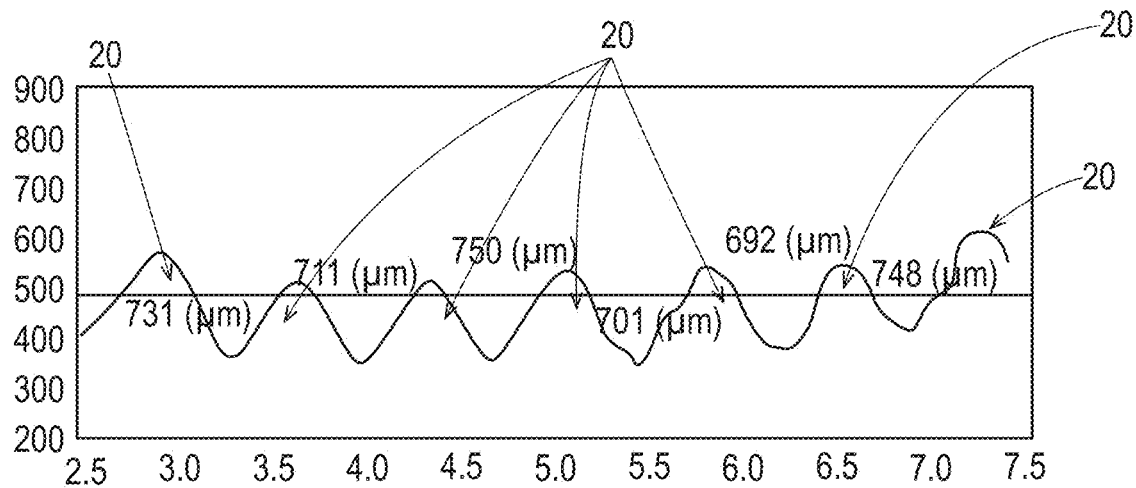
FIG. 5E is a profile representation of a portion of the profile representation of FIG. 5C.

"Fibrous structure surface" 12 as used herein, in one example, means the surface of a fibrous structure 10 at less than 20% and/or less than 10% and/or less than 5% and/or less than 3% and/or about 0% of the maximum height of the fibrous structure 10 as measured according to the MikroCAD Test Method described herein as shown in FIGS. 5A-5E. As shown in FIG. 5A-5E, an example of a fibrous structure 10 according to the present invention (as represented in the MikroCAD Images and corresponding MikroCAD Profiles) comprises a fibrous structure surface 12, in other words, the fibrous structure's surface at less than 20% and/or less than 10% and/or less than 5% and/or less than 3% and/or about 0% of the maximum height (referred to as "FSS" in FIG. 5C). FIG. 5D shows the Peak to Valley (Amplitude) values for the contact surface protrusions (micro protrusions 20) as being at least 129.8 μm and FIG. 5E shows the Peak to Peak (Wavelength) values for the contact surface protrusions (micro protrusions 20) as being at least 692 μm. For purposes of the present invention, the line (for example as represented by "Line 1") drawn to measure Peak to Valley and the Peak to Peak are drawn to maximize the number of peaks the line crosses. In one example, the contact surface protrusions (micro protrusions 20) on the fibrous structures of the present invention exhibit a Peak to Valley (Amplitude) value of greater than 50 and/or greater than 75 and/or greater than 100 and/or greater than 1.25 and/or greater than 150 and/or greater than 200 μm. In one example, the contact surface protrusions (micro protrusions 20) on the fibrous structures of the present invention exhibit a Peak to Peak (Wavelength) value of greater than 100 and/or greater than 200 and/or greater than 300 and/or greater than 400 and/or greater than 500 and/or greater than 600 and/or greater than 700 μm. In one example, the contact surface protrusions (micro protrusions 20) on the fibrous structures of the present invention exhibit a Valley to Valley value of greater than 100 and/or greater than 200 μm.

In one example as shown in FIGS. 4A-4C, 5A-5C and 6A-6B, the fibrous structure surface 12, especially for a textured and/or three-dimensional patterned fibrous structure, may comprise one or more protruding surfaces (macro protrusion surfaces 14) formed by one or more macro protrusions 16 relative to the fibrous structure surface's plane $P_F$, for example one or more macro protrusions 16, one or more of which comprises a contact surface (micro protrusion surface 18) formed by one or more contact surface protrusions (micro protrusions 20), and one or more fibrous structure surface 12 non-raised and/or recessed regions 22 relative to the plane $P_F$, which may itself form part of the plane $P_F$, of the fibrous structure surface 12, one or more of which comprises a non-contact surface relative to the contact surface (micro protrusion surface 18). In one example, the one or more macro protrusions 16 may be referred to as pillows and the one or more fibrous structure surface 12 non-raised and/or recessed regions 22 may be referred to as knuckles. In one example, the pillows may, directly and/or indirectly, comprise a liquid composition, when present, on and/or in the fibrous structure 10 so that when a user contacts a surface to be treated, for example cleaned, with the fibrous structure 10, the liquid composition present in one or more pillows (macro protrusions 16) contacts the surface to be treated.

"Protruding surface" or "Macro protrusion surface" 14 as used herein, in one example, means the surface of the fibrous structure 10 having a maximum height greater than the maximum height of the fibrous structure surface 12 and/or greater than 60% and/or greater than 70% and/or greater than 85% and/or greater than 90% and/or greater than 95% and/or greater than 98% but less than 100% of the maximum height of the fibrous structure 10 as measured according to the MikroCAD Test Method described herein as shown in FIGS. 5A-5E. As shown in FIG. 5A-5E, an example of a fibrous structure 10 according to the present invention (as represented in the MikroCAD Images and corresponding MikroCAD Profiles) comprises a protruding surface (macro protrusion surface 14), in other words, the surface at greater than 60% and/or greater than 70% and/or greater than 85% and/or greater than 90% and/or greater than 95% and/or greater than 98% but less than 100% of the maximum height (referred to as "PS" in FIG. 5C).

"Contact surface" or "Micro protrusion surface" 18 as used herein, in one example, means the surface of a fibrous structure 10 having a height greater than the maximum height of at least one of the one or more protruding surfaces (macro protrusion surfaces 14) and/or the total protruding surface (total macro protrusion surface 14) and/or greater than 90% and/or greater than 92% and/or greater than 95% and/or greater than 98% and/or greater than 99% and/or up to 100% of the maximum height of the fibrous structure 10 as measured according to the MikroCAD Test Method described herein as shown in FIGS. 5A-5E. As shown in FIGS. 4A-4C, 5A-5E, and 6A-6B, an example of a fibrous structure 10 according to the present invention (as represented in the MikroCAD Images and corresponding MikroCAD Profiles) comprises a fibrous structure surface 12 comprising one or more macro protrusions 16 forming one or more protruding surfaces (macro protrusion surfaces 14), wherein at least one of the protruding surfaces (macro protrusion surfaces 14) comprises one or more contact surface protrusions (micro protrusions 20) that form one or more contact surfaces (micro protrusion surfaces 18) of the fibrous structure 10. In one example, a plurality of contact surface protrusions (micro protrusions 20) may be arranged in a contact surface pattern (micro protrusion surface pattern), for example a non-random pattern.

In other words, as shown in FIGS. 4A-4C and FIGS. 6A-6B, the contact surface (micro protrusion surface 18) is that surface formed by the fibrous structure 10 including any liquid composition present directly and/or indirectly on the fibrous structure 10 that contacts a surface to be treated, for example cleaned, when used by a user of the fibrous structure 10. For example, the contact surface (micro protrusion surface 18) is that surface formed by the fibrous structure 10 including any liquid composition present directly and/or indirectly on the surface of the fibrous structure 10 that contacts a user's floor when a user cleans his/her floor with a fibrous structure, for example a floor cleaning pad, according to the present invention.

The protruding surface (macro protrusion surface 14) may comprise one or more contact surface protrusions micro protrusions 20) relative to the plane $P_P$ (the protruding surface plane (macro protrusion surface plane)). The protruding surface (macro protrusion surface 14) may further comprise one or more non-raised and/or recessed regions 22 relative to the plane $P_P$ of the protruding surface (macro protrusion surface 14). In one example, one or more contact surface protrusions (micro protrusions 20) may be referred to as micro pillows and one or more non-raised and/or recessed regions 22 may be referred to as knuckles.

The contact surface (micro protrusion surface 18) may be present on the fibrous structure 10 before use by the user and/or it may be created/formed prior to and/or during use of the fibrous structure 10 by the user, such as upon the user applying pressure to the fibrous structure 10 as the user contacts a surface to be treated/cleaned with the fibrous structure 10, for example a floor cleaning pad. In one example, the contact surface (micro protrusion surface 18) along with its contact surface protrusions (micro protrusions 20) are present on the fibrous structure 10 prior to use by the user. In another example, the contact surface (micro protrusion surface 18) along with its contact surface protrusions (micro protrusions 20) are formed into the fibrous structure 10 during the making of the fibrous structure 10.

In one example, one or more of the contact surface protrusions (micro protrusions 20) may be present on the protruding surface (macro protrusion surface 14) such that at least one of the contact surface protrusions (micro protrusions 20) exhibits an average absolute surface height value (Sa) of greater than 250 μm and/or greater than 500 μm and/or greater than 750 μm and/or greater than 900 μm and/or greater than 1000 μm and/or greater than 1250 μm and/or greater than 1500 μm and/or greater than 2000 μm and/or greater than 2500 μm as measured according to the MikroCAD Test Method.

The contact surface protrusion (micro protrusion 20) may be void of pin holes.

A contact surface protrusion (micro protrusion 20) may be in the form of a continuous network contact surface protrusion (continuous network micro protrusion 20).

Two or more contact surface protrusions (micro protrusions 20) may be in the form of semi-continuous contact surface protrusions (semi-continuous micro protrusions 20).

Two or more contact surface protrusions (micro protrusions 20) may be in the form of discrete contact surface protrusions (discrete micro protrusions 20).

In one example, two or more contact surface protrusions (micro protrusions 20) are in the form of one or more of the following:
 a. a continuous network contact surface protrusion (continuous network micro protrusion 20),
 b. semi-continuous contact surface protrusions (semi-continuous micro protrusions 20); and
 c. discrete contact surface protrusions (discrete micro protrusions 20).

A plurality of contact surface protrusions (micro protrusions 20) may be in the form of discrete contact surface protrusions (discrete micro protrusions 20) arranged in a macro surface pattern on a protruding surface (macro protrusion surface 14).

In another example, at least one contact surface protrusion (micro protrusion 20) is in the form of a continuous network contact surface protrusion (continuous network micro protrusion 20) arranged in a macro surface pattern on a protruding surface (macro protrusion surface 14).

In still another example, two or more of the contact surface protrusions (micro protrusions 20) may be arranged in a non-random, repeating pattern.

In one example, one or more contact surfaces (micro protrusion surfaces 18) may comprise a scrim component as described herein. For example, one or more contact surfaces (micro protrusion surfaces 18) may comprise a plurality of fibrous elements, for example filaments, that exhibit a diameter of less than 20 µm and/or less than 15 µm and/or less than 12 µm and/or less than 10 µm and/or less than 8 µm and/or greater than 1 µm and/or greater than 3 µm and/or from about 3 µm to about 6 µm as measured according to the Diameter Test Method described herein. In another example, the scrim component may be present on a contact surface (micro protrusion surface 18) at a basis weight of greater than 0.5 gsm and/or greater than 1 gsm and/or greater than 1.5 gsm and/or greater than 2 gsm and/or less than 16 gsm and/or less than 10 gsm and/or less than 8 gsm and/or less than 6 gsm and/or less than 4 gsm and/or less than 3 gsm and/or from about 2 gsm to about 10 gsm and/or from about 4 gsm to about 8 gsm as measured according to the Fibrous Structure Basis Weight Test Method described herein. In one example, the scrim component comprises meltblown fibrous elements, for example meltblown filaments.

In one example, one or more protruding surfaces (macro protrusion surfaces 14) may comprise a scrim component as described herein. For example, one or more protruding surfaces (macro protrusion surfaces 14) may comprise a plurality of fibrous elements, for example filaments, that exhibit a diameter of less than 20 µm and/or less than 15 µm and/or less than 12 µm and/or less than 10 µm and/or less than 8 µm and/or greater than 1 µm and/or greater than 3 µm and/or from about 3 µm to about 6 µm as measured according to the Diameter Test Method described herein. In another example, the scrim component may be present on a protruding surface (macro protrusion surface 14) at a basis weight of greater than 0.5 gsm and/or greater than 1 gsm and/or greater than 1.5 gsm and/or greater less than 10 gsm and/or less than 8 gsm and/or less than 6 gsm and/or less than 4 gsm and/or less than 3 gsm and/or from about 1 gsm to about 3 gsm as measured according to the Fibrous Structure Basis Weight Test Method described herein. In one example, the scrim component comprises meltblown fibrous elements, for example meltblown filaments.

In one example, the fibrous structure surface 12 may comprise a scrim component as described herein. For example, the fibrous surface 12 may comprise a plurality of fibrous elements, for example filaments, that exhibit a diameter of less than 20 µm and/or less than 15 µm and/or less than 12 µm and/or less than 10 µm and/or less than 8 µm and/or greater than 1 µm and/or greater than 3 µm and/or from about 3 µm to about 6 µm as measured according to the Diameter Test Method described herein. In another example, the scrim component may be present on the fibrous structure surface 12 at a basis weight of greater than 0.5 gsm and/or greater than 1 gsm and/or greater than 1.5 gsm and/or greater less than 10 gsm and/or less than 8 gsm and/or less than 6 gsm and/or less than 4 gsm and/or less than 3 gsm and/or from about 1 gsm to about 3 gsm as measured according to the Fibrous Structure Basis Weight Test Method described herein. In one example, the scrim component comprises meltblown fibrous elements, for example meltblown filaments.

In one example, the fibrous structure 10 of the present invention may comprise scrim component that is present on two or more and/or three or more of the surfaces (fibrous structure surface 12, protruding surfaces (macro protrusion surfaces 14), and contact surfaces (micro protrusion surfaces 18)) of the fibrous structure 10.

"Fibrous structure surface 12 surface area" as used herein means the total area of the fibrous structure surface 12 of a fibrous structure 10 as shown in FIGS. 4A-4C. In other words, as shown in FIGS. 4A-4C, the fibrous structure surface 12 surface area of a fibrous structure 10 is the area calculated from the respective dimensions (in the same units) of the fibrous structure surface 12 of the fibrous structure 10, for example by multiplying the fibrous structure surface's width $W_F$ by the fibrous structure surface's length $L_F$ (in the same units).

"Protruding surface surface area" or "Macro protrusion surface 14 surface area" as used herein means the total area of one or more and/or all of the protruding surfaces (macro protrusion surfaces 14) of a fibrous structure 10 as shown in FIGS. 4A-4C. In other words as shown in FIGS. 4A-4C, the protruding surface surface area (macro protrusion surface 14 surface area) of a fibrous structure 10 is the area calculated from the respective dimensions (in the same units) of the one or more or all protruding surfaces (macro protrusion surfaces 14) of the fibrous structure 10, for example by multiplying the protruding surface's (macro protrusion surface's 14) width $W_P$ by the protruding surface's (macro protrusion surface's 14) length $L_P$ (in the same units).

"Contact surface surface area" or "Micro protrusion surface 18 surface area" as used herein means the total area of the contact surface (micro protrusion surface 18) of a fibrous structure 10 as shown in FIGS. 4A-4C. In other words, as shown in FIGS. 4A-4C, the contact surface surface area (micro protrusion surface 18 surface area) of a fibrous structure 10 is the area calculated from the respective dimensions (in the same units) of the contact surface (micro protrusion surface 18) of a fibrous structure 10, for example by multiplying the contact surface's (micro protrusion surface's 18) width by the contact surface's (micro protrusion surface's 18) length (in the same units).

In one example, the protruding surface surface area (macro protrusion surface 14 surface area) is less than the fibrous structure surface 12 surface area. In one example, the protruding surface surface area (macro protrusion surface 14 surface area) is greater than 50% to less than 98% and/or greater than 60% to less than 98% and/or greater than 70% to less than 95% and/or greater than 75% to less than 95% and/or from about 80% to about 90% of the fibrous structure surface 12 surface area.

In one example, the contact surface surface area (micro protrusion surface 18 surface area) is less than the fibrous structure surface 12 surface area. In one example, the contact surface surface area (micro protrusion surface 18 surface area) is greater than 50% to less than 98% and/or greater than 60% to less than 98% and/or greater than 70% to less than 95% and/or greater than 75% to less than 95% and/or from about 80% to about 90% of the fibrous structure surface 12 surface area.

In one example, the contact surface surface area (micro protrusion surface 18 surface area) is less than the protruding surface surface area (macro protrusion surface 14 surface area). In one example, the contact surface surface area (micro protrusion surface 18 surface area) is greater than 50% to less than 100% and/or greater than 50% to less than 99% and/or greater than 50% to less than 98% and/or greater than 60% to less than 98% and/or greater than 70% to less than 95% and/or greater than 75% to less than 95% and/or from about 80% to about 90% of the protruding surface surface area (macro protrusion surface 14 surface area).

In even another example, the protruding surface surface area (macro protrusion surface 14 surface area) is less than the fibrous structure surface 12 surface area and the contact surface surface area (micro protrusion surface 18 surface area) is less than the protruding surface surface area (macro protrusion surface 14 surface area). In one example, the protruding surface surface area (macro protrusion surface 14 surface area) is greater than 50% to less than 98% and/or greater than 60% to less than 98% and/or greater than 70% to less than 95% and/or greater than 75% to less than 95% and/or from about 80% to about 90% of the fibrous structure surface 12 surface area and the contact surface surface area (micro protrusion surface 18 surface area) is greater than 50% to less than 98% and/or greater than 60% to less than 98% and/or greater than 70% to less than 95% and/or greater than 75% to less than 95% and/or from about 80% to about 90% of the fibrous structure surface 12 surface area and/or the contact surface surface area (micro protrusion surface 18 surface area) is greater than 50% to less than 100% and/or greater than 50% to less than 99% and/or greater than 50% to less than 98% and/or greater than 60% to less than 98% and/or greater than 70% to less than 95% and/or greater than 75% to less than 95% and/or from about 80% to about 90% of the protruding surface surface area (macro protrusion surface 14 surface area).

In one example of the present invention, the surfaces of the fibrous structure, namely, the fibrous structure's surface 12, and the contact surface (micro protrusion surface 18), and optionally protruding surface (macro protrusion surface 14), are arranged on the fibrous structure 10 such that the fibrous structure 10, for example pre-moistened fibrous structure, exhibits greater than 50% and/or greater than 60% and/or greater than 70% and/or greater than 80% and/or to 100% and/or less than 98% and/or less than 95% soil coverage.

"Solid additive" as used herein means a pulp fiber and/or a particulate.

"Particulate" as used herein means a granular substance or powder. In one example, the particulate comprises superabsorbent material particles.

"Filament" as used herein means an elongate particulate having an apparent length greatly exceeding its apparent width, i.e. a length to diameter ratio of at least about 10. A filament is made via spinning, for example via meltblowing and/or spunbonding, from a polymer, for example a thermoplastic polymer, such as polyolefin, for example polypropylene and/or polyethylene, and propylene copolymers, ethylene copolymers, and mixtures thereof, and/or polyester. A filament" is an elongate particulate as described above that exhibits a length of greater than or equal to 5.08 cm (2 in.). Filaments are typically considered continuous or substantially continuous in nature. Non-limiting examples of filaments include meltblown and/or spunbond filaments. Non-limiting examples of materials that can be spun into filaments include thermoplastic polymer filaments, such as polyesters, nylons, polyolefins such as polypropylene filaments and polyethylene filaments, and biodegradable or compostable thermoplastic fibers such as polylactic acid filaments, polyhydroxyalkanoate filaments, polycaprolactone filaments, and polyhydroxybutyrate filaments. The filaments may be monocomponent or multicomponent, such as bicomponent filaments.

"Pulp fibers" as used herein means fibers that have been derived from vegetative sources, such as plants and/or trees. In one example of the present invention, "pulp fiber" refers to papermaking fibers. Papermaking fibers useful in the present invention include cellulosic pulp fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood pulp fibers can be blended, or alternatively, can be deposited in layers to provide a stratified web. U.S. Pat. Nos. 4,300,981 and 3,994,771 are incorporated herein by reference for the purpose of disclosing layering of hardwood and softwood pulp fibers. Also applicable to the present invention are pulp fibers derived from recycled paper, which may contain any or all of the above categories as well as other non-fibrous materials such as fillers and adhesives used to facilitate the original papermaking.

In addition to the various wood pulp fibers, other pulp fibers such as cotton linters, trichomes, seed hairs, rice straw, wheat straw, bamboo, and bagasse can be used in this invention.

"Distinct from" and/or different from" as used herein means two things that exhibit different properties and/or levels of materials, for example different by 0.5 and/or 1 and/or 2 and/or 3 and/or 5 and/or 10 units and/or different by 1% and/or 3% and/or 5% and/or 10% and/or 20%, different materials, and/or different fibrous element, for example filament, diameters.

"Textured pattern" as used herein means a pattern, for example a surface pattern, such as a three-dimensional (3D) surface pattern present on a surface of the fibrous structure and/or on a surface of a component making up the fibrous structure, for example a protruding surface (macro protrusion surface) and/or a contact surface (micro protrusion surface).

"Fibrous Structure Basis Weight" as used herein is the weight per unit area of a sample reported in lbs/3000 ft$^2$ or g/m$^2$ and is measured according to the Fibrous Structure Basis Weight Test Method described herein.

"Ply" as used herein means an individual, integral fibrous structure.

"Plies" as used herein means two or more individual, integral fibrous structures disposed in a substantially contiguous, face-to-face relationship with one another, forming a multi-ply fibrous structure product, such as a multi-ply cleaning pad. It is also contemplated that an individual, integral fibrous structure can effectively form a multi-ply fibrous structure product, such as a multi-ply cleaning pad, for example, by being folded on itself.

"Machine Direction" or "MD" as used herein means the direction parallel to the flow of the fibrous structure through the fibrous structure making machine and/or manufacturing equipment.

"Cross Machine Direction" or "CD" as used herein means the direction parallel to the width of the fibrous structure through the fibrous structure making machine and/or manufacturing equipment and perpendicular to the machine direction.

"Common Intensive Property" as used herein means an intensive property possessed by more than one region within a fibrous structure. Such intensive properties of the fibrous structure include, without limitation, density, basis weight, thickness, and combinations thereof. For example, if density is a common intensive property of two or more different regions, a value of the density in one region can differ from a value of the density in one or more other regions. Regions (such as, for example, a first region and a second region and/or a continuous network region and at least one of a plurality of discrete zones) are identifiable areas visually discernible and/or visually distinguishable from one another by distinct intensive properties.

"X," "Y," and "Z" designate a conventional system of Cartesian coordinates, wherein mutually perpendicular coordinates "X" and "Y" define a reference X-Y plane, and "Z" defines an orthogonal to the X-Y plane. "Z-direction" designates any direction perpendicular to the X-Y plane. Analogously, the term "Z-dimension" means a dimension, distance, or parameter measured parallel to the Z-direction. When an element, such as, for example, a molding member curves or otherwise deplanes, the X-Y plane follows the configuration of the element.

"Substantially continuous" or "continuous" region refers to an area within which one can connect any two points by an uninterrupted line running entirely within that area throughout the line's length. That is, the substantially continuous region has a substantial "continuity" in all directions parallel to the first plane and is terminated only at edges of that region. The term "substantially," in conjunction with continuous, is intended to indicate that while an absolute continuity is preferred, minor deviations from the absolute continuity may be tolerable as long as those deviations do not appreciably affect the performance of the fibrous structure (or a molding member) as designed and intended.

"Substantially semi-continuous" or "semi-continuous" region refers an area which has "continuity" in all, but at least one, directions parallel to the first plane, and in which area one cannot connect any two points by an uninterrupted line running entirely within that area throughout the line's length. The semi-continuous framework may have continuity only in one direction parallel to the first plane. By analogy with the continuous region, described above, while an absolute continuity in all, but at least one, directions is preferred, minor deviations from such a continuity may be tolerable as long as those deviations do not appreciably affect the performance of the fibrous structure.

"Discontinuous" or "discrete" regions or zones refer to discrete, and separated from one another areas or zones that are discontinuous in all directions parallel to the first plane.

"Molding member" is a structural element that can be used as a support for the mixture of filaments and solid additives that can be deposited thereon during a process of making a fibrous structure, and as a forming unit to form (or "mold") a desired microscopical geometry of a fibrous structure. The molding member may comprise any element that has the ability to impart a three-dimensional pattern to the fibrous structure being produced thereon, and includes, without limitation, a stationary plate, a belt, a cylinder/roll, a woven fabric, and a band.

"Meltblowing" is a process for producing filaments directly from polymers or resins using high-velocity air or another appropriate force to attenuate the filaments before collecting the filaments on a collection device, such as a belt, for example a patterned belt or molding member. In a meltblowing process the attenuation force is applied in the form of high speed air as the material (polymer) exits a die or spinnerette.

"Spunbonding" is a process for producing filaments directly from polymers by allowing the polymer to exit a die or spinnerette and drop a predetermined distance under the forces of flow and gravity and then applying a force via high velocity air or another appropriate source to draw and/or attenuate the polymer into a filament.

"Stack" as used herein, refers to a neat pile of fibrous structures and/or wipes. Based upon the assumption that there are at least three wipes in a stack, each wipe, except for the topmost and bottommost wipes in the stack, will be directly in face to face contact with the wipe directly above and below itself in the stack. Moreover, when viewed from above, the wipes will be layered on top of each other, or superimposed, such that only the topmost wipe of the stack will be visible. The height of the stack is measured from the bottom of the bottommost wipe in the stack to the top of the topmost wipe in the stack and is provided in units of millimeters (mm).

"Liquid composition" and "lotion" are used interchangeably herein and refer to any liquid, including, but not limited to a pure liquid such as water, an aqueous solution, a colloid, an emulsion, a suspension, a solution and mixtures thereof. The term "aqueous solution" as used herein, refers to a solution that is at least about 20% and/or at least about 40% and/or at least about 50% water by weight, and is no more than 99.9% and/or no more than about 99% and/or no more than about 98% and/or no more than about 97% and/or no more than about 95% and/or no more than about 90% water by weight.

In one example, the liquid composition comprises water or another liquid solvent. Generally, the liquid composition is of sufficiently low viscosity to impregnate the entire structure of the fibrous structure. In another example, the liquid composition may be primarily present at the fibrous structure surface and to a lesser extent in the inner structure of the fibrous structure. In a further example, the liquid composition is releasably carried by the fibrous structure, that is the liquid composition is carried on or in the fibrous structure and is readily releasable from the fibrous structure by applying some force to the fibrous structure, for example by wiping a surface with the fibrous structure.

The liquid compositions used in the present invention are primarily although not limited to, oil in water emulsions. In one example, the liquid composition of the present invention comprises at least 80% and/or at least 85% and/or at least 90% and/or at least 95% by weight water.

When present on or in the fibrous structure, the liquid composition may be present at a level of from about 10% to about 1000% of the basis weight of the fibrous structure and/or from about 100% to about 700% of the basis weight of the fibrous structure and/or from about 200% to about 500% and/or from about 200% to about 400% of the basis weight of the fibrous structure.

The liquid composition may comprise an acid. Non-limiting examples of acids that can be used in the liquid composition of the present invention are adipic acid, tartaric acid, citric acid, maleic acid, malic acid, succinic acid, glycolic acid, glutaric acid, malonic acid, salicylic acid, gluconic acid, polymeric acids, phosphoric acid, carbonic acid, fumaric acid and phthalic acid and mixtures thereof. Suitable polymeric acids can include homopolymers, copolymers and terpolymers, and may contain at least 30 mole % carboxylic acid groups. Specific examples of suitable polymeric acids useful herein include straight-chain poly (acrylic) acid and its copolymers, both ionic and nonionic, (e.g., maleic-acrylic, sulfonic-acrylic, and styrene-acrylic copolymers), those cross-linked polyacrylic acids having a molecular weight of less than about 250,000, preferably less than about 100,000 poly (α-hydroxy) acids, poly (methacrylic) acid, and naturally occurring polymeric acids such as carageenic acid, carboxy methyl cellulose, and alginic acid. In one example, the liquid composition comprises citric acid and/or citric acid derivatives.

The liquid composition may also contain salts of the acid or acids used to lower the pH, or another weak base to impart buffering properties to the fibrous structure. The buffering response is due to the equilibrium which is set up between the free acid and its salt. This allows the fibrous structure to maintain its overall pH despite encountering a relatively high amount of bodily waste as would be found post urination or defecation in a baby or adult. In one embodiment the acid salt would be sodium citrate. The amount of sodium citrate present in the lotion would be between 0.01 and 2.0%, alternatively 0.1 and 1.25%, or alternatively 0.2 and 0.7% of the lotion.

In one example, the liquid composition does not contain any preservative compounds. In another example, the liquid composition does contain preservative compounds.

In addition to the above ingredients, the liquid composition may comprise additional ingredients. Non-limiting examples of additional ingredients that may be present in the liquid composition of the present invention include: skin conditioning agents (emollients, humectants) including, waxes such as petrolatum, cholesterol and cholesterol derivatives, di and tri-glycerides including sunflower oil and sesame oil, silicone oils such as dimethicone copolyol, caprylyl glycol and acetoglycerides such as lanolin and its derivatives, emulsifiers, stabilizers, surfactants including anionic, amphoteric, cationic and non ionic surfactants, colourants, chelating agents including EDTA, sun screen agents, solubilizing agents, perfumes, opacifying agents, vitamins, viscosity modifiers, such as xanthan gum, astringents and external analgesics.

In one example, the liquid composition comprises a surfactant, an acidifying agent, an amide, for example an amide of formula I:

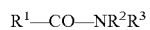
$$R^1\text{---CO---}NR^2R^3 \tag{I}$$

wherein $R^1$ is selected from the group consisting of linear or branched, substituted or unsubstituted $C_6$-$C_{12}$, each of $R^2$ and $R^3$ is independently selected from H, OH, a halogen, or $C_1$-$C_6$ linear or branched, substituted or unsubstituted hydrocarbyl groups; and water, wherein said composition has a pH from about 1.0 to about 6.0 and/or from about 2.5 to about 5.0. The liquid composition may comprise an antibacterial agent, for example from about 0.01% to about 30% of an antimicrobial active, such as an antimicrobial active selected from ionic silver, an active oxygen source, or mixtures thereof. In one example, the antimicrobial active is an active oxygen source, wherein the active oxygen source is hydrogen peroxide, and the active oxygen source is present at a level of from about 0.05% to about 8% by weight of the liquid composition. In one example, the antimicrobial active is an active oxygen source, wherein the active oxygen source is hydrogen peroxide and further comprises from 1 to about 50 ppm of $C_{6-10}$ fatty peracid.

In one example the liquid composition comprises from about 0.01% to about 60% by weight of said surfactant, from about 0.01% to about 40% and/or from about 0.03% to about 25% by weight of said acidifying agent, from about 0.01% to about 40% and/or from about 0.03% to about 25% by weight of said amide of formula I, and from about 15% to about 99.95% by weight of said water.

The surfactant within the liquid composition may be a $C_6$-$C_{12}$ surfactant. In one example, the surfactant may be selected from the group consisting of $C_8$ glyceryl ether sulfonate, $C_2$-$C_8$ linear alkyl benzene sulfonate, $C_6$-$C_{12}$ alkyl sulfate, $C_8$-$C_{12}$ methyl ester sulfonate, $C_8$-$C_{12}$ fatty acid sulfonate, $C_6$-$C_{12}$ alkylethoxy carboxylate, $C_6$-$C_{12}$ alkylethoxy sulfate, $C_{8-10}$ dimethyl amine oxide, $C_8$ pyrrolidone, $C_8$ dimethyl betaine, $C_{8-10}$ alkyl polyglycoside, $C_{8-12}$ N,N-dimethyl-3-ammonio-1-propanesulfonate, and mixtures thereof.

In one example, the acidifying agent is selected from the group consisting of formic acid, acetic acid, benzoic acid, malonic acid, citric acid, maleic acid, fumaric acid, hypochlorous acid, succinic acid, gluconic acid, glutaric acid, lactic acid, 2-ethyl-1-hexanoic acid, cinnamic acid, heptanoic acid, octanoic acid, nonanoic acid, peracetic acid, peroctanoic acid, undecylenic acid, and mixtures thereof.

In one example, the amide of formula I is selected from the group consisting of N,N-dimethyl octanamide, N,N-dimethyl decanamide, N,N-dimethyl 9-decenamide, N,N-dimethyl 7-octenamide, octanohydroxamic acid, and mixtures thereof.

In one example, when present, the surfactant and the antimicrobial active, for example hydrogen peroxide, are present in the liquid composition at a weight ratio of surfactant to antimicrobial active of from about 0.1:1 to about 10:1.

In one example, when present, the acidifying agent and the antimicrobial active, for example hydrogen peroxide, of from about 0.2:1 to about 5:1.

In one example, when present, the amide of formula I, for example the amide of formula I wherein $R^1$ is selected from the group consisting of linear or branched, substituted or unsubstituted $C_6$-$C_{10}$ hydrocarbyl groups, and the antimicrobial active, for example hydrogen peroxide, are present in the liquid composition at a weight ratio of antimicrobial active to the amide of formula I of from about 0.2:1 to about 5:1.

In one example, the liquid composition may further comprise a solvent, for example a solvent selected from the group consisting of ethanol, isopropanol, $C_1$-$C_8$ monoethylene glycol ether, $C_1$-$C_8$ diethylene glycol ether, $C_1$-$C_8$ triethylene glycol ether, $C_1$-$C_6$ monopropylene glycol ether, $C_1$-$C_6$ dipropylene glycol ether, $C_1$-$C_6$ tripropylene glycol ether, $C_1$-$C_6$ esters of formic acid, $C_1$-$C_6$ esters of acetic acid, $C_1$-$C_6$ esters of benzoic acid, $C_1$-$C_6$ esters of lactic acid, $C_1$-$C_6$ esters of 3-hydroxybutyric acid, $C_1$-$C_6$ amines, $C_1$-$C_6$ alkanol amines, and mixtures thereof.

The liquid composition may exhibit a critical micelle concentration from about 100 ppm to about 2,500 ppm.

"Pre-moistened" and "wet" are used interchangeably herein and refer to fibrous structures and/or wipes which are moistened with a liquid composition prior to packaging in a generally moisture impervious container or wrapper. Such pre-moistened wipes, which can also be referred to as "wet wipes" and "towelettes", may be suitable for use in cleaning babies, as well as older children and adults.

"Saturation loading" and "lotion loading" are used interchangeably herein and refer to the amount of liquid composition applied to the fibrous structure or wipe. In general, the amount of liquid composition applied may be chosen in order to provide maximum benefits to the end product comprised by the wipe. Saturation loading is typically expressed as grams of liquid composition per gram of dry wipe.

Saturation loading, often expressed as percent saturation, is defined as the percentage of the dry fibrous structure or wipe's mass (void of any liquid composition) that a liquid composition present on/in the fibrous structure or wipe represents. For example, a saturation loading of 1.0 (equivalently, 100% saturation) indicates that the mass of liquid composition present on/in the fibrous structure or wipe is equal to the mass of dry fibrous structure or wipe (void of any liquid composition).

The following equation is used to calculate saturation load of a fibrous structure or wipe:

$$\text{Saturation Loading} = \left[\frac{\text{wet wipe mass}}{(\text{wipe size}) * (\text{basis weight})}\right] - 1$$

"Saturation gradient index" (SGI) is a measure of how well the wipes at the top of a stack retain moisture. The SGI of a stack of wipes is measured as described infra and is calculated as the ratio of the average lotion load of the bottommost wipes in the stack versus the topmost wipes in the stack. The ideal stack of wipes will have an SGI of about 1.0, that is, the topmost wipes will be equally as moist as the bottommost wipes. In the aforementioned embodiments, the stacks have a SGI from about 1.0 to about 1.5.

The saturation gradient index for a fibrous structure or wipe stack is calculated as the ratio of the saturation loading of a set number of fibrous structures or wipes from the bottom of a stack to that of the same number of fibrous structures or wipes from the top of the stack. For example, for an approximately 80 count wipe stack, the saturation gradient index is this ratio using 10 wipes from bottom and top, for an approximately 30 count wipe stack, 5 wipes from bottom and top are used; and for less than 30, only the top and bottom single wipes are used in the saturation gradient index calculation. The following equation illustrates the example of an 80 count stack saturation gradient index calculation:

$$\text{Saturation Gradient Index} = \frac{\text{average lotion load of bottom 10 wipes in stack}}{\text{average lotion load of top 10 wipes in stack}}$$

A saturation profile, or wetness gradient, exists in the stack when the saturation gradient index is greater than 1.0. In cases where the saturation gradient index is significantly greater than 1.0, e.g. over about 1.5, lotion is draining from the top of the stack and settling in the bottom of the container, such that there may be a noticeable difference in the wetness of the topmost fibrous structures or wipes in the stack compared to that of the fibrous structures or wipes nearest the bottom of the stack. For example, a perfect tub of wipes would have a saturation gradient index of 1.0, the bottommost wipes and topmost wipes would maintain equivalent saturation loading during storage. Additional liquid composition would not be needed to supersaturate the wipes in an effort to keep all of the wipes moist, which typically results in the bottommost wipes being soggy.

"Percent moisture" or "% moisture" or "moisture level" as used herein means 100×(the ratio of the mass of water contained in a fibrous structure to the mass of the fibrous structure). The product of the above equation is reported as a %.

"Surface tension" as used herein, refers to the force at the interface between a liquid composition and air. Surface tension is typically expressed in dynes per centimeter (dynes/cm).

"Surfactant" as used herein, refers to materials which preferably orient toward an interface. Surfactants include the various surfactants known in the art, including: nonionic surfactants, anionic surfactants, cationic surfactants, amphoteric surfactants, zwitterionic surfactants; and mixtures thereof.

"Visually Discernible" as used herein, refers to being capable of being seen by the naked eye when viewed at a distance of 12 inches (in), or 30.48 centimeters (cm), under the unimpeded light of an ordinary incandescent 60 watt light bulb that is inserted in a fixture such as a table lamp. It follows that "visually discernible" as used herein refers to those features of fibrous structures, whether or not they are pre-moistened, that are readily visually discernible when the wipe is subjected to normal use, such as the cleaning of a child's skin.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Fibrous Structures

In one example, the fibrous structures of the present invention comprise a plurality of filaments and a plurality of solid additives. The filaments and the solid additives may be commingled together. In one example, the fibrous structure is a coform fibrous structure comprising filaments and solid additives. The filaments may be present in the fibrous structures of the present invention at a level of less than 90% and/or less than 80% and/or less than 65% and/or less than 50% and/or greater than 5% and/or greater than 10% and/or greater than 20% and/or from about 10% to about 50% and/or from about 25% to about 45% by weight of the fibrous structure on a dry basis.

The solid additives may be present in the fibrous structures of the present invention at a level of greater than 10% and/or greater than 25% and/or greater than 50% and/or less than 100% and/or less than 95% and/or less than 90% and/or less than 85% and/or from about 30% to about 95% and/or from about 50% to about 85% by weight of the fibrous structure on a dry basis.

The filaments and solid additives may be present in the fibrous structures of the present invention at a weight ratio of filaments to solid additive of greater than 10:90 and/or greater than 20:80 and/or less than 90:10 and/or less than 80:20 and/or from about 25:75 to about 50:50 and/or from about 30:70 to about 45:55. In one example, the filaments and solid additives are present in the fibrous structures of the present invention at a weight ratio of filaments to solid additives of greater than 0 but less than 1.

The fibrous structure core component may be a co-formed fibrous structure, wherein the fibrous structure core component filaments and fibrous structure core component solid additives are commingled together.

The fibrous structure core components may be compositionally and physically the same as the filaments of the scrim component herein.

In one example, the fibrous structures of the present invention exhibit a basis weight of from about 10 gsm to about 1000 gsm and/or from about 10 gsm to about 500 gsm and/or from about 15 gsm to about 400 gsm and/or from about 15 gsm to about 300 gsm as measured according to the Fibrous Structure Basis Weight Test Method described herein. In another example, the fibrous structures of the present invention exhibit a basis weight of from about 10 gsm to about 200 gsm and/or from about 20 gsm to about 150 gsm and/or from about 25 gsm to about 125 gsm and/or from about 30 gsm to about 100 gsm and/or from about 30 gsm to about 80 gsm as measured according to the Fibrous Structure Basis Weight Test Method described herein. In still another example, the fibrous structures of the present invention exhibit a basis weight of from about 80 gsm to about 1000 gsm and/or from about 125 gsm to about 800 gsm and/or from about 150 gsm to about 500 gsm and/or from about 150 gsm to about 300 gsm as measured according to the Fibrous Structure Basis Weight Test Method described herein.

Figure 6A:
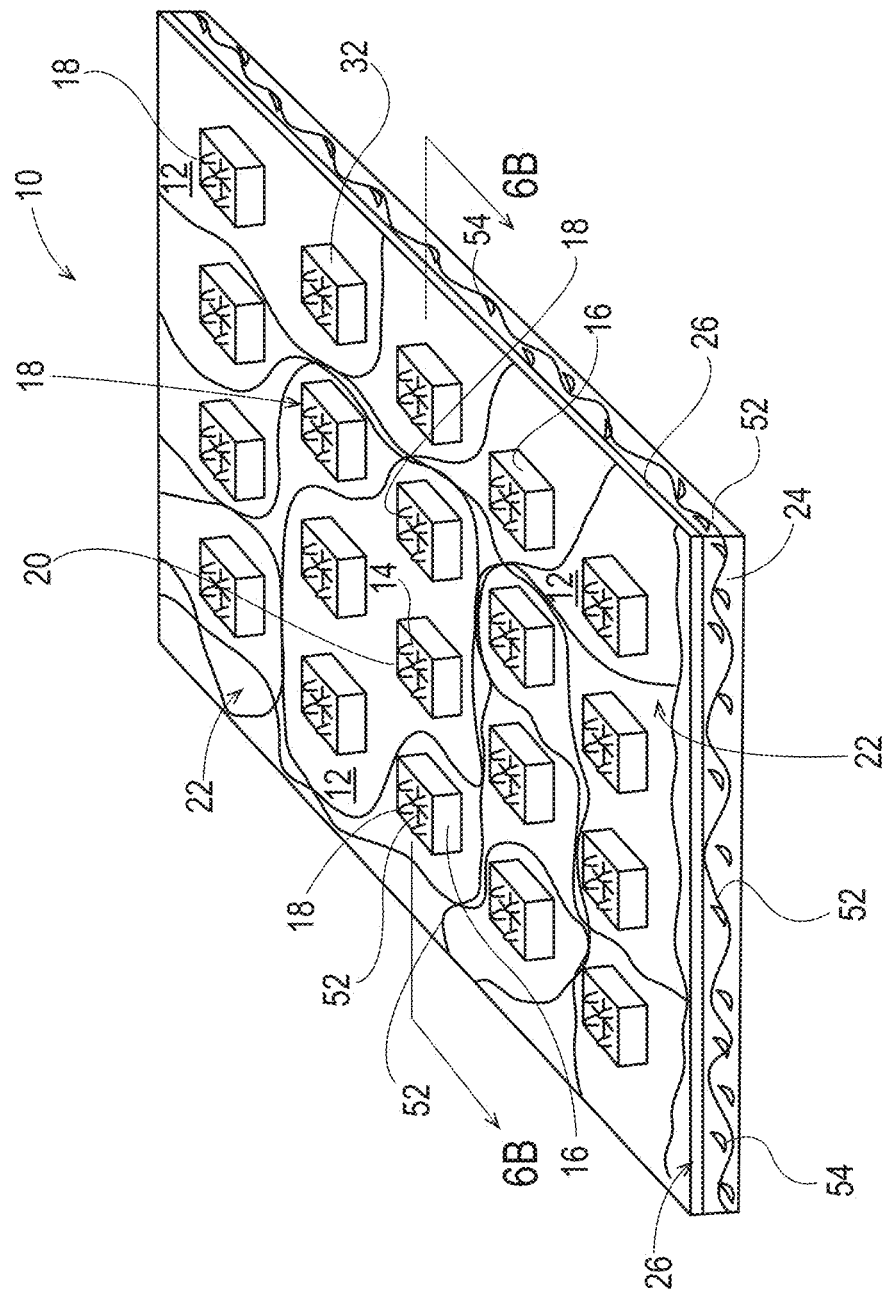
FIG. 6A is a perspective view of another example of a fibrous structure according to the present invention.
Figure 6B:
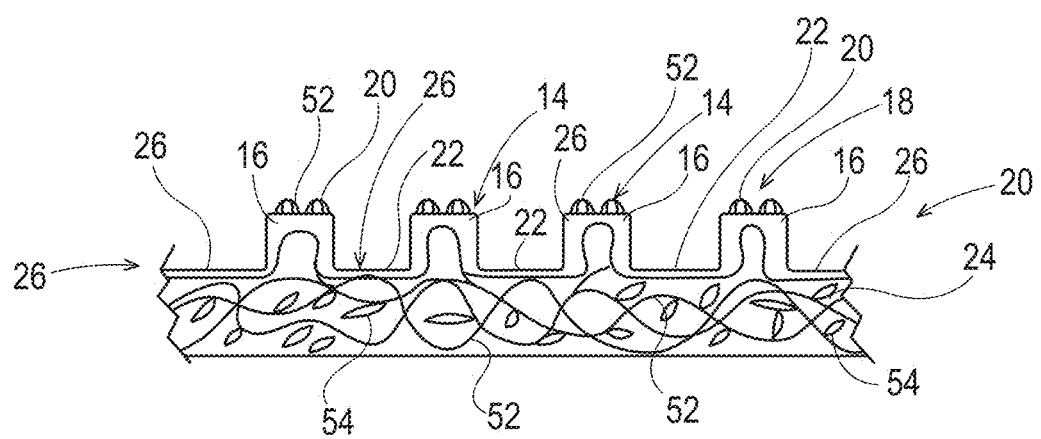
FIG. 6B is a cross-sectional view of the fibrous structure of FIG. 6A taken along line 6B-6B.

In one example, as shown in FIGS. 6A and 6B, the fibrous structure 10 of the present invention may comprise a core component 24. A "core component" as used herein means a fibrous structure 10 comprising a plurality of filaments and optionally a plurality of solid additives, wherein the fibrous structure 10 comprises at least one interior surface not exposed to the external environment, such as not exposed to a surface to be cleaned. In one example, the core component is a coform fibrous structure comprising a plurality of filaments and a plurality of solid additives, for example pulp fibers. In one example, the core component 24 is the component that exhibits the greatest basis weight with the fibrous structure 10 of the present invention. In one example, the total core components present in the fibrous structures of the present invention exhibit a basis weight that is greater than 50% and/or greater than 55% and/or greater than 60% and/or greater than 65% and/or greater than 70% and/or less than 100% and/or less than 95% and/or less than 90% of the total basis weight of the fibrous structure of the present invention as measured according to the Fibrous Structure Basis Weight Test Method described herein. In another example, the core component exhibits a basis weight of greater than 12 gsm and/or greater than 14 gsm and/or greater than 16 gsm and/or greater than 18 gsm and/or greater than 20 gsm and/or greater than 25 gsm as measured according to the Fibrous Structure Basis Weight Test Method described herein.

The fibrous structure of the present invention may comprise a fibrous structure core component comprising a plurality of filaments and a plurality of solid additives, for example fibers. In one example, the fibrous structure core component filaments are present in the fibrous structure core component at a level of less than 90% and/or greater than 5% and/or from about 10% to about 50% by weight of the fibrous structure on a dry basis. In one example, the fibrous structure core component solid additives, for example fibers, are present in the fibrous structure core component at a level of greater than 10% and/or greater than 25% and/or less than 100% and/or from about 30% to about 95% by weight of the fibrous structure on a dry basis. In another example, the fibrous structure core component filaments and the fibrous structure core component solid additives, for example fibers, are present in the fibrous structure core component at a weight ratio of fibrous structure core component filaments to fibrous structure core component solid additives, for example fibers, of greater than 2.5:97.5 and/or greater than 5:95 and/or greater than 10:90 and/or less than 90:10 and/or less than 50:50 and/or less than 40:60 and/or from about 15:85 to about 50:50 and/or greater than 0 but less than 1.

"Consolidated region" as used herein means a region within a fibrous structure where the filaments and optionally the solid additives have been compressed, compacted, and/or packed together with pressure and optionally heat (greater than 150° F.) to strengthen the region compared to the same region in its unconsolidated state or a separate region which did not see the compression or compacting pressure. In one example, a region is consolidated by forming unconsolidated regions within a fibrous structure on a patterned molding member and passing the unconsolidated regions within the fibrous structure while on the patterned molding member through a pressure nip, such as a heated metal anvil roll (about 275° F.) and a rubber anvil roll with pressure to compress the unconsolidated regions into one or more consolidated regions. In one example, the filaments present in the consolidated region, for example on the side of the fibrous structure that is contacted by the heated roll comprises fused filaments that create a skin on the surface of the fibrous structure, which may be visible via SEM images.

The fibrous structure 10 of the present invention may, in addition to a core component 24, further comprise a scrim component 26. "Scrim component" as used herein means a fibrous structure comprising a plurality of filaments that form at least one exterior surface, for example the scrim component 26 contacts a surface to be cleaned, of the fibrous structure 10 and is different from the core component 24. In one example, the total scrim components present in the fibrous structures of the present invention exhibit a basis weight that is less than 25% and/or less than 20% and/or less than 15% and/or less than 10% and/or less than 7% and/or less than 5% and/or greater than 0% and/or greater than 1% of the total basis weight of the fibrous structure of the present invention as measured according to the Fibrous Structure Basis Weight Test Method described herein. In another example, the scrim component exhibits a basis weight of 10 gsm or less and/or less than 10 gsm and/or less than 8 gsm and/or less than 6 gsm and/or greater than 5 gsm and/or less than 4 gsm and/or greater than 0 gsm and/or greater than 1 gsm as measured according to the Fibrous Structure Basis Weight Test Method described herein. In one example, the scrim component is void of pulp fibers.

A scrubby component (not shown) may also be included in the fibrous structure of the present invention. "Scrubby component" as used herein means that part of the fibrous structure of the present invention that imparts the scrubby quality to the fibrous structure. The scrubby component is distinct and different from the core and scrim components even though the scrubby component may be present in and/or on the core and scrim components. The scrubby component may be a feature, such as a pattern, for example a surface pattern, or texture that causes the fibrous structure to exhibit a scrubby property during use by a consumer. In another example, the scrubby component may be a material, for example a coarse filament (exhibits a greater average diameter than the majority of filaments within the core and/or scrim components). In one example, the scrubby component is a fibrous structure comprising a plurality of filaments. In one example, the total scrubby components present in the fibrous structures of the present invention exhibit a basis weight that is less than 25% and/or less than 20% and/or less than 15% and/or less than 10% and/or less than 7% and/or less than 5% and/or greater than 0% and/or greater than 1% of the total basis weight of the fibrous structure of the present invention as measured according to the Fibrous Structure Basis Weight Test Method described herein. In another example, the scrubby component exhibits a basis weight of 10 gsm or less and/or less than 10 gsm and/or less than 8 gsm and/or less than 6 gsm and/or greater than 5 gsm and/or less than 4 gsm and/or greater than 0 gsm and/or greater than 1 gsm as measured according to the Fibrous Structure Basis Weight Test Method described herein.

In one example, at least one of the core components of the fibrous structure comprises a plurality of solid additives, for example pulp fibers, such as comprise wood pulp fibers and/or non-wood pulp fibers.

In one example, at least one of the core components of the fibrous structure comprises a plurality of core filaments. In another example, at least one of the core components comprises a plurality of solid additives and a plurality of the core filaments. In one example, the solid additives and the core filaments are present in a layered orientation within the core component. In one example, the core filaments are present as a layer between two solid additive layers. In another example, the solid additives and the core filaments are present in a coform layer. At least one of the core filaments comprises a polymer, for example a thermoplastic polymer, such as a polyolefin. The polyolefin may be selected from the group consisting of: polypropylene, polyethylene, and mixtures thereof. In another example, the thermoplastic polymer of the core filament may comprise a polyester.

In one example, at least one of the core components comprises one or more scrubby components, for example a scrubby element, such as a scrubby filament. In one example, the scrubby filaments comprise a polymer, for example a thermoplastic polymer and/or hydroxyl polymer as described above with reference to the core components.

In one example, the scrubby filaments exhibit a diameter of less than 3 mm and/or less than 2 mm and/or less than 1 mm and/or less than 750 µm and/or less than 500 µm and/or less than 250 µm and/or greater than 50 µm and/or greater than 75 µm and/or greater than 100 µm as measured according to the Diameter Test Method described herein.

In one example, at least one of the scrim components is adjacent to at least one of the core components within the fibrous structure. In another example, at least one of the core components is positioned between two scrim components within the fibrous structure.

In one example, at least one of the scrim components of the fibrous structure of the present invention comprises a plurality of scrim filaments, for example scrim filaments, wherein the scrim filaments comprise a polymer, for example a thermoplastic and/or hydroxyl polymer as described above with reference to the core components.

In one example, at least one of the scrim filaments exhibits a diameter of less than 50 µm and/or less than 30 µm and/or less than 20 µm and/or less than 15 µm and/or less than 12 µm and/or less than 10 µm and/or less than 8 µm and/or less than 6 µm and/or at least 1 µm and/or greater than 1 µm and/or greater than 3 µm and/or from greater than 1 µm to less than 20 µm and/or from greater than 1 µm to less than 16 µm and/or from greater than 3 µm to less than 15 µm and/or from greater than 3 µm to less than 12 µm as measured according to the Diameter Test Method described herein.

In one example, at least one of the scrim components of the fibrous structures of the present invention comprises one or more scrubby components, for example a scrubby element, such as a scrubby filament. In one example, the scrubby filaments comprise a polymer, for example a thermoplastic polymer and/or hydroxyl polymer as described above with reference to the core components.

In one example, the scrubby filaments exhibit a diameter of less than 250 and/or less than 200 and/or less than 150 and/or less than 120 and/or less than 100 and/or 75 and/or less than 50 and/or less than 40 and/or less than 30 and/or less than 25 and/or greater than 0.6 and/or greater than 1 and/or greater than 3 and/or greater than 5 and/or greater than 10 µm as measured according to the Diameter Test Method described herein.

In another example, the scrubby element of the scrim component may comprise a pattern, for example a surface pattern, such as a textured pattern, present on a surface of the scrim component. The pattern may comprise a non-random, repeating pattern. The pattern may comprise a pattern molding member-imparted pattern.

The diameter of the core filaments is less than 250 and/or less than 200 and/or less than 150 and/or less than 100 and/or less than 50 and/or less than 30 and/or less than 25 and/or less than 10 and/or greater than 1 and/or greater than 3 µm as measured according to the Diameter Test Method described herein.

In one example, the fibrous structures of the present invention may comprise any suitable amount of filaments and any suitable amount of solid additives. For example, the fibrous structures may comprise from about 10% to about 70% and/or from about 20% to about 60% and/or from about 30% to about 50% by dry weight of the fibrous structure of filaments and from about 90% to about 30% and/or from about 80% to about 40% and/or from about 70% to about 50% by dry weight of the fibrous structure of solid additives, such as wood pulp fibers.

In one example, the filaments and solid additives of the present invention may be present in fibrous structures according to the present invention at weight ratios of filaments to solid additives of from at least about 1:1 and/or at least about 1:1.5 and/or at least about 1:2 and/or at least about 1:2.5 and/or at least about 1:3 and/or at least about 1:4 and/or at least about 1:5 and/or at least about 1:7 and/or at least about 1:10.

In one example, the solid additives, for example wood pulp fibers, may be selected from the group consisting of softwood kraft pulp fibers, hardwood pulp fibers, and mixtures thereof. Non-limiting examples of hardwood pulp fibers include fibers derived from a fiber source selected from the group consisting of: Acacia, Eucalyptus, Maple, Oak, Aspen, Birch, Cottonwood, Alder, Ash, Cherry, Elm, Hickory, Poplar, Gum, Walnut, Locust, Sycamore, Beech, Catalpa, Sassafras, Gmelina, Albizia, Anthocephalus, and Magnolia. Non-limiting examples of softwood pulp fibers include fibers derived from a fiber source selected from the group consisting of: Pine, Spruce, Fir, Tamarack, Hemlock, Cypress, and Cedar. In one example, the hardwood pulp fibers comprise tropical hardwood pulp fibers. Non-limiting examples of suitable tropical hardwood pulp fibers include Eucalyptus pulp fibers, Acacia pulp fibers, and mixtures thereof.

In one example, the wood pulp fibers comprise softwood pulp fibers derived from the kraft process and originating from southern climates, such as Southern Softwood Kraft (SSK) pulp fibers. In another example, the wood pulp fibers comprise softwood pulp fibers derived from the kraft process and originating from northern climates, such as Northern Softwood Kraft (NSK) pulp fibers.

The wood pulp fibers present in the fibrous structure may be present at a weight ratio of softwood pulp fibers to hardwood pulp fibers of from 100:0 and/or from 90:10 and/or from 86:14 and/or from 80:20 and/or from 75:25 and/or from 70:30 and/or from 60:40 and/or about 50:50 and/or to 0:100 and/or to 10:90 and/or to 14:86 and/or to 20:80 and/or to 25:75 and/or to 30:70 and/or to 40:60. In one example, the weight ratio of softwood pulp fibers to hardwood pulp fibers is from 86:14 to 70:30.

In one example, the fibrous structures of the present invention comprise one or more trichomes. Non-limiting examples of suitable sources for obtaining trichomes, especially trichome fibers, are plants in the Labiatae (Lamiaceae) family commonly referred to as the mint family. Examples of suitable species in the Labiatae family include *Stachys byzantina*, also known as *Stachys lanata* commonly referred to as lamb's ear, woolly betony, or woundwort. The term *Stachys byzantina* as used herein also includes cultivars *Stachys byzantina* 'Primrose Heron', *Stachys byzantina* 'Helene von Stein' (sometimes referred to as *Stachys byzantina* 'Big Ears'), *Stachys byzantina* 'Cotton Boll', *Stachys byzantina* 'Variegated' (sometimes referred to as *Stachys byzantina* 'Striped Phantom'), and *Stachys byzantina* 'Silver Carpet'.

In another example, the fibrous structure of the present invention, alone or as a ply of fibrous structure in a multi-ply fibrous structure, comprises a creped fibrous structure. The creped fibrous structure may comprise a fabric creped fibrous structure, a belt creped fibrous structure, and/or a cylinder creped, such as a cylindrical dryer creped fibrous structure. In one example, the fibrous structure may comprise undulations and/or a surface comprising undulations.

In yet another example, the fibrous structure of the present invention, alone or as a ply of fibrous structure in a multi-ply fibrous structure, comprises an uncreped fibrous structure.

In still another example, the fibrous structure of the present invention, alone or as a ply of fibrous structure in a multi-ply fibrous structure, comprises a foreshortened fibrous structure.

In another example of a fibrous structure in accordance with the present invention, instead of being layers of fibrous structure, the material forming layers may be in the form of plies wherein two or more of the plies may be combined to form a multi-ply fibrous structure. The plies may be bonded together, such as by thermal bonding and/or adhesive bonding, to form the multi-ply fibrous structure. After a bonding operation, especially a thermal bonding operation, it may be difficult to distinguish the plies of the fibrous structure and the fibrous structure may visually and/or physically be a similar to a layered fibrous structure in that one would have difficulty separating the once individual plies from each other.

The fibrous structures of the present invention and/or any fibrous structure products, for example cleaning pads, comprising such fibrous structures may be subjected to any post-processing operations such as embossing operations, printing operations, tuft-generating operations, thermal bonding operations, ultrasonic bonding operations, perforating operations, surface treatment operations such as application of lotions, silicones and/or other materials and mixtures thereof.

Non-limiting examples of suitable polypropylenes for making the filaments of the present invention are commercially available from Lyondell-Basell and Exxon-Mobil.

Any hydrophobic or non-hydrophilic materials within the fibrous structure, such as polypropylene filaments, may be surface treated and/or melt treated with a hydrophilic modifier. Non-limiting examples of surface treating hydrophilic modifiers include surfactants, such as Triton X-100. Non-limiting examples of melt treating hydrophilic modifiers that are added to the melt, such as the polypropylene melt, prior to spinning filaments, include hydrophilic modifying melt additives such as VW351 and/or S-1416 commercially available from Polyvel, Inc. and Irgasurf commercially available from Ciba. The hydrophilic modifier may be associated with the hydrophobic or non-hydrophilic material at any suitable level known in the art. In one example, the hydrophilic modifier is associated with the hydrophobic or non-hydrophilic material at a level of less than about 20% and/or less than about 15% and/or less than about 10% and/or less than about 5% and/or less than about 3% to about 0% by dry weight of the hydrophobic or non-hydrophilic material.

The fibrous structures of the present invention may include optional additives, each, when present, at individual levels of from about 0% and/or from about 0.01% and/or from about 0.1% and/or from about 1% and/or from about 2% to about 95% and/or to about 80% and/or to about 50% and/or to about 30% and/or to about 20% by dry weight of the fibrous structure. Non-limiting examples of optional additives include permanent wet strength agents, temporary wet strength agents, dry strength agents such as carboxymethylcellulose and/or starch, softening agents, lint reducing agents, opacity increasing agents, wetting agents, odor absorbing agents, perfumes, temperature indicating agents, color agents, dyes, osmotic materials, microbial growth detection agents, antibacterial agents, liquid compositions, surfactants, and mixtures thereof.

The fibrous structure of the present invention may itself be a fibrous structure product, for example a cleaning pad. It may be convolutedly wound about a core to form a roll. It may be combined with one or more other fibrous structures as a ply to form a multi-ply fibrous structure product, for example a multi-ply cleaning pad. In one example, a co-formed fibrous structure of the present invention may be convolutedly wound about a core to form a roll of co-formed fibrous structure product. The rolls of fibrous structure products may also be coreless.

The fibrous structures of the present invention may be pre-moistened, such as may comprise a liquid composition, wherein the fibrous structures exhibit mileage values of at least 135 ft$^2$/pre-moistened fibrous structure (floor cleaning pad) and/or at least 0.9 ft$^2$/gsm of the dry fibrous structure (dry floor cleaning pad) and/or at least 450 ft$^2$/ft$^2$ (at least 400 ft$^2$/ft$^2$ for a unitary, non-laminate, for example a pre-moistened fibrous structure that doesn't have a separate floor sheet attached thereto) of pre-moistened fibrous structure (floor cleaning pad) as measured according to the Mileage Test Method described herein.

In one example, a pre-moistened fibrous structure of the present invention exhibits a mileage value of at least 135 and/or greater than 140 and/or greater than 150 and/or greater than 170 and/or greater than 190 and/or greater than 210 and/or greater than 230 and/or greater than 250 ft$^2$/pre-moistened fibrous structure (floor cleaning pad) as measured according to the Mileage Test Method described herein. In another example, a pre-moistened fibrous structure of the present invention exhibits a mileage value of at least 165 and/or at least 190 and/or at least 220 and/or at least 260 ft²/pre-moistened fibrous structure (floor cleaning pad) as measured according to the Mileage Test Method described herein.

In another example, a pre-moistened fibrous structure of the present invention exhibits a mileage value of at least 0.9 and/or greater than 0.95 and/or greater than 1 and/or greater than 1.1 and/or greater than 1.2 and/or greater than 1.3 and/or greater than 1.4 ft²/gsm of the dry fibrous structure (dry floor cleaning pad) as measured according to the Mileage Test Method described herein. In another example, a pre-moistened fibrous structures of the present invention example exhibits a mileage value of at least 1.1 and/or at least 1.3 and/or at least 1.5 ft²/gsm of the dry fibrous structure as measured according to the Mileage Test Method described herein.

In another example, a pre-moistened fibrous structure of the present invention exhibits a mileage value of at least 450 and/or greater than 500 and/or greater than 550 and/or greater than 600 and/or greater than 650 and/or greater than 700 and/or greater than 800 and/or greater than 850 ft²/ft² of the pre-moistened fibrous structure (floor cleaning pad) as measured according to the Mileage Test Method described herein. In another example, a pre-moistened fibrous structure of the present invention exhibits a mileage value of at least 500 and/or at least 600 and/or at least 700 and/or at least 850 ft²/ft² of the pre-moistened fibrous structure (floor cleaning pad) as measured according to the Mileage Test Method described herein.

In one example, a pre-moistened fibrous structure of the present invention may exhibit one or more, such as a combination, of the mileage values described above.

In addition to increased mileage, the fibrous structures of the present invention exhibit increased capacity. In one example, the fibrous structures of the present invention exhibit capacity values of at least 8.5 g of liquid composition/g of dried fibrous structure (dried floor cleaning pad) as measured according to the Capacity Test Method described herein.

In one example, a pre-moistened fibrous structure of the present invention exhibits a capacity value of at least 8.5 and/or greater than 8.7 and/or greater than 9 and/or greater than 9.2 and/or greater than 9.5 and/or greater than 10 g of liquid composition/g of dried fibrous structure (dried floor cleaning pad) as measured according to the Capacity Test Method described herein. In another example, a pre-moistened fibrous structure of the present invention exhibits a capacity value of at least 8.5 and/or at least 9 and/or at least 9.4 and/or at least 10.1 g of liquid composition/g of dried fibrous structure (dried floor cleaning pad) as measured according to the Capacity Test Method described herein.

The pre-moistened fibrous structure of the present invention may be the same or different fibrous structures having the same or different properties and/or surfaces on both sides. In other words, the pre-moistened fibrous structure may be dual-sided. In another example, the pre-moistened fibrous structure is single-sided. In other words, the two sides of the pre-moistened fibrous structure are not the same and one of the sides may not even comprise a fibrous structure surface according to the present invention.

Method for Making a Fibrous Structure

Figure 7A:
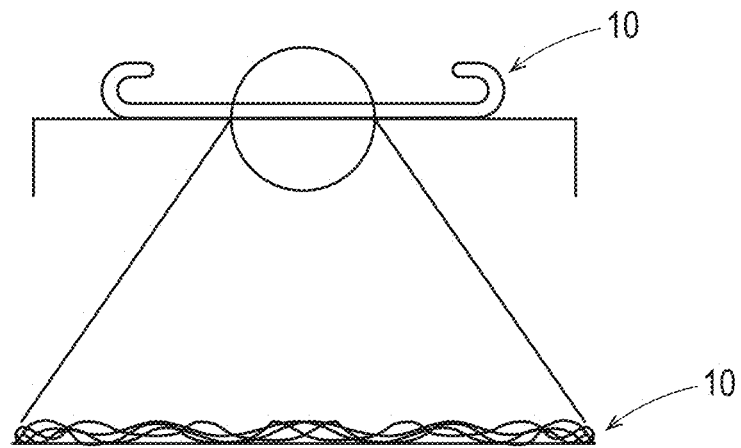
FIG. 7A is a schematic representation of the surface structure of a prior art fibrous structure.
Figure 7B:
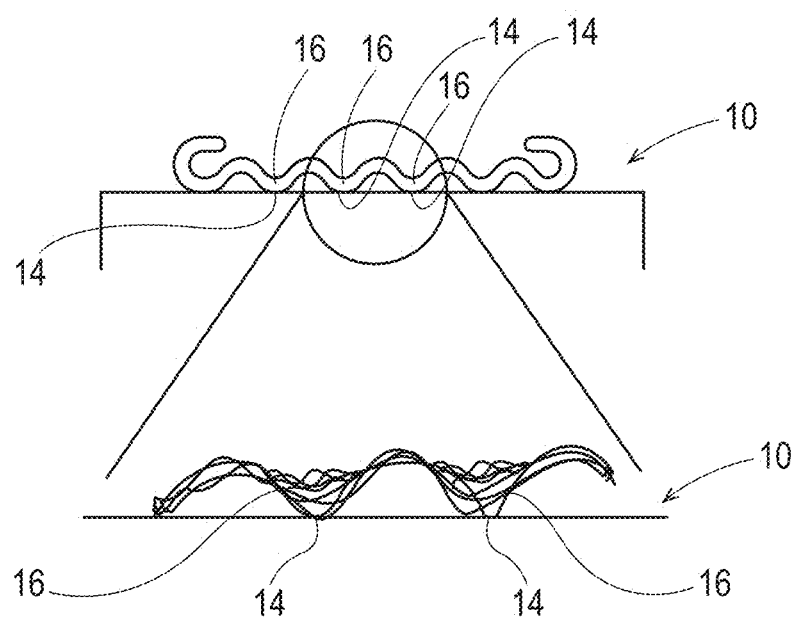
FIG. 7B is a schematic representation of the surface structure of another prior art fibrous structure.
Figure 7C:
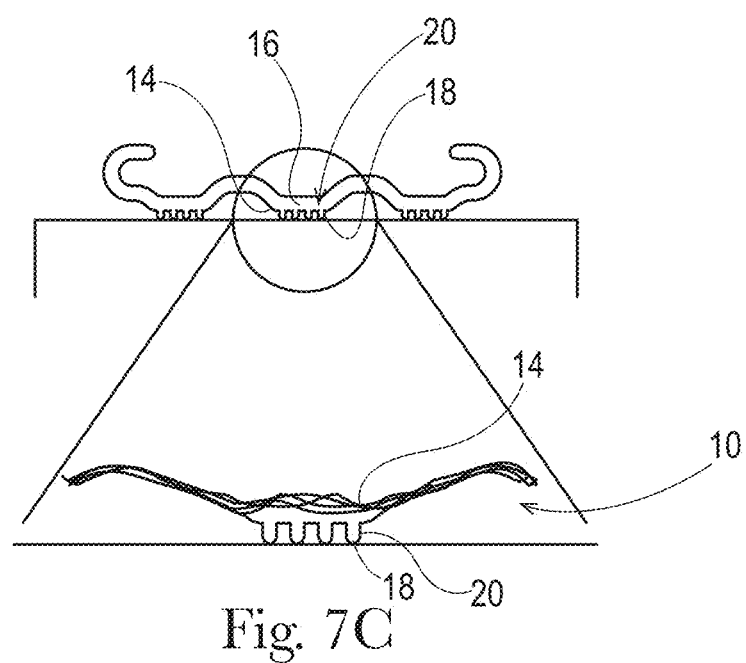
FIG. 7C is a schematic representation of the surface structure of an example of a fibrous structure according to the present invention.

A non-limiting example of a method for making a fibrous structure according to the present invention is represented in FIGS. 8-12. The method 50 for making a fibrous structure 10 according to the present invention comprises the steps of: 1) as shown in FIG. 7, collecting a plurality of filaments 52 and/or a mixture of filaments 52 and solid additives 54, such as fibers, for example pulp fibers, onto a collection device 56, which in this case is a patterned molding member 54, that imparts a texture to at least one surface of the fibrous structure 10 ultimately produced by the method and with the aid of a sufficient amount of vacuum applied to the collection device 56 by vacuum boxes 58. This step of collecting the filaments 52 and/or the mixture of filaments 52 and solid additives 54 on the collection device 56 may comprise subjecting the fibrous structure 10 while on the collection device 56 to a consolidation step by passing the fibrous structure 10 while still on the collection device 56 through a nip formed by two rolls 60, such as steel rolls or a rubber and a steel roll, heated or unheated, flat or patterned, whereby the fibrous structure, while present on the collection device 56.

Figure 8:
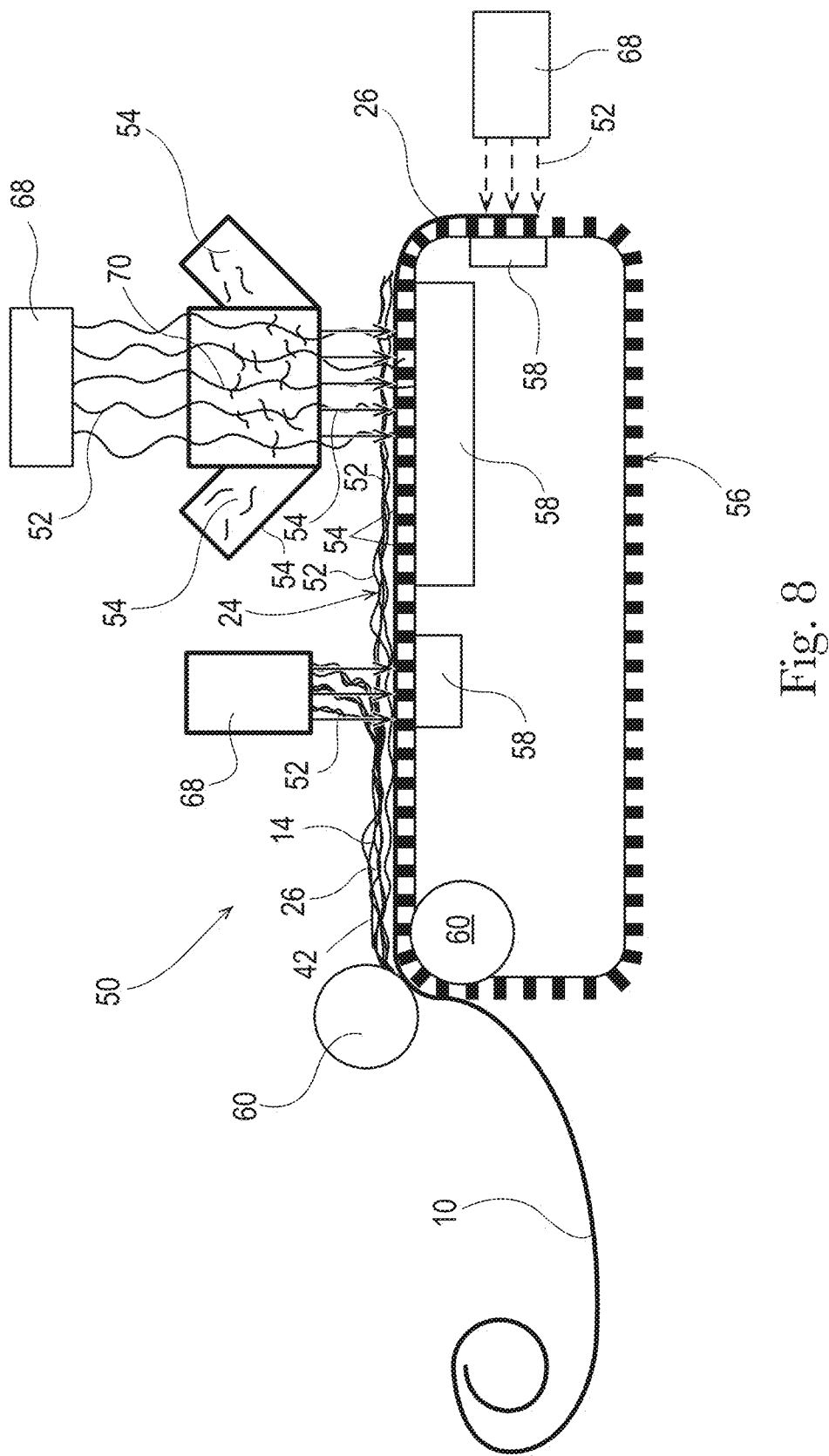
FIG. 8 is a schematic representation of an example of a method for making a fibrous structure according to the present invention.
Figure 9:
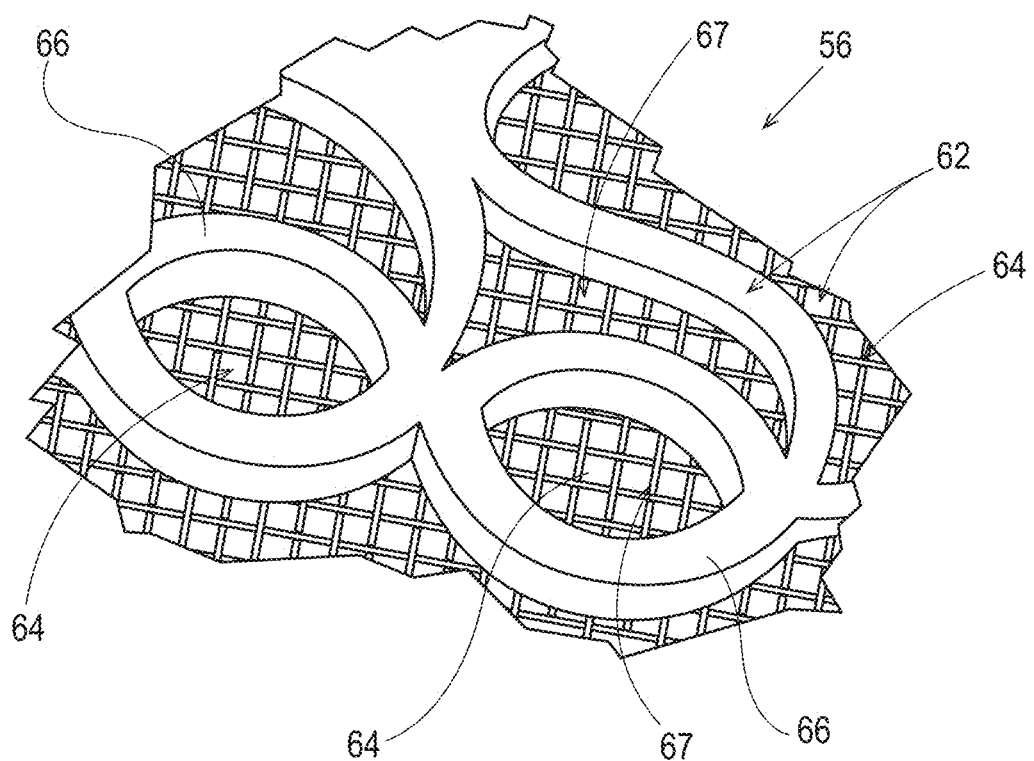
FIG. 9 is a perspective view of a portion of a molding member suitable for use in the method of the present invention.
Figure 10:
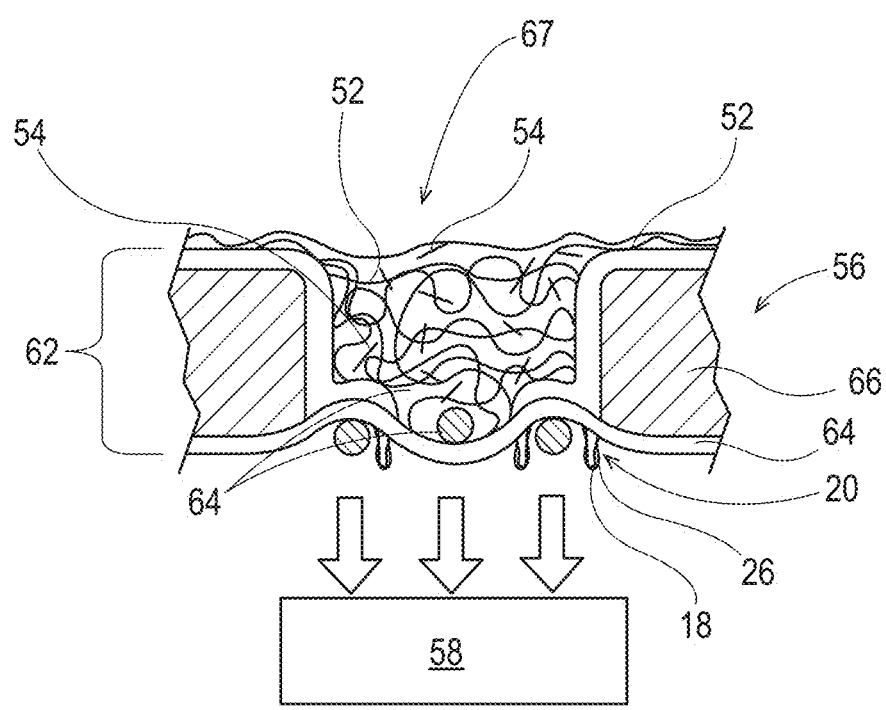
FIG. 10 is a schematic representation of the forming of a fibrous structure of the present invention via the method of the present invention.
Figure 13:
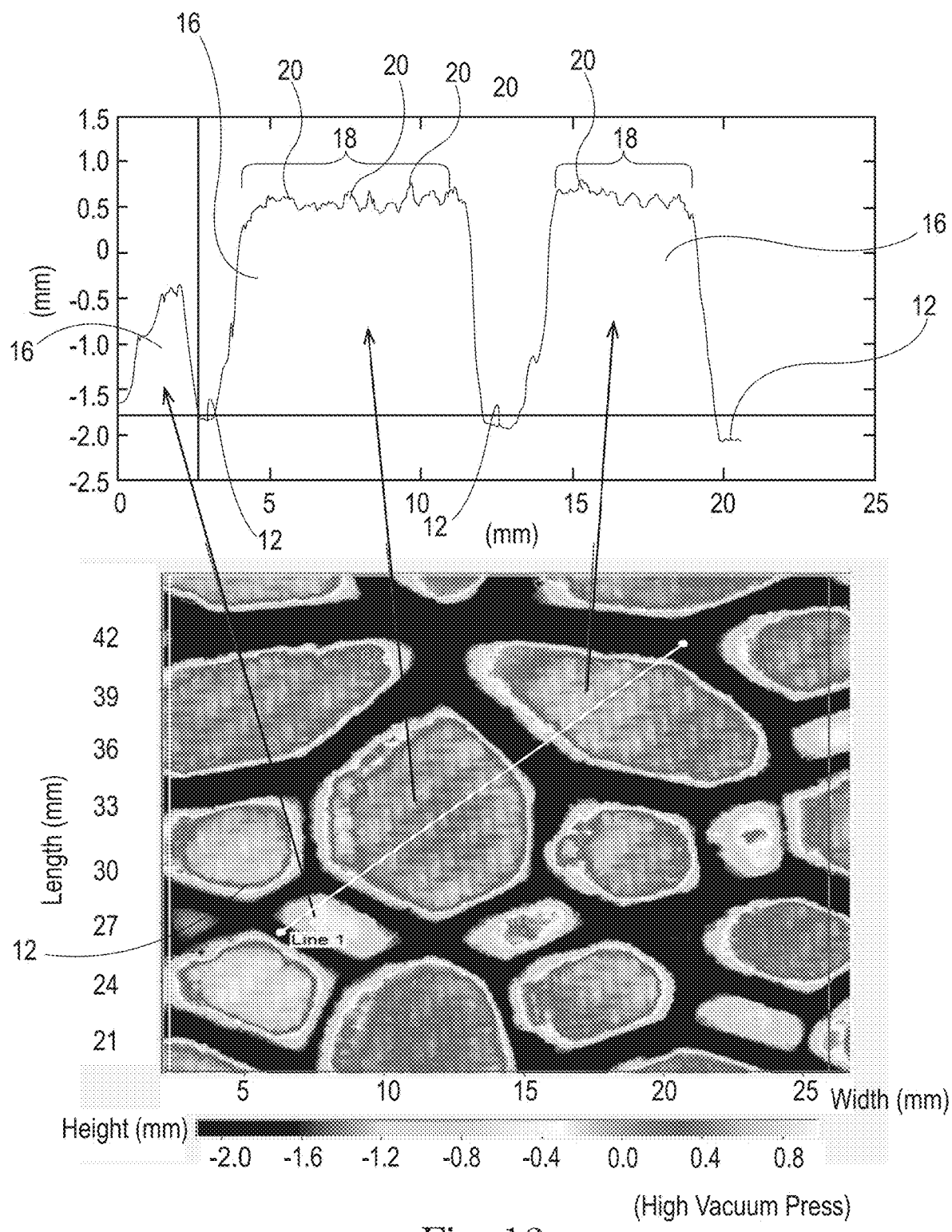
FIG. 13 is a MikroCAD image and corresponding profile representation of a fibrous structure according to the present invention.
Figure 14:
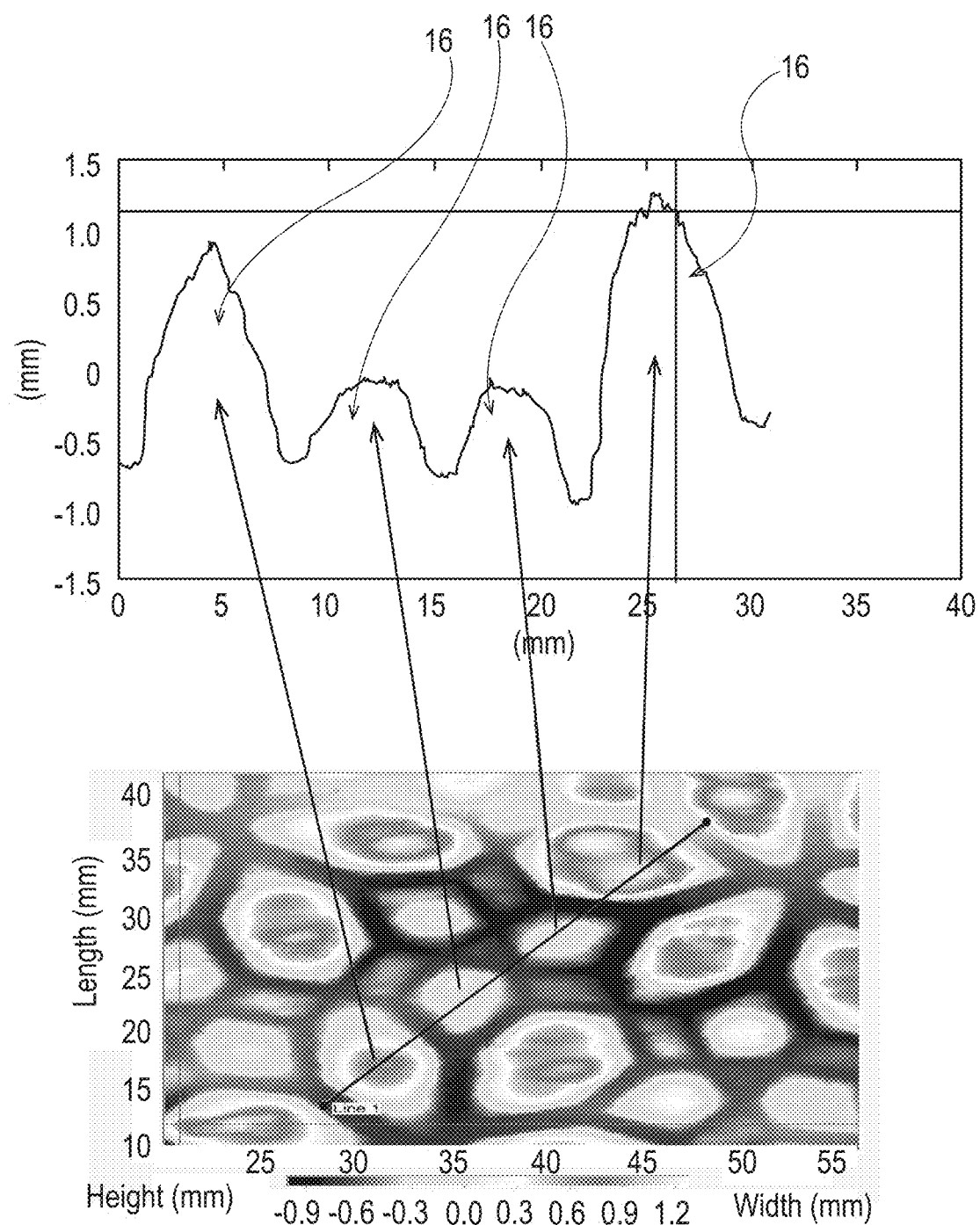
FIG. 14 is a MikroCAD image and corresponding profile representation of a prior art fibrous structure.
Figure 15A:
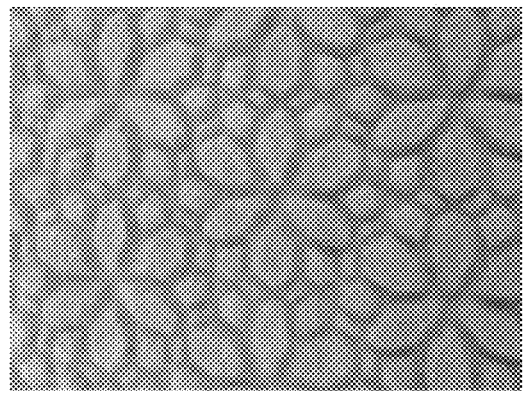
FIG. 15A is an image of an example of a fibrous structure according to the present invention.
Figure 15B:
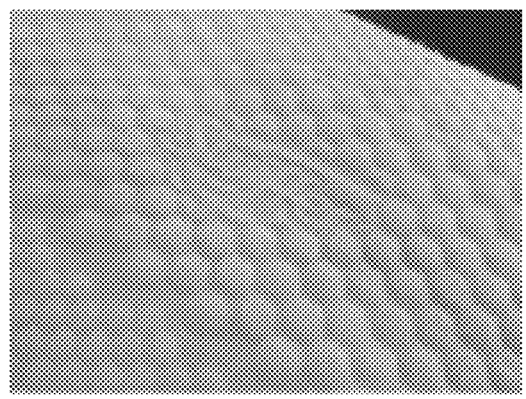
FIG. 15B is an image of another example of a fibrous structure according to the present invention.
Figure 15C:
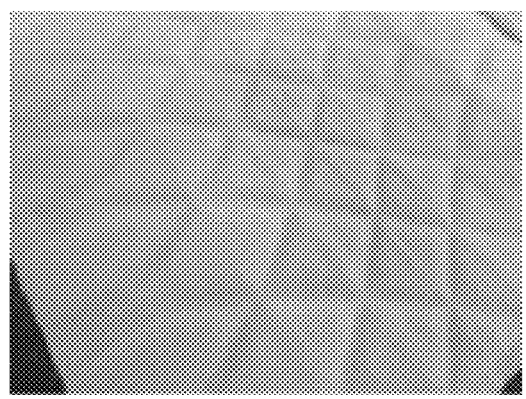
FIG. 15C is an image of another example of a fibrous structure according to the present invention.
Figure 15D:
FIG. 15D is an image of another example of a fibrous structure according to the present invention.
Figure 15E:
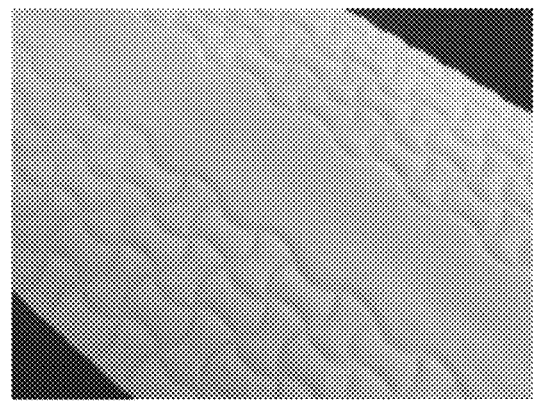
FIG. 15E is an image of another example of a fibrous structure according to the present invention.

The method 50 shown in FIG. 8 comprises the steps of a) collecting a plurality of filaments 52 onto a collection device 56, for example a belt or fabric, such as a molding member 62, to form a scrim component 26. In one example, the collection device 56 such as the molding member 62 may be a straight run while the filaments 52 and solid additives 54 are being collected thereon, unlike as shown in FIG. 8. The collection of the plurality of filaments 52 onto the collection device 56 to form the scrim component 26 is vacuum assisted by one or more vacuum boxes 58. It has been found that providing sufficient vacuum aids in the pulling or deflection of the filaments 52 of the scrim component 26 into the molding member 62 such that the contact surface protrusions (micro protrusions 20) are formed in the fibrous structure 10. For example, as shown in FIGS. 9 and 10, a molding member 62 may comprise a reinforcing element 64, such as a woven fabric, and a resin 66 disposed on the reinforcing element 64. The resin 66 is arranged to form conduits and/or open areas, for example in the form of a pattern, that exposes the reinforcing element 64, to the filaments 52 and/or the mixture of filaments 52 and solid additives 54 during the fibrous structure making process. As shown in FIG. 10, when the filaments 52 and/or the mixture of filaments 52 and solid additives 54 are deposited onto the collection device 56, namely, the molding member 62, the filaments 52 and/or the mixture of filaments 52 and solid additives 54 are pulled into the deflection conduits or openings 67 formed by the resin 66 of the molding member 62 and ultimately into the interstices of the reinforcing element 64 resulting in the formation of a protruding surface (macro protrusion surface 14) with a contact surface (micro protrusion surface 18) and contact surface protrusions (micro protrusions 20). In this example, the vacuum box 58 supplies sufficient vacuum to pull the filaments 52 of the scrim component 26 partially into and/or through the reinforcing element 64 to create the contact surface protrusions (micro protrusions 20). An example of a fibrous structure 10 according to the present invention is illustrated in FIG. 13. FIG. 13 shows a fibrous structure 10 (as represented by a MikroCAD Image and a MikroCAD Profile) that has been subjected to sufficient vacuum during the fibrous structure making process to create one or more contact surface protrusions (micro protrusions 20) that form a contact surface (micro protrusion surface 18) on one or more macro protrusions 16 from the fibrous structure's surface 12. In comparison, Prior Art FIG. 14 shows a fibrous structure 10 (as represented by a MikroCAD Image and MikroCAD Profile) that has been subjected to insufficient vacuum (less than that of the fibrous structure shown in FIG. 13) during the fibrous structure making process such that only one or more macro protrusions 16 are formed from the fibrous structure's surface 12. In other words, no contact surface protrusions (micro protrusions 20) are formed in the fibrous structure 10 of Prior Art FIG. 14.

Depending upon the level of vacuum, the filaments 52 of the scrim component 26 and/or the mixture of the filaments 52 and the solid additives 54 may conform to the collection device 56, for example a molding member 62. The filaments 52 of the present invention may be sourced from a filament source, such as a die 68, for example a meltblow die.

In one example, once the scrim component 26 is formed on the collection device 56, the next step is to mix, such as commingle, a plurality of solid additives 54, such as fibers, for example pulp fibers, such as wood pulp fibers, with a plurality of filaments 52, such as in a coform box 70, and collecting the mixture on the scrim component 26 carried on the collection device 56 to form a core component 24. The collection of the mixture may be vacuum assisted by a vacuum box 58. The vacuum applied via the vacuum box 58 to the mixture may be sufficient to achieve a solid additive concentration difference (difference in average weight % of solid additives) between two or more regions of the fibrous structure 10. It is believed that the rearrangement of the fibers can take one of two modes dependent on a number of factors such as, for example, filament/fiber length. The filaments may bridge the deflection conduits spanning from one ridge to another ridges and may be merely bent into the space defined by the deflection conduit. The solid additives, for example fibers, such as pulp fibers, for example wood pulp fibers, can actually be transported from the region of the ridges of the collection device 56 and into the deflection conduits of the collection device 56.

Optionally, an additional scrim component 26 comprising filaments 52 from a filament source, such as a die 68, for example a meltblow die, may be added to the core component 24 to sandwich the core component 24 between two scrim components 26. This additional scrim component may exhibit the same basis weight as the first scrim component 26, for example if the fibrous structure 10 is going to be used as a single-ply fibrous structure, such as a single-ply pre-moistened fibrous structure, for example a single-ply pre-moistened cleaning pad.

In one example, for example when the fibrous structure 10 is used in a multi-ply fibrous structure, the additional scrim component 26 may exhibit a lower basis weight, for example 1-4 gsm. The additional scrim component 26 in this case helps to reduce lint from the core component 24 during winding of the fibrous structure 10 and subsequent converting with one or more other fibrous structure 10, which may be the same, to make a multi-ply fibrous structure. The lower basis weight additional scrim component 26 may be positioned in the multi-ply fibrous structure such that it forms an interior surface of the multi-ply fibrous structure.

While not wishing to be bound by theory, the vacuum applied via the vacuum boxes 58 to the core and scrim layers may be selected to achieve common intensive properties such as the basis weight, density, or thickness. It is believed that the arrangement of the filaments and solid additives as they accumulate on the collection device may take on different modes dependent on a number of factors such as, for example, filament/fiber length, size of the openings or deflection conduits in the patterned molding member, depth of the deflection conduits in the patterned molding member, filament mobility, fiber mobility, filament temperature hence its drawability, or combinations thereof. The filaments may bridge the deflection conduits spanning from one ridge to other ridges and may be merely bent into the space defined by the deflection conduit while maintaining a position on top of a ridge. The solid additives, for example fibers, such as pulp fibers, for example wood pulp fibers, may be transported or dragged by the vacuum air from the region above the ridges of the collection device 56, for example the molding member 62 and into the deflection conduits or openings 67 of the collection device 56, for example the molding member 62, while the continuous filaments will remain on the ridge or top of the deflection conduit as they lack mobility for example because of their length. Generally, the filaments and solid additives will tend to migrate with the path of the air flow as is established by the vacuum air characteristics and the air permeability of the openings 67 in the molding member 62. With such processes occurring across a large number of the filaments and solid additives during laydown as described herein, the intensive properties of the regions may be established.

The layered scrim component/core component 26/24 and optionally scrim component 26 (fibrous structure 10) may then be subjected to pressure via a nip formed by two rolls 60 and/or plates. In one example, the nip is formed by a flat or even surface rubber roll and a flat or even surface, heated metal roll such that the fibrous structure 10 is deflected into the collection device 56, for example molding member 62. Alternatively, this step of subjecting the fibrous structure 10 to pressure via a nip formed by two rolls or plates could be done as a step after removal from the collection device 56. Or, the step of subjecting the fibrous structure 10 to pressure via a nip formed by two rolls or plates after removal from the collection device 56 does not need to be done.

The collection device 56, for example the molding member 62 may comprise a polymer resin 66 arranged to impart a three-dimensional pattern to the fibrous structure 10 being formed thereon and/or to components of the fibrous structure 10, such as scrim components 26 and core components 24. The collection device 56 may be a patterned molding member 62 that results in the fibrous structure 10 exhibiting a surface pattern, such as a non-random, repeating pattern. The patterned molding member 62 may have a three-dimensional pattern on it that gets imparted to the scrim components 26 and/or the core components 24 during the process. In one example, the solid additives 54 are wood pulp fibers, such as SSK fibers and/or Eucalytpus fibers, and the filaments 52 are polypropylene filaments. The solid additives 54 may be combined with the filaments 52, such as by being delivered to a stream of filaments 52 from a hammermill (not shown) via a solid additive delivery device (not shown) such as a fiber spreader and/or a forming head and/or eductor. The filaments 52 may be created by melt-blowing from a meltblow die, for example as shown in FIGS. 11 and 12.

Figure 11:
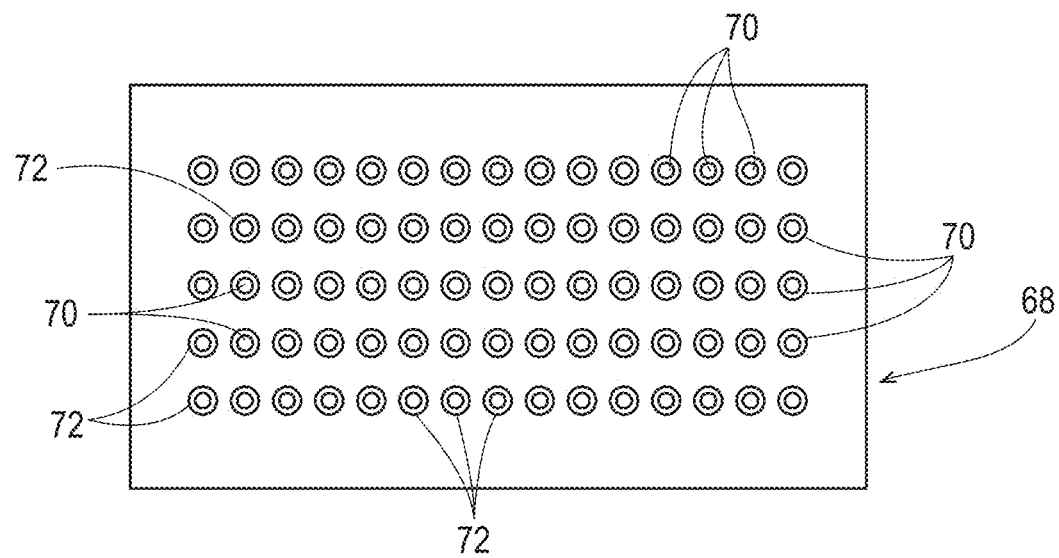
FIG. 11 is a top plan view of a die suitable for use in the method of the present invention.
Figure 12:
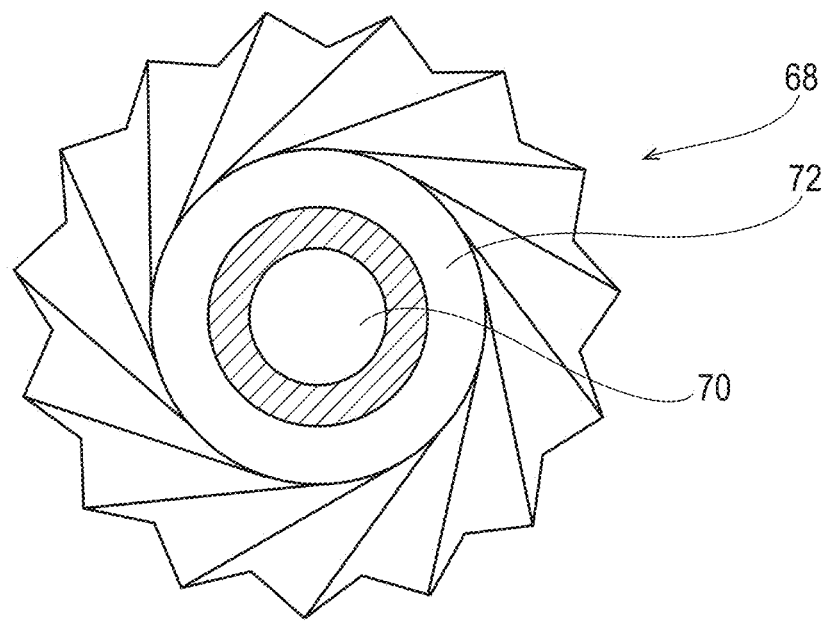
FIG. 12 is a magnified view of a portion of the die of FIG. 11.

In one example of the present invention, the core component 24 is made using a die 68, as shown in FIGS. 11 and 12, comprising at least one filament-forming hole 70, and/or 2 or more and/or 3 or more rows of filament-forming holes 70 from which filaments 52 are spun. At least one row of holes contains 2 or more and/or 3 or more and/or 10 or more filament-forming holes 70. In addition to the filament-forming holes 70, the die 68 comprises fluid releasing holes 72, such as gas-releasing holes, in one example air-releasing holes, that provide attenuation to the filaments formed from the filament-forming holes 70. One or more fluid releasing holes 72 may be associated with a filament-forming hole 70 such that the fluid exiting the fluid-releasing hole 70 is parallel or substantially parallel (rather than angled like a knife-edge die) to an exterior surface of a filament 52 exiting the filament-forming hole 70. In one example, the fluid exiting the fluid-releasing hole 72 contacts the exterior surface of a filament 52 formed from a filament-forming hole 70 at an angle of less than 30° and/or less than 20° and/or less than 10° and/or less than 5° and/or about 0°. One or more fluid-releasing holes 72 may be arranged around a filament-forming hole 70. In one example, one or more fluid-releasing holes 36 are associated with a single filament-forming hole 70 such that the fluid exiting the one or more fluid-releasing holes 72 contacts the exterior surface of a single filament 52 formed from the single filament-forming hole 70. In one example, the fluid-releasing hole 70 permits a fluid, such as a gas, for example air, to contact the exterior surface of a filament 52 formed from a filament-forming hole 70 rather than contacting an inner surface of a filament 52, such as what happens when a hollow filament is formed.

In one example, the die 68 comprises a filament-forming hole 70 positioned within a fluid-releasing hole 72. The fluid-releasing hole 72 may be concentrically or substantially concentrically positioned around a filament-forming hole 70 such as is shown in FIGS. 11 and 12.

In another example, the die 68 comprises filament-forming holes 70 and fluid-releasing holes 72 arranged to produce a plurality of filaments 52 that exhibit a broader range of filament diameters than known filament-forming hole 70 dies, such as knife-edge dies.

In still another example, the die comprises a knife-edge die.

The process of the present invention may include preparing individual rolls of fibrous structure that are suitable for consumer use. The fibrous structure may be contacted by a bonding agent (such as an adhesive and/or dry strength agent), such that the ends of a roll of fibrous structure product according to the present invention comprise such adhesive and/or dry strength agent.

In one example, the fibrous structures are embossed and/or cut into sheets, and collected in stacks of fibrous structures.

The process of the present invention may include preparing individual rolls and/or sheets and/or stacks of sheets of fibrous structures that are suitable for consumer use.

In one example, one or more of the components of the fibrous structure may be made individually and then combined with one or more other components and/or other fibrous structures. In another example, two or more of the fibrous structures of the present invention may be combined with each other and/or with another fibrous structure to form a multi-ply fibrous structure.

The continuous polymer filament diameter distribution of all the components involved can be controlled by adjusting the attenuation process levers. These levers include, but are not limited to, the mass throughput ratio of attenuation fluid to polymer melt, the temperature of the attenuation fluid and polymer melt, spinning nozzle orifice size, polymer melt rheological properties, and polymer melt quenching. In one example, the polymer melt attenuation process can use a jet-to-melt mass ratio between 0 and 27. In another example, the polymer melt is extruded at 350° F. while the attenuation fluid was injected at 395° F. In two similar examples, polymer melt is either extruded through a 0.018" orifice diameter or a 0.015" orifice diameter at the same jet-to-melt mass ratio and temperature. In yet another example, different melt flow rate (MFR) combinations of isotactic polypropylene resins can be extruded. In still another example, cold air at 73° F. and four times more than the attenuation air by mass is injected into the forming zone and impinges the attenuation jet to drastically decrease polymer and air temperature.

Each fibrous structure can have either the same or different fiber diameter distribution as the other fibrous structures. In one example having a three-ply fibrous structure, the two plies sandwiching the center ply can have larger mean filament diameter with the same or different filament diameter distribution to provide more surface roughness. In a variation of the previous example, only one of the outer plies has a larger mean filament diameter with the same or different filament diameter distribution as the core ply, while the other outer ply has a smaller mean filament diameter with the same or different filament diameter distribution as the core ply. In another example involving a one-ply fibrous structure, the mean meltblown filament diameter is increased to provide scaffold structure for larger void space.

The process for making fibrous structure 10 may be close coupled (where the fibrous structure is convolutedly wound into a roll prior to proceeding to a converting operation) or directly coupled (where the fibrous structure is not convolutedly wound into a roll prior to proceeding to a converting operation) with a converting operation to emboss, print, deform, surface treat, thermal bond, cut, stack or other post-forming operation known to those in the art. For purposes of the present invention, direct coupling means that the fibrous structure 10 can proceed directly into a converting operation rather than, for example, being convolutedly wound into a roll and then unwound to proceed through a converting operation.

Molding Members

The fibrous structures of the present invention are formed on molding members 62, for example a patterned molding member such as is shown in FIGS. 9 and 10, that result in the fibrous structures of the present invention. In one example, the pattern molding member comprises a non-random repeating pattern. In another example, the pattern molding member comprises a resinous pattern.

A "reinforcing element" may be a desirable (but not necessary) element in some examples of the molding member, serving primarily to provide or facilitate integrity, stability, and durability of the molding member comprising, for example, a resinous material. The reinforcing element can be fluid-permeable or partially fluid-permeable, may have a variety of embodiments and weave patterns, and may comprise a variety of materials, such as, for example, a plurality of interwoven yarns (including Jacquard-type and the like woven patterns), a felt, a plastic, other suitable synthetic material, or any combination thereof.

As shown in FIGS. 9 and 10, a non-limiting example of a molding member 62, for example a patterned molding member, suitable for use in the present invention comprises a reinforcing element 64, such as a fabric, upon which a pattern of resin 66 is deposited. The pattern of resin 66 shown in FIGS. 9 and 10 comprises a continuous network or substantially continuous network of resin 66 that impart knuckles to a fibrous structure 10 formed thereon. The continuous network or substantially continuous network of resin 66 defines deflection conduits or openings 67 that impart pillows to a fibrous structure 10 formed thereon.

In one example, the resin 66 on the molding member 62 may exhibit widths of from about 200 μm to about 5 mm and/or from about 200 μm to about 4 mm and/or from about 200 μm to about 3 mm and/or from about 300 μm to about 2 mm and/or from about 300 μm to about 1 mm and/or from about 300 μm to about 0.5 mm. In one example, the width of the resin 66 may vary along its length or may be constant width along its length.

In one example, the resin 66 on the molding member 62 may exhibit depths as measured from the collection side surface plane of the reinforcing element 64 to the top of the resin pattern of greater than 0 to about 3.0 mm and/or greater than 0 to about 2.0 mm and/or greater than 0 to about 1.5 mm and/or greater than 0 to about 1.0 mm and/or greater than 0 to about 0.5 mm. In one example, the resin depths may vary within the molding member 62 or may be constant depth within the molding member 62.

In another example, the resin 66 on the molding member 62 may exhibit depths as measured from the collection side surface plane of the reinforcing element 64 to the top of the resin pattern of from about 0.1 mm to about 3.0 mm and/or from about 0.1 mm to about 2.0 mm and/or from about 0.5 mm to about 2.0 mm and/or from about 0.5 mm to about 1.0 mm. In one example, the resin depths may vary within the molding member 62 or may be constant depth within the molding member 62.

In even another example, the resin 66 on the molding member 62 may exhibit depths as measured from the collection side surface plane of the reinforcing element 64 to the top of the resin pattern of from about 0.1 mm to about 1.0 mm and/or from about 0.5 mm to about 2.0 mm and/or from about 1.0 mm to about 3.0 mm. In one example, the resin depths may vary within the molding member 62 or may be constant depth within the molding member 62.

FIGS. 15A-15E show representative examples of fibrous structures made according to the present invention.

Figure 16:
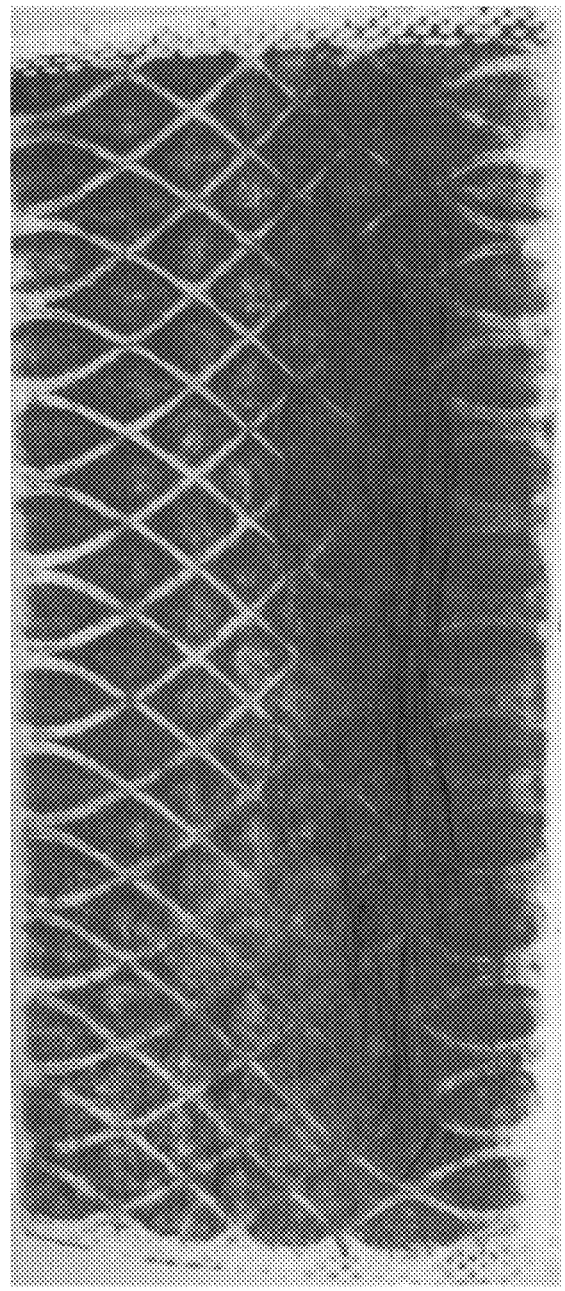
FIG. 16 is an image of an example of a fibrous structure according to the present invention after use.
Figure 17:
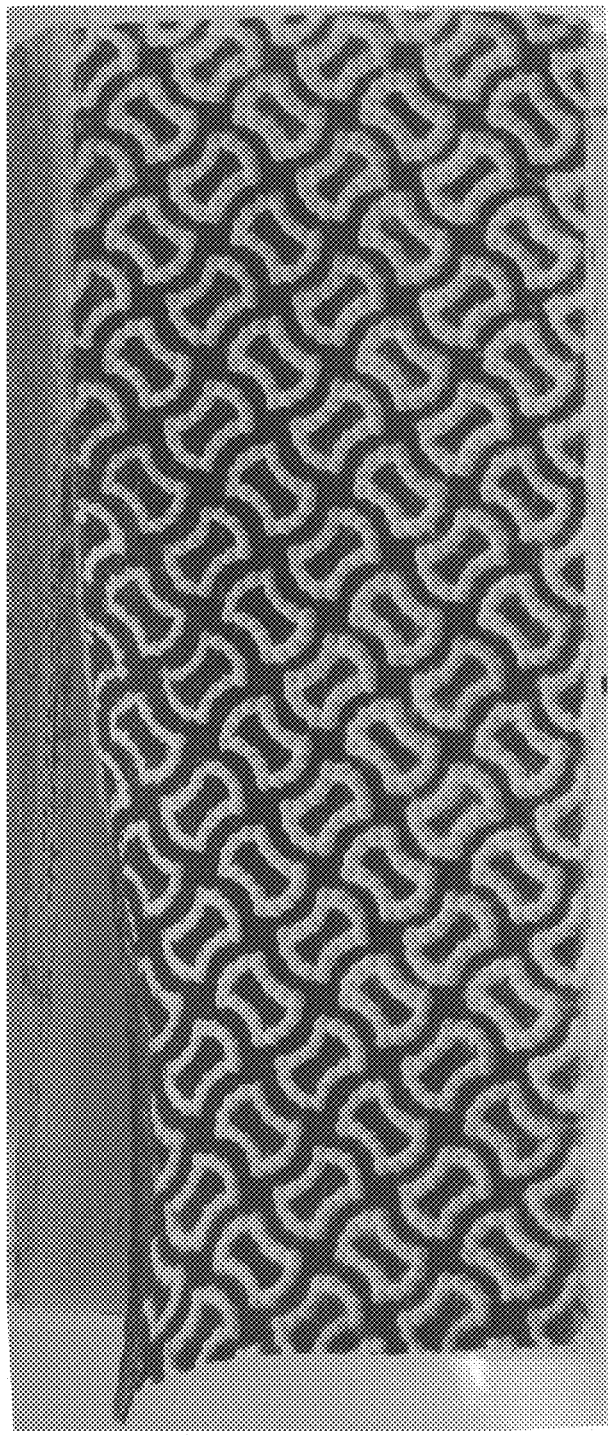
FIG. 17 is an image of an example of a prior art fibrous structure after use.

As shown in FIG. 16, a pre-moistened fibrous structure, for example a pre-moistened floor cleaning pad, according to the present invention gives a better consumer signal of optimal utilization of the pre-moistened fibrous structure compared to a prior art pre-moistened fibrous structure shown in Prior Art FIG. 17. The prior art pre-moistened fibrous structure leaves too much white (non-soiled) area on the pre-moistened fibrous structure after cleaning. It has been found that too much bond surface area (knuckle surface area or in other words fibrous structure surface surface area) on the fibrous structures, such as is the case in Prior Art FIG. 17, results in the fibrous structures looking underutilized during and/or after use. As shown in FIG. 16, the bond surface area (knuckle surface area (the continuous knuckle network) or in other words fibrous structure surface surface area) on the fibrous structure is less than the bond surface area (knuckle surface area (the discrete knuckle pattern) or in other words fibrous structure surface surface area) of the fibrous structure shown in Prior Art FIG. 17. In one example, the bond surface area (knuckle surface area or in other words fibrous structure surface surface area) is 15% or less and/or less than 15% and/or less than 12% and/or less than 10% and/or less than 7% and/or less than 5% and/or less than 3% to about 1% and/or to about 2% (which means that the pillow surface surface area and micro pillow surface surface area, which is made up of the protruding surface surface area (macro protrusion surface surface area) and/or the contact surface surface area (micro protrusion surface surface area) is greater than 50% and/or greater than 60% and/or at least 85% and/or greater than 85% and/or greater than 88% and/or greater than 90% and/or greater than 93% and/or greater than 95% and/or up to about 99% or up to about 98% of the fibrous structure surface surface area).

As shown in FIG. 16, the pillow surface surface area of the fibrous structure has been increased (bond surface area has been decreased) compared to the pillow surface area of the fibrous structure of Prior Art FIG. 17. It has been found that increasing the pillow surface surface area (the protruding surface surface area (macro protrusion surface surface area)) of the fibrous structure makes the fibrous structure look more fully utilized during and/or after use. However, the increased pillow surface surface area negatively increases the friction of the fibrous structure during use.

Therefore, it has been found that incorporating a micro pattern, for example a plurality of contact surface protrusions (micro protrusions or micro pillows) on one or more of the protruding surfaces (macro protrusion surfaces or pillow surfaces) decreases the friction of the fibrous structure without negatively impacting the soiled appearance. In other words, by adding the contact surface protrusions (micro protrusions or micro pillows) to one or more protruding surfaces (macro protrusion surfaces or pillow surfaces), the fibrous structures of the present invention still appear to be more fully utilized than the fibrous structure in Prior Art FIG. 17 without exhibiting the friction negatives associated with increased pillow surface surface area (the protruding surface surface area).

Products Comprising Fibrous Structures

The fibrous structures of the present invention may be used as and/or incorporated into various products, for example consumer products. Non-limiting examples of such products include wipes, for example wet wipes, such as baby wipes, adult wipes, facial cleaning wipes, and/or hard surface cleaning wipes, cleaning pads/sheets, for example floor cleaning pads, both dry and wet and those used with liquid cleaning compositions and/or water, paper towels and other dry cleaning disposable products, such as disposable dish cloths, and facial tissues.

Cleaning Pads/Sheets

The fibrous structures of the present invention may be used as and/or incorporated into cleaning pads and/or cleaning sheets, such as floor cleaning pads, for use alone or with an implement.

The cleaning pad or sheet may exhibit a basis weight of from about 20 gsm to about 1000 gsm and/or from about 30 gsm to about 500 gsm and/or from about 60 gsm to about 300 gsm and/or from about 75 gsm to about 200 gsm and/or from about 100 gsm to about 200 gsm.

The cleaning pad or sheet may comprise one or more additives to improve cleaning performance and/or enhance the cleaning experience. Non-limiting examples of suitable additives include waxes, such as microcrystalline wax, oils, adhesives, perfumes, and combinations thereof.

If desired, the cleaning pad or sheet may be pre-moistened. The cleaning pad or sheet may be pre-moistened with a liquid composition that provides for cleaning of the target surface, such as a floor, but yet does not require a post-cleaning rinsing operation. When pre-moistened, the cleaning pad or sheet may be loaded with at least 3 and/or 4 and/or 5 grams of a liquid composition, such as a cleaning solution, per gram of dry fibrous structure, for example dry cleaning pad or sheet, but typically not more than 10 and/or not more than 8.5 and/or not more than 7.5 grams per gram. The liquid, for example cleaning solution, may comprise a surfactant, such as APG surfactant which minimizes streaking since there is typically not a rinsing operation, agglomerating chemicals, disinfectants, bleaching solutions, perfumes, secondary surfactants, and combinations thereof. A suitable pre-moistened cleaning pad or sheet maybe pre-moistened according to the teachings of commonly assigned U.S. Pat. No. 6,716,805.

The cleaning pad or sheet may comprise a plurality of layers to provide for scrubbing, for example provides for more aggressive cleaning of the target surface, liquid storage, and other particularized tasks for the cleaning operation. For example, a scrubby material, such as in the form of a strip, may be added to a surface of the fibrous structure to provide a scrubby surface or portion of a surface on the cleaning pad or sheet. A non-limiting example of a suitable scrubbing material or strip may comprise a polyolefinic film, such as LDPE, and may have outwardly extending perforations. The scrubbing strip may be made and used according to commonly assigned U.S. Pat. Nos. 8,250,700; 8,407,848, D551,409 S and/or D614,408 S.

The cleaning pad or sheet according to the present invention may be used with a stick-type cleaning implement. The cleaning implement may comprise a plastic head for holding the cleaning sheet and an elongate handle articulably connected thereto. The handle may comprise a metal or plastic tube or solid rod.

The head may have a downwardly facing surface, to which the cleaning pad or sheet may be attached. The downwardly facing service may be generally flat, or slightly convex. The head may further have an upwardly facing surface. The upwardly facing surface may have a universal joint to facilitate connection of the elongate handle to the head.

A hook and loop system may be used to attach the cleaning pad or sheet directly to the bottom of the head. Alternatively, the upwardly facing surface may further comprise a mechanism, such as resilient grippers, for removably attaching the cleaning pad or sheet to the implement. Alternatively, a hook and loop system may be used to attach the cleaning pad or sheet to the head. If grippers are used with the cleaning implement, the grippers may be made according to commonly assigned U.S. Pat. Nos. 6,305,046; 6,484, 346, 6,651,290 and/or D487,173.

If desired, the cleaning implement may have an axially rotatable beater bar and/or vacuum type suction to assist in removal of debris from the target surface. Debris removed from the target surface may be collected in a dust bin. The dust bin may be mounted within the head, or, alternatively, on the elongate handle. A suitable stick-type cleaning implement may be made according to commonly assigned U.S. Pat. Des. Nos. D391,715, D409,343, D423,742, D481,184, D484,287, D484,287 and/or D588,770. A suitable vacuum type cleaning implement may be made according to the teachings of U.S. Pat. Nos. 7,137,169, D484,287 S, D615, 260 S and D615,378 S. An implement having a beater bar may be made according to commonly assigned U.S. Published Patent Application No. 2013/0333129. A motorized implement may be made according to commonly assigned U.S. Pat. No. 7,516,508.

The cleaning implement may further comprise a reservoir for storage of a cleaning solution. The reservoir may be replaced when the cleaning solution is depleted and/or refilled as desired. The reservoir may be disposed on the head or the handle of the cleaning implement. The neck of the reservoir may be offset per commonly assigned U.S. Pat. No. 6,390,335. The cleaning solution contained therein may be made according to the teachings of commonly assigned U.S. Pat. No. 6,814,088.

The cleaning implement may further comprise a pump for dispensing cleaning solution from the reservoir onto the target surface, such as a floor. The pump may be battery powered or operated by line voltage. Alternatively, the cleaning solution may be dispensed by gravity flow. The cleaning solution may be sprayed through one or more nozzles to provide for distribution of the cleaning solution onto the target surface in an efficacious pattern.

If a replaceable reservoir is utilized, the replaceable reservoir may be inverted to provide for gravity flow of the cleaning solution. Or the cleaning solution may be pumped to the dispensing nozzles. The reservoir may be a bottle, and may made of plastic, such as a polyolefin. The cleaning implement may have a needle to receive the cleaning solution from the bottle. The bottle may have a needle piercable membrane, complementary to the needle, and which is resealed to prevent undesired dripping of the cleaning solution during insertion and removal of the replaceable reservoir. Alternatively or additionally, If desired, the implement may also provide for steam to be delivered to the cleaning pad or sheet and/or to the floor or other target surface.

A suitable reservoir and fitment therefore may be made according to the teachings of commonly assigned U.S. Pat. Nos. 6,386,392, 7,172,099, D388,705, D484,804, D485, 178. A suitable cleaning implement may be made according to the teachings of commonly assigned U.S. Pat. Nos. 5,888,006; 5,960,508, 5,988,920; 6,045,622, 6,101,661; 6,142,750, 6,579,023; 6,601,261, 6,722,806; 6,766,552, D477,701 and/or D487,174. A steam implement may be made according to the teachings of jointly assigned U.S. Published Patent Application No. 2013/0319463.

The cleaning pad or sheet may comprise layers, to provide for absorption and storage of cleaning solution deposited on the target surface. If desired, the cleaning pad or sheet may comprise superabsorbent materials to increase the absorbent capacity of the cleaning pad or sheet. The superabsorbent materials may be distributed within the cleaning pad or sheet in such a manner to avoid rapid absorbency and absorb fluids slowly, to provide for the most effective use of the cleaning pad or sheet.

The cleaning pad or sheet may comprise plural layers disposed in a laminate. The lowest, or downwardly facing outer layer, may comprise apertures to allow for absorption of cleaning solution therethrough and to promote the scrubbing of the target surface. Intermediate layers may provide for storage of the liquids, and may comprise the superabsorbent materials. The cleaning pad or sheet may have an absorbent capacity of at least 10, 15, or 20 grams of cleaning solution per gram of dry cleaning pad or sheet, as set forth in commonly assigned U.S. Pat. Nos. 6,003,191 and 6,601, 261.

The top or upwardly facing outer layer of the cleaning pad or sheet (for example, the surface that contacts the cleaning implement), maybe liquid impervious in order to minimize loss of absorbed fluids. The top layer may further provide for releasable attachment of the cleaning pad or sheet to a cleaning implement. The top layer may be made of a polyolefinic film, such as LDPE.

The fibrous structures of the present invention may be cut to provide strips or portions of strips to form a cleaning article. The fibrous structure and/or strips thereof may comprise an additive to assist in removal of dust and other debris from a target surface, such as a hard surface, for example a coffee table, mantle, and the like. The additive may comprise waxes, such as microcrystalline wax, oils, adhesives and combinations thereof. The cleaning article may be made according to U.S. Pat. No. 6,813,801. The cleaning article may accept one or more complementary fork tines of a handle. The fork tines may be removably inserted into the cleaning article or sleeves formed on the cleaning article to provide for improved ergonomics. The handle may be plastic and made according to the teachings of U.S. Pat. Nos. 7,219,386; 7,293,317 and/or 7,383,602.

Non-Limiting Examples of Fibrous Structures of the Present Invention

Process Example 1—Process for Making a Two Layer Fibrous Structure of the Present Invention A 21%:27.5%47.5%:4% blend of Lyondell-Basell PH835 polypropylene:Lyondell-Basell Metocene MF650W polypropylene:Lyondell-Basell Metocene MF650X: Ampacet 412951 opacifier is dry blended, to form a melt blend. A meltblown layer of the meltblown filaments, such as a scrim component, is produced first. This addition of the meltblown scrim component layer can help reduce the lint created from the fibrous structure during use by consumers and is performed prior to any thermal bonding operation of the fibrous structure. The scrim layer can be the same or different than the meltblown filaments in the center formed fibrous structure. To make the meltblown filaments for the exterior layers, A 15.5 inch wide Biax 12 row spinnerette with 192 nozzles per cross-direction inch, commercially available from Biax Fiberfilm Corporation, is utilized. 32 nozzles per cross-direction inch of the 192 nozzles have a 0.018 inch inside diameter while the remaining nozzles are solid, i.e. there is no opening in the nozzle. Approximately 0.2 grams per hole per minute (ghm) of the melt blend is extruded from the open nozzles to form meltblown filaments from the melt blend. Approximately 472 SCFM of compressed air, equivalent to a jet-to-melt mass ratio of 26, is heated such that the air exhibits a temperature of about 395° F. at the spinnerette. A forming vacuum pulls air through a collection device, such as a non-patterned forming belt or through-air-drying fabric, thus collecting the meltblown filaments to form a fibrous structure.

A 20%:27.5%47.5%:5% blend of Lyondell-Basell PH835 polypropylene:Lyondell-Basell Metocene MF650W polypropylene:Lyondell-Basell Metocene MF650X: Polyvel S1416 wetness agent is dry blended, to form a melt blend. The melt blend is heated to 400° F. through a melt extruder. A 15.5 inch wide Biax 12 row spinnerette with 192 nozzles per cross-direction inch, commercially available from Biax Fiberfilm Corporation, is utilized. 24 nozzles per cross-direction inch of the 192 nozzles have a 0.018 inch inside diameter while the remaining nozzles are solid, i.e. there is no opening in the nozzle. Approximately 0.5 grams per hole per minute (ghm) of the melt blend is extruded from the open nozzles to form meltblown filaments from the melt blend. Approximately 320 SCFM of compressed air, equivalent to a jet-to-melt mass ratio of 7, is heated such that the air exhibits a temperature of about 395° F. at the spinnerette. Approximately 750 g/minute of Golden Isle (from Georgia Pacific) 4725 semi-treated SSK pulp is defibrillated through a hammermill to form SSK wood pulp fibers (solid additive). Air at a temperature of about 85 to 90° F. and about 80% relative humidity (RH) is drawn into the hammermill. Approximately 35 kg/min of air split into two symmetric streams carry the pulp fibers to a solid additive spreader. The solid additive spreader turns the pulp fibers and distributes the pulp fibers in the cross-direction such that the pulp fibers are injected into the meltblown filaments at a 45° angle (with respect to the flow of the meltblown filaments). A forming box surrounds the area where the meltblown filaments and pulp fibers are commingled. This forming box is designed to reduce the amount of air allowed to enter or escape from this commingling area. A forming vacuum pulls air through a collection device, such as a patterned belt carrying the first scrim layer, thus collecting the commingled meltblown filaments and pulp fibers to form a fibrous structure comprising a pattern of non-random, repeating microregions, including pillows (macro protrusions) and/or micro pillows (micro protrusions) and knuckles, of differing intensive properties and an exterior scrim layer. The fibrous structure formed by this process comprises about 80% by dry fibrous structure weight of pulp and about 20% by dry fibrous structure weight of meltblown filaments.

Another meltblown layer of the meltblown filaments using the same melt blend as the first scrim layer, is added to the opposite side of the above formed fibrous structure. This scrim layer can be the same or different than the meltblown filaments in the center formed fibrous structure or from the scrim on the opposite side. This scrim layer can be used as a process aid to prevent linting during substrate making. To make the meltblown filaments for this exterior layer, A 15.5 inch wide Biax 12 row spinnerette with 192 nozzles per cross-direction inch, commercially available from Biax Fiberfilm Corporation, is utilized. 8 nozzles per cross-direction inch of the 192 nozzles have a 0.018 inch inside diameter while the remaining nozzles are solid, i.e. there is no opening in the nozzle. Approximately 0.18 grams per hole per minute (ghm) of the melt blend is extruded from the open nozzles to form meltblown filaments from the melt blend. Approximately 426 SCFM of compressed air, equivalent to a jet-to-melt mass ratio of 26, is heated such that the air exhibits a temperature of about 395° F. at the spinnerette. A forming vacuum pulls air through a collection device, such as a non-patterned forming belt or through-air-drying fabric, thus collecting the meltblown filaments to form a fibrous structure on top of the above formed fibrous structure.

The combined structure above can be calendared on the forming fabric to create even more distinct regions of differing intensive properties. The fibrous structure may be convolutedly wound to form a roll of fibrous structure.

At least two such roll of fibrous structures can be laminated using adhesive or mechanical bonding to create at least two or more plies structures. In this example, two rolls of the fibrous structures above formed on patterned fabric are unwound such that the patterning sides are facing away. A Nordson adhesive applicator with summit nozzles added 12 gsm of Bostik H2031 adhesive at 170° C. onto the non-patterned side of one of the fibrous structure. The glued fibrous structure is laminated to the non-patterned side of the other fibrous structure, and the combined fibrous structure is then send through a nip roll to set the adhesive bond and convolutedly wound to form a roll of fibrous structure.

Process Example 2—Process for Making Macro-Micro Fibrous Structure of the Present Invention Making of a multi-ply structure, including at least one scrim layer, with macro and micro scale repeating features, is described in this example.

A 21%:27.5%47.5%:4% blend of Lyondell-Basell PH835 polypropylene:Lyondell-Basell Metocene MF650W polypropylene:Lyondell-Basell Metocene MF650X: Ampacet 412951 opacifier is dry blended, to form a melt blend. A meltblown layer of the meltblown filaments, such as a scrim component, is produced first. To make the meltblown filaments of the scrim component, a 15.5 inch wide Biax 12 row spinnerette with 192 nozzles per cross-direction inch, commercially available from Biax Fiberfilm Corporation, is utilized. 32 nozzles per cross-direction inch of the 192 nozzles have a 0.018 inch inside diameter while the remaining nozzles are solid, i.e. there is no opening in the nozzle. Approximately 0.2 grams per hole per minute (ghm) of the melt blend is extruded from the open nozzles to form meltblown filaments from the melt blend. Approximately 472 SCFM of compressed air, equivalent to a jet-to-melt mass ratio of 26, is heated such that the air exhibits a temperature of about 395° F. at the spinnerette. A forming vacuum operating at 23 mBar pressure pulls air through a collection device, such as a non-macro patterned, weaved forming belt of air permeability of 700 SCFM, thus collecting the meltblown filaments to form a fibrous structure that conforms to the micro texture from the weaving pattern of the collection device. The collection device can also have macro patterns, in which meltblown filaments will first conform to the macro patterns of the collection device, and then conform to the micro weave texture of the reinforcing element of the collection device.

A 20%:27.5%:47.5%:5% blend of Lyondell-Basell PH835 polypropylene:Lyondell-Basell Metocene MF650W polypropylene:Lyondell-Basell Metocene MF650X: Polyvel S1416 wetness agent is dry blended, to form a melt blend. The melt blend is heated to 400° F. through a melt extruder. A 15.5 inch wide Biax 12 row spinnerette with 192 nozzles per cross-direction inch, commercially available from Biax Fiberfilm Corporation, is utilized. 24 nozzles per cross-direction inch of the 192 nozzles have a 0.018 inch inside diameter while the remaining nozzles are solid, i.e. there is no opening in the nozzle. Approximately 0.5 grams per hole per minute (ghm) of the melt blend is extruded from the open nozzles to form meltblown filaments from the melt blend. Approximately 320 SCFM of compressed air, equivalent to a jet-to-melt mass ratio of 7, is heated such that the air exhibits a temperature of about 395° F. at the spinnerette. Approximately 750 g/minute of Golden Isle (from Georgia Pacific) 4725 semi-treated SSK pulp is defibrillated through a hammermill to form SSK wood pulp fibers (solid additive). Air at a temperature of about 85 to 90° F. and about 80% relative humidity (RH) is drawn into the hammermill. Approximately 35 kg/min of air split into two symmetric streams carry the pulp fibers to a solid additive spreader. The solid additive spreader turns the pulp fibers and distributes the pulp fibers in the cross-direction such that the pulp fibers are injected into the meltblown filaments at a 45° angle (with respect to the flow of the meltblown filaments). A forming box surrounds the area where the meltblown filaments and pulp fibers are commingled. This forming box is designed to reduce the amount of air allowed to enter or escape from this commingling area. A forming vacuum pulls air through the same collection device carrying the first said scrim layer, thus collecting the commingled meltblown filaments and pulp fibers to form a fibrous structure on top of the patterned scrim layer (scrim component). The fibrous structure formed by this process comprises about 80% by dry fibrous structure weight of pulp and about 20% by dry fibrous structure weight of meltblown filaments.

After the fibrous structure, with additional meltblown filaments (scrim layers) has been formed on the collection device, the fibrous structure is calendered at elevated temperature, while the fibrous structure is still on the collection device. In this example, the fibrous structure with meltblown filaments on the patterned side, is calendared while on the collection device with macro pattern and micro weave pattern at about 240 PLI (Average pounds per linear CD inch across the patterned molding member CD width of 21"), which creates pillows (macro protrusions) and/or micro pillows (micro protrusions) and knuckles, with a flat or even surface metal anvil roll facing the fibrous structure and a flat or even surface rubber coated roll facing the patterned molding member. The metal anvil roll has an internal temperature of 290° F. as supplied by an oil heater.

After the fibrous structure is collected in roll form, it is further converted by being lotioned and cut to form a finished product.

Process Example 3—Process for Making Macro-Micro Textured Fibrous Structure on Patterned Molding Member of the Present Invention Making of a multi-ply structure, including at least one scrim layer (scrim component), with macro and micro scale repeating features, is described in this example.

A 21%:27.5%:47.5%:4% blend of Lyondell-Basell PH835 polypropylene Lyondell-Basell Metocene MF650W polypropylene:Lyondell-Basell Metocene MF650X Ampacet 412951 opacifier is dry blended, to form a melt blend. A meltblown layer of the meltblown filaments, such as a scrim component, is produced first. To make the meltblown filaments for the scrim component, a 15.5 inch wide Biax 12 row spinnerette with 192 nozzles per cross-direction inch, commercially available from Biax Fiberfilm Corporation, is utilized. 32 nozzles per cross-direction inch of the 192 nozzles have a 0.018 inch inside diameter while the remaining nozzles are solid, i.e. there is no opening in the nozzle. Approximately 0.2 grams per hole per minute (ghm) of the melt blend is extruded from the open nozzles to form meltblown filaments from the melt blend. Approximately 472 SCFM of compressed air, equivalent to a jet-to-melt mass ratio of 26, is heated such that the air exhibits a temperature of about 395° F. at the spinnerette. A forming vacuum operating at 23 mBar pressure pulls air through a collection device, such as a non-macro patterned, weaved forming belt of air permeability of 700 SCFM, thus collecting the meltblown filaments to form a fibrous structure that conforms to the micro texture from the weaving pattern of the collection device. The collection device can also have macro patterns, in which meltblown filaments will first conform to the macro patterns of the collection device, and then conform to the micro weave texture of the reinforcing element of the collection device.

A 20%27.5%47.5%5% blend of Lyondell-Basell PH835 polypropylene:Lyondell-Basell Metocene MF650W polypropylene:Lyondell-Basell Metocene MF650X Polyvel S1416 wetness agent is dry blended, to form a melt blend. The melt blend is heated to 400° F. through a melt extruder. A 15.5 inch wide Biax 12 row spinnerette with 192 nozzles per cross-direction inch, commercially available from Biax Fiberfilm Corporation, is utilized. 24 nozzles per cross-direction inch of the 192 nozzles have a 0.018 inch inside diameter while the remaining nozzles are solid, i.e. there is no opening in the nozzle. Approximately 0.5 grams per hole per minute (ghm) of the melt blend is extruded from the open nozzles to form meltblown filaments from the melt blend. Approximately 320 SCFM of compressed air, equivalent to a jet-to-melt mass ratio of 7, is heated such that the air exhibits a temperature of about 395° F. at the spinnerette. Approximately 750 g/minute of Golden Isle (from Georgia Pacific) 4725 semi-treated SSK pulp is defibrillated through a hammermill to form SSK wood pulp fibers (solid additive). Air at a temperature of about 85 to 90° F. and about 80% relative humidity (RH) is drawn into the hammermill. Approximately 35 kg/min of air split into two symmetric streams carry the pulp fibers to a solid additive spreader. The solid additive spreader turns the pulp fibers and distributes the pulp fibers in the cross-direction such that the pulp fibers are injected into the meltblown filaments at a 45° angle (with respect to the flow of the meltblown filaments). A forming box surrounds the area where the meltblown filaments and pulp fibers are commingled. This forming box is designed to reduce the amount of air allowed to enter or escape from this commingling area. A forming vacuum pulls air through the same collection device carrying the first said scrim layer, thus collecting the commingled meltblown filaments and pulp fibers to form a fibrous structure on top of the patterned scrim layer (scrim component). The fibrous structure formed by this process comprises about 80% by dry fibrous structure weight of pulp and about 20% by dry fibrous structure weight of meltblown filaments.

A third layer composed of the identical formulation as the first said scrim can be added to the opposite side of the co-formed layer, thus encapsulating the co-form pulp core to prevent linting. To make the meltblown filaments for this exterior layer, A 15.5 inch wide Biax 12 row spinnerette with 192 nozzles per cross-direction inch, commercially available from Biax Fiberfilm Corporation, is utilized. 8 nozzles per cross-direction inch of the 192 nozzles have a 0.018 inch inside diameter while the remaining nozzles are solid, i.e. there is no opening in the nozzle. Approximately 0.18 grams per hole per minute (ghm) of the melt blend is extruded from the open nozzles to form meltblown filaments from the melt blend. Approximately 425 SCFM of compressed air, equivalent to a jet-to-melt mass ratio of 26, is heated such that the air exhibits a temperature of about 395° F. at the spinnerette. A forming vacuum operating at 23 mBar pressure pulls air through the same collection device carrying the first said scrim layer and said co-form layer, thus collecting the commingled meltblown filaments to form a fibrous structure opposite side of the first said scrim layer.

After the fibrous structure, with additional meltblown filaments (scrim layers) has been formed on the collection device, such as a patterned molding member, the fibrous structure is calendered at elevated temperature, while the fibrous structure is still on the collection device. In this example, the fibrous structure with the first said scrim side facing the macro patterned molding member with micro weave pattern, is calendared. About 240 PLI (Average pounds per linear CD inch across the patterned molding member CD width of 21"), which creates pillows (macro protrusions) and/or micro pillows (micro protrusions) and knuckles, was applied with a flat or even surface metal anvil roll facing the fibrous structure and a flat or even surface rubber coated roll facing the patterned molding member. The metal anvil roll has an internal temperature of 290° F. as supplied by an oil heater.

The fibrous structure may be convolutedly wound to form a roll of fibrous structure. After the fibrous structure is collected in roll form, it is further converted by being lotioned and cut to form a finished product.

Process Example 4—Process for Making Emboss Macro Texture with Micro Surface Protrusion Fibrous Structure of the Present Invention Making of a multi-ply structure, including at least one scrim layer (scrim component), with embossed macro texture and micro surface protrusion features, is described in this example.

A 21%27.5%47.5%4% blend of Lyondell-Basell PH835 polypropylene Lyondell-Basell Metocene MF650W polypropylene:Lyondell-Basell Metocene MF650X Ampacet 412951 opacifier is dry blended, to form a melt blend. A meltblown layer of the meltblown filaments, such as a scrim component, is produced first. To make the meltblown filaments for the scrim component, a 15.5 inch wide Biax 12 row spinnerette with 192 nozzles per cross-direction inch, commercially available from Biax Fiberfilm Corporation, is utilized. 32 nozzles per cross-direction inch of the 192 nozzles have a 0.018 inch inside diameter while the remaining nozzles are solid, i.e. there is no opening in the nozzle. Approximately 0.2 grams per hole per minute (ghm) of the melt blend is extruded from the open nozzles to form meltblown filaments from the melt blend. Approximately 472 SCFM of compressed air, equivalent to a jet-to-melt mass ratio of 26, is heated such that the air exhibits a temperature of about 395° F. at the spinnerette. A forming vacuum operating at 23 mBar pressure pulls air through a collection device, such as a weaved forming belt Velostat 170PC 740 fabric by Albany International, thus collecting the meltblown filaments to form a fibrous structure that conforms to the micro texture from the weaving pattern of the collection device's reinforcing element.

A 20%27.5%47.5%5% blend of Lyondell-Basell PH835 polypropylene:Lyondell-Basell Metocene MF650W polypropylene:Lyondell-Basell Metocene MF650X:Polyvel S1416 wetness agent is dry blended, to form a melt blend. The melt blend is heated to 400° F. through a melt extruder. A 15.5 inch wide Biax 12 row spinnerette with 192 nozzles per cross-direction inch, commercially available from Biax Fiberfilm Corporation, is utilized. 24 nozzles per cross-direction inch of the 192 nozzles have a 0.018 inch inside diameter while the remaining nozzles are solid, i.e. there is no opening in the nozzle. Approximately 0.5 grams per hole per minute (ghm) of the melt blend is extruded from the open nozzles to form meltblown filaments from the melt blend. Approximately 320 SCFM of compressed air, equivalent to a jet-to-melt mass ratio of 7, is heated such that the air exhibits a temperature of about 395° F. at the spinnerette. Approximately 750 g/minute of Golden Isle (from Georgia Pacific) 4725 semi-treated SSK pulp is defibrillated through a hammermill to form SSK wood pulp fibers (solid additive). Air at a temperature of about 85 to 90° F. and about 80% relative humidity (RH) is drawn into the hammermill. Approximately 35 kg/min of air split into two symmetric streams carry the pulp fibers to a solid additive spreader. The solid additive spreader turns the pulp fibers and distributes the pulp fibers in the cross-direction such that the pulp fibers are injected into the meltblown filaments at a 45° angle (with respect to the flow of the meltblown filaments). A forming box surrounds the area where the meltblown filaments and pulp fibers are commingled. This forming box is designed to reduce the amount of air allowed to enter or escape from this commingling area. A forming vacuum operating at 48 mBar pressure pulls air through the same collection device carrying the first said scrim layer, thus collecting the commingled meltblown filaments and pulp fibers to form a fibrous structure on top of the pattern scrim layer. The fibrous structure formed by this process comprises about 80% by dry fibrous structure weight of pulp and about 20% by dry fibrous structure weight of meltblown filaments.

A third layer composed of the identical formulation as the first said scrim can be added to the opposite side of the co-formed layer, thus encapsulating the co-form pulp core to prevent linting. To make the meltblown filaments for this exterior layer, A 15.5 inch wide Biax 12 row spinnerette with 192 nozzles per cross-direction inch, commercially available from Biax Fiberfilm Corporation, is utilized. 8 nozzles per cross-direction inch of the 192 nozzles have a 0.018 inch inside diameter while the remaining nozzles are solid, i.e. there is no opening in the nozzle. Approximately 0.18 grams per hole per minute (ghm) of the melt blend is extruded from the open nozzles to form meltblown filaments from the melt blend. Approximately 425 SCFM of compressed air, equivalent to a jet-to-melt mass ratio of 26, is heated such that the air exhibits a temperature of about 395° F. at the spinnerette. A forming vacuum operating at 23 mBar pressure pulls air through the same collection device carrying the first said scrim layer and said co-form layer, thus collecting the commingled meltblown filaments to form a fibrous structure opposite side of the first said scrim layer.

After the fibrous structure, with additional meltblown filaments (scrim layers) has been formed on the collection device, the fibrous structure is embossed at elevated temperature. In this example, the fibrous structure side with the first said scrim meltblown layer is facing the patterned roll during emboss operation. About 240 PLI (Average pounds per linear CD inch across the patterned molding member CD width of 21"), which creates pillows (macro protrusions) and/or micro pillows (micro protrusions) and knuckles, was applied with a flat or even surface metal anvil roll facing the opposite side of the fibrous structure. The metal anvil roll has an internal temperature of 290° F. as supplied by an oil heater.

The fibrous structure may be convolutedly wound to form a roll of fibrous structure. After the fibrous structure is collected in roll form, it is further converted by being lotioned and cut to form a finished product.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 12 hours prior to the test. Except where noted all tests are conducted in such conditioned room, all tests are conducted under the same environmental conditions and in such conditioned room. Discard any damaged product. Do not test samples that have defects such as wrinkles, tears, holes, and like. All instruments are calibrated according to manufacturer's specifications.

Mileage Test Method

Mileage of a pre-moistened fibrous structure, for example a pre-moistened floor cleaning pad, is measured as coverage area of the liquid composition distributed on a floor surface. If the pre-moistened fibrous structure is in a package, open the package and remove the pre-moistened wipe, ensuring that the pre-moistened wipe is not subjected to pressure, such as squeezing, that would cause the liquid composition to be expressed from the pre-moistened wipe. If the pre-moistened wipe is in a stack within a package, open the package and remove a pre-moistened wipe from the middle of the stack, again ensuring that the pre-moistened wipe is not subjected to pressure, such as squeezing, that would cause the liquid composition to be expressed from the pre-moistened wipe. This Mileage test is conducted in temperature (70° F.) and humidity (45% RH) controlled room. The room should be well-lit to assist visual assessment of liquid distribution. A matte black tile floor (such as Sierra Field Tile in plain black 12 inch square) is chosen to conduct the testing to further assist the observation of streak appearance.

A mop sled is constructed from aluminum frame, Teflon bars, velcro and Swiffer® Sweeper handle, which holds a Swiffer® Sweeper head in place during mopping and guides the head on the floor.

A mop head is modified by cutting off most of the Swiffer® Sweeper handle, leaving 10 inch bottom part of the handle. During testing, a known weight is put on the mop head to assert constant pressure on the test sample. Because the tester is holding the handle of the sled, no additional pressure is asserted on the wipe sample.

Clean the floor with a 20% IPA and 80% water solution. Spray the solution onto the floor liberally and use a squeegee to remove excess fluid. Let the floor dry completely before begin testing. The floor needs to be cleaned with the IPA/water mixture after every 3 testings or when switching test products to remove accumulation of cleaning lotion from wipes.

Record the weight of the modified mop head. Attach the pre-moistened fibrous structure to the modified mop head and record the weight. Calculate the difference of those two weights as "initial pad weight".

Place the mop head into the mopping sled and place 7.125 lbs weight with Velcro attachment onto the mop head. Making sure to not mop over an area more than once.

Figure 18:
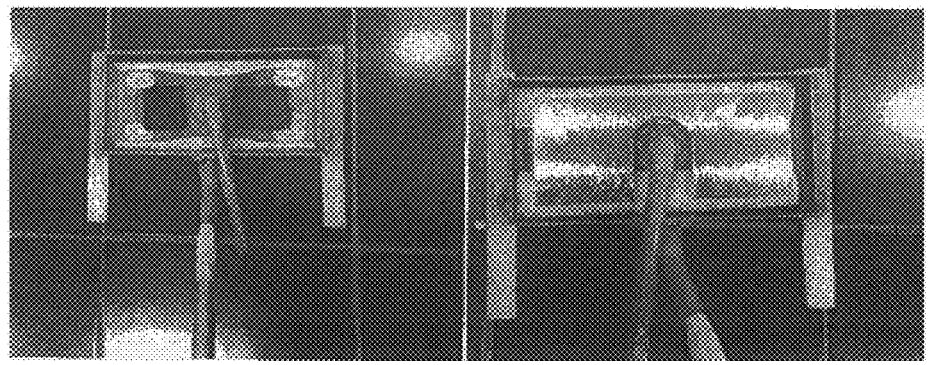
FIG. 18 are images of the mopping head apparatus used in the Mileage Test Method.
Figure 19:
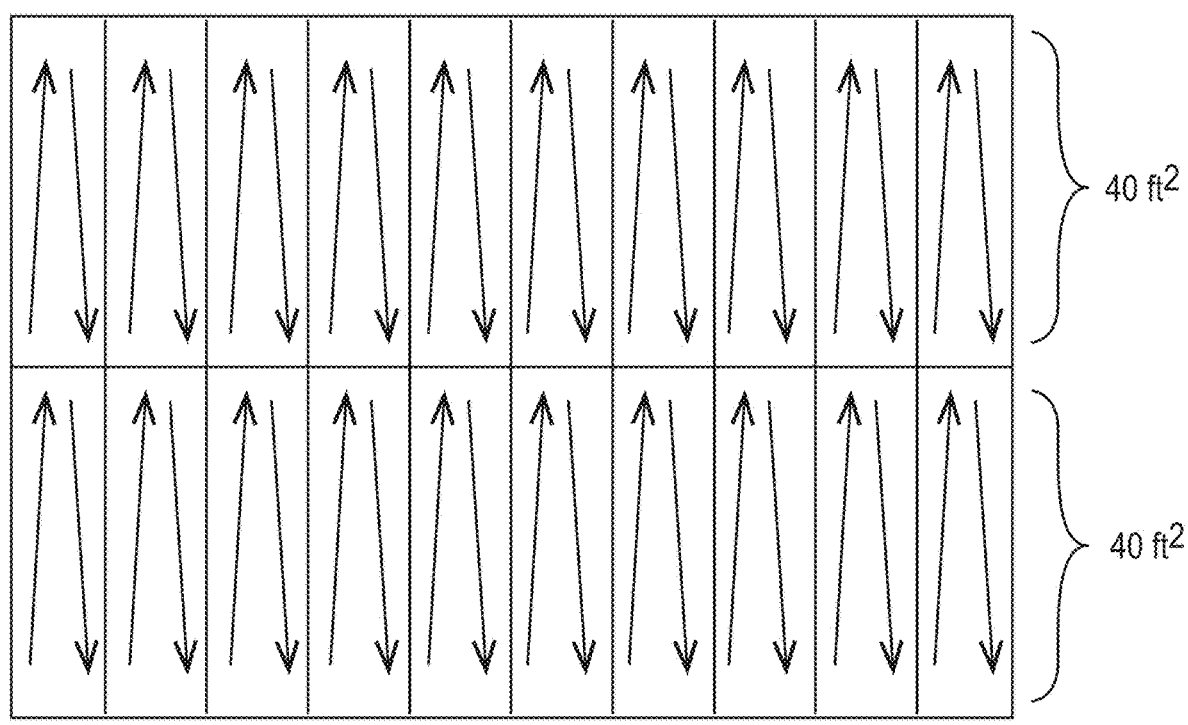
FIG. 19 is the pattern for mopping used in the Mileage Test Method.

Start by mopping in the forward direction following the mopping pattern in FIG. 18. The cadence (time) should be 1 second for the forward direction and 1 second for the backward direction in an overlapping manner (See FIG. 19—arrows show direction of movement). Continue mopping until you have completed 80 ft$^2$. Remove the weight from the mop head. It may take a while for the floor to be completely dry. Using Bounty towel drying the floor may significantly shorten the waiting time and decrease the amount of liquid loss due to evaporation from the testing subject. Once the floor is dry place the mop head with the substrate back into the mop sled and apply the weight. Continue to mop in the same fashion as stated previously. Continue mopping until streaks as shown in the 50% coverage image in FIG. 20 are visible to tester. This 50% coverage should be on both the forward and backstroke. Stop the test at this point by removing the pre-moistened fibrous structure from the floor surface. Record "final pad weight" and air drying the pre-moistened fibrous structure to remove any remaining liquid composition.

Calculate the surface area (ft$^2$) that the liquid composition covered prior to stopping the test. This surface area (ft$^2$) is used to calculate the mileage value of ft$^2$/pre-moistened fibrous structure.

Once the fibrous structure is dry, the basis weight of the dried fibrous structure is measured according to the Basis Weight Test Method described herein. The surface area that the liquid composition covered (ft$^2$) and the basis weight (in units of gsm) of the above dried fibrous structure are used to calculate the mileage value of ft$^2$/gsm.

Prior to drying the pre-moistened fibrous structure, the surface area of the pre-moistened fibrous structure is measured (ft$^2$). This surface area of the pre-moistened fibrous structure (ft$^2$) and the surface area that liquid composition covered (ft$^2$) is used to calculate the mileage value of ft$^2$/ft$^2$ of the pre-moistened fibrous structure.

Fibrous Structure Basis Weight Test Method

Basis weight is measured prior to the application of any end-use lotion, cleaning solution, or other liquid composition, etc. to the fibrous structure or wipe, and follows a modified EDANA 40.3-90 (February 1996) method as described herein below.

1. Cut at least three test pieces of the fibrous structure or wipe to specific known dimensions using a pre-cut metal die and die press. Each test piece is cut to have an area of at least 0.01 m$^2$.

2. Use a balance to determine the mass of each test piece in grams, calculate basis weight (mass per unit area), in grams per square meter (gsm), using equation (1).

$$\text{Basis Weight} = \frac{\text{Mass of Test Piece (g)}}{\text{Area of Test Piece (m}^2\text{)}} \quad (1)$$

3. For a fibrous structure or wipe sample, report the numerical average basis weight for all test pieces.

4. If only a limited amount of the fibrous structure or wipe is available, basis weight may be measured and reported as the basis weight of one test piece, the largest rectangle possible.

5. If measuring a core layer (core component), a scrim layer (scrim component), or a combination of core and scrim layers, the respective layer is collected during the making operation without the other layers and then the basis weight of the respective layer is measured as outlined above.

Diameter Test Method

The diameter of a fibrous element, for example a filament, discrete or within a fibrous structure is determined by using a Scanning Electron Microscope (SEM) or an Optical Microscope and an image analysis software. A magnification of 200 to 10,000 times is chosen such that the filaments are suitably enlarged for measurement. When using the SEM, the samples are sputtered with gold or a palladium compound to avoid electric charging and vibrations of the filaments in the electron beam. A manual procedure for determining the filament diameters is used from the image (on monitor screen) taken with the SEM or the optical microscope. Using a mouse and a cursor tool, the edge of a randomly selected filament is sought and then measured across its width (i.e., perpendicular to filament direction at that point) to the other edge of the filament. A scaled and calibrated image analysis tool provides the scaling to get actual reading in μm. For filaments within a fibrous structure, several filaments are randomly selected across the sample of the fibrous structure using the SEM or the optical microscope. At least two portions of the fibrous structure are cut and tested in this manner Altogether at least 100 such measurements are made and then all data are recorded for statistical analysis. The recorded data are used to calculate average (mean) of the filament diameters, standard deviation of the filament diameters, and median of the filament diameters.

Another useful statistic is the calculation of the amount of the population of filaments that is below a certain upper limit. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular filament as di.

In the case that the filaments have non-circular cross-sections, the measurement of the filament diameter is determined as and set equal to the hydraulic diameter which is four times the cross-sectional area of the filament divided by the perimeter of the cross-section of the filament (outer perimeter in case of hollow filaments). The number-average diameter, alternatively average diameter is calculated as:

$$d_{num} = \frac{\sum_{i=1}^{n} d_i}{n}$$

Capacity Test Method

Capacity of a pre-moistened fibrous structure, for example a pre-moistened floor cleaning pad, is measured as coverage area of the liquid composition distributed on a floor surface. If the pre-moistened fibrous structure is in a package, open the package and remove the pre-moistened wipe, ensuring that the pre-moistened wipe is not subjected to pressure, such as squeezing, that would cause the liquid composition to be expressed from the pre-moistened wipe. If the pre-moistened wipe is in a stack within a package, open the package and remove a pre-moistened wipe from the middle of the stack, again ensuring that the pre-moistened wipe is not subjected to pressure, such as squeezing, that would cause the liquid composition to be expressed from the pre-moistened wipe. This Capacity test is conducted in a room that is void of air drafts or other wind that may cause the liquid composition present on a floor to evaporate more quickly than if the air drafts or wind was not present in the room.

A pre-moistened fibrous structure sample is attached to a Swiffer® Sweeper head. Immediately after attaching the pre-moistened fibrous structure sample, initiate mopping with an applied continued pressure of 0.1-0.3 psi a clean, new ceramic floor surface (at least 900 ft$^2$) in the pattern as shown in FIG. 12 making sure to not mop over an area more than once. Use a metronome at 40 bpm to control stroke duration—each beat represents one direction. Continue mopping until streaks as shown in the 50% coverage image in FIG. 13 are visible to tester. Stop the test at this point by removing the pre-moistened fibrous structure from the floor surface and air drying the pre-moistened fibrous structure to remove any remaining liquid composition.

Calculate the surface area (ft$^2$) that the liquid composition covered prior to stopping the test. This surface area (ft$^2$) is used to calculate the capacity value of ft$^2$/pre-moistened fibrous structure.

Once the fibrous structure is dry, the basis weight of the dried fibrous structure is measured according to the Basis Weight Test Method described herein. The surface area that the liquid composition covered (ft$^2$) and the basis weight (in units of gsm) of the above dried fibrous structure are used to calculate the capacity value of ft$^2$/gsm.

Prior to drying the pre-moistened fibrous structure, the surface area of the pre-moistened fibrous structure is measured (ft$^2$). This surface area of the pre-moistened fibrous structure (ft$^2$) and the surface area that liquid composition covered (ft$^2$) is used to calculate the capacity value of ft$^2$/ft$^2$ of the pre-moistened fibrous structure.

MikroCAD Test Method

Surfaces of a fibrous structure, such as a pre-moistened fibrous structure, based on heights, can be identified and/or measured using a GFM Mikrocad Optical Profiler instrument commercially available from GFMesstechnik GmbH, Warthestraße 21, D14513 Teltow/Berlin, Germany. The GFM Mikrocad Optical Profiler instrument includes a compact optical measuring sensor based on the digital micro mirror projection, consisting of the following main components: a) DMD projector with 1024×768 direct digital controlled micro mirrors, b) CCD camera with high resolution (1300×1000 pixels), c) projection optics adapted to a measuring area of at least 44 mm×33 mm, and d) matching resolution recording optics, a table tripod based on a small hard stone plate, a cold light source, a measuring, control, and evaluation computer, measuring, control, and evaluation software ODSCAD 4.0, English version; and adjusting probes for lateral (x-y) and vertical (z) calibration.

The GFM Mikrocad Optical Profiler system measures the surface height of a fibrous structure sample using the digital micro-mirror pattern projection technique. The result of the analysis is a map of surface height (z) vs. xy displacement. The system has a field of view of 140×105 mm with a resolution of 29 microns. The height resolution should be set to between 0.10 and 1.00 micron. The height range is 64,000 times the resolution.

The relative height of different portions of a surface of a fibrous structure such as the fibrous structure's surface, a protruding surface (macro protrusion surface) of the fibrous structure and/or a contact surface (micro protrusion surface) of a fibrous structure can be visually determined via a topography image, which is obtained for each fibrous structure sample as described below. At least three samples are measured. Actual height values can be obtained as follows below.

To measure the height or elevation of a surface pattern or portion of a surface pattern on a surface of a fibrous structure, for example a fibrous structure product, such as a cleaning pad, the following can be performed (1) If the fibrous structure, fibrous structure product, or cleaning pad is pre-moistened, dry completely in a conditioned room at a temperature of 50° C.±1.0° C. and a relative humidity of 35%±2% and then condition in a conditioned room at a temperature of 23° C.±1.0° C. and a relative humidity of 50%±2% for at least 12 hours. (2) Turn on the cold light source. The settings on the cold light source should be 4 and C, which should give a reading of 3000K on the display, (3) Turn on the computer, monitor and printer and open the ODSCAD 4.0 or higher Mikrocad Software, (4) Select "Measurement" icon from the Mikrocad taskbar and then click the "Live Pic" button, (5) Place a fibrous structure product sample, for example a cleaning pad, of at least 5 cm by 5 cm in size, under the projection head, without any mechanical clamping, and adjust the distance for best focus, (6) Click the "Pattern" button repeatedly to project one of several focusing patterns to aid in achieving the best focus (the software cross hair should align with the projected cross hair when optimal focus is achieved). Position the projection head to be normal to the fibrous structure product sample surface, for example the cleaning pad sample surface, (7) Adjust image brightness by changing the aperture on the camera lens and/or altering the camera "gain" setting on the screen. Set the gain to the lowest practical level while maintaining optimum brightness so as to limit the amount of electronic noise. When the illumination is optimum, the red circle at bottom of the screen labeled "I.O." will turn green, (8) Select Standard measurement type, (9) Click on the "Measure" button. This will freeze the live image on the screen and, simultaneously, the surface capture process will begin. It is important to keep the sample still during this time to avoid blurring of the captured images. The full digitized surface data set will be captured in approximately 20 seconds, (10) Save the data to a computer file with ".omc" extension. This will also save the camera image file ".kam", (11) Export the file to the FD3 v1.0 format, (12) Measure and record at least three areas from each sample, (13) Import each file into the software package SPIP (Image Metrology, A/S, Hørsholm, Denmark), (14) Using the Averaging profile tool, draw a profile line perpendicular to height or elevation (such as embossment) transition region. Expand the averaging box to include as much of the height or elevation (embossment) as practical so as to generate and average profile of the transition region (from top surface to the bottom of the surface pattern or portion of surface pattern (such as an embossment) and backup to the top surface.). In the average line profile window, select a pair of cursor points.

To move the surface data into the analysis portion of the software, click on the clipboard/man icon, (15) Now, click on the icon "Draw Lines". Draw a line through the center of a region of features defining the texture of interest. Click on Show Sectional Line icon. In the sectional plot, click on any two points of interest, for example, a peak and the baseline, then click on vertical distance tool to measure height in microns or click on adjacent peaks and use the horizontal distance tool to determine in-plane direction spacing; and (16) for height measurements, use 3 lines, with at least 5 measurements per line, discarding the high and low values for each line, and determining the mean of the remaining 9 values. Also record the standard deviation, maximum, and minimum. For x and/or y direction measurements, determine the mean of 7 measurements. Also record the standard deviation, maximum, and minimum. Criteria that can be used to characterize and distinguish texture include, but are not limited to, occluded area (i.e. area of features), open area (area absent of features), spacing, in-plane size, and height. If the probability that the difference between the two means of texture characterization is caused by chance is less than 10%, the textures can be considered to differ from one another.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fibrous structure comprising a co-formed fibrous structure comprising a plurality of fibers commingled with a plurality of first spun filaments such that the plurality of fibers are dispersed in the plurality of first spun filaments, wherein the fibrous structure further comprises a fibrous structure surface comprising one or more pillows, wherein at least one of the one or more pillows comprises a macro protrusion surface comprising a plurality of micro protrusions, wherein the plurality of micro protrusions are in the form of a contact surface of the fibrous structure and wherein the fibrous structure surface further comprises one or more knuckles, wherein the one or more knuckles do not comprise micro protrusions.

2. The fibrous structure according to claim 1 wherein the plurality of micro protrusions form a micro protrusion surface having a micro protrusion surface surface area.

3. The fibrous structure according to claim 2 wherein the micro protrusion surface surface area is less than the fibrous structure surface's surface area.

4. The fibrous structure according to claim 3 wherein the micro protrusion surface surface area is greater than 50% to about 99% of the fibrous structure surface surface area.

5. The fibrous structure according to claim 1 wherein the micro protrusions further comprises a plurality of second spun filaments.

6. The fibrous structure according to claim 5 wherein at least one of the first and second spun filaments comprises a thermoplastic polymer.

7. The fibrous structure according to claim 6 wherein the thermoplastic polymer is selected from the group consisting of: polyolefins, polyesters, polylactic acids, polycaprolactones, polyhydroxybutyrates, and mixtures thereof.

8. The fibrous structure according to claim 7 wherein the thermoplastic polymer comprises a polyolefin.

9. The fibrous structure according to claim 8 wherein the polyolefin is selected from the group consisting of: polypropylene, propylene copolymers, polyethylene, ethylene copolymers, and mixtures thereof.

10. The fibrous structure according to claim 5 wherein at least one of the first and second spun filaments exhibits a diameter of less than 50 μm as measured according to the Diameter Test Method.

11. The fibrous structure according to claim 5 wherein the second spun filaments form a scrim layer of the fibrous structure.

12. The fibrous structure according to claim 11 wherein the scrim layer is void of pulp fibers.

13. The fibrous structure according to claim 1 wherein one or more of the micro protrusions exhibits an average absolute surface height value (Sa) of greater than 250 μm as measured according to the MikroCAD Test Method.

14. The fibrous structure according to claim 1 wherein at least one of the micro protrusions is void of pin holes.

15. The fibrous structure according to claim 1 wherein at least one of the micro protrusions exhibits a Peak-to-Valley value of greater than 50 μm.

16. The fibrous structure according to claim 1 wherein at least one of the micro protrusions exhibits a Valley-to-Valley value of greater than 100 μm.

17. The fibrous structure according to claim 1 wherein the fibrous structure further comprises a fibrous structure core component comprising the co-formed fibrous structure.

18. The fibrous structure according to claim 1 wherein the fibrous structure is a floor cleaning pad.

19. The fibrous structure according to claim 1 wherein the fibrous structure further comprises a liquid composition.

20. The fibrous structure according to claim 19 wherein the liquid composition comprises a surfactant, an acidifying agent, and an amide.

* * * * *